(12) United States Patent
Kyle et al.

(10) Patent No.: US 7,256,193 B2
(45) Date of Patent: *Aug. 14, 2007

(54) THERAPEUTIC AGENTS USEFUL FOR TREATING PAIN

(75) Inventors: Donald J. Kyle, Newtown, PA (US); Sun Qun, Princeton, NJ (US)

(73) Assignee: Euro-Celtique S.A. (LU)

(*) Notice: Subject to any disclaimer, the term of this patent is extended or adjusted under 35 U.S.C. 154(b) by 0 days.

This patent is subject to a terminal disclaimer.

(21) Appl. No.: 11/368,133

(22) Filed: Mar. 2, 2006

(65) Prior Publication Data

US 2006/0148814 A1   Jul. 6, 2006

Related U.S. Application Data

(63) Continuation of application No. 10/355,186, filed on Jan. 31, 2003, now Pat. No. 7,071,335.

(60) Provisional application No. 60/352,855, filed on Feb. 1, 2002, provisional application No. 60/411,043, filed on Sep. 17, 2002.

(51) Int. Cl.
A61K 31/496 (2006.01)

(52) U.S. Cl. ................... 514/253.01; 544/360

(58) Field of Classification Search ............. 514/253.01
See application file for complete search history.

(56) References Cited

U.S. PATENT DOCUMENTS

| | | |
|---|---|---|
| 4,439,606 A | 3/1984 | Du et al. |
| 4,450,272 A | 5/1984 | Du et al. |
| 5,039,680 A | 8/1991 | Imperato et al. |
| 5,075,341 A | 12/1991 | Mendelson et al. |
| 5,198,459 A | 3/1993 | Imperato et al. |
| 5,232,934 A | 8/1993 | Downs |
| 5,430,033 A | 7/1995 | Cliffe et al. |
| 5,442,064 A | 8/1995 | Pieper et al. |
| 5,461,047 A | 10/1995 | Hansen, Jr. et al. |
| 5,556,837 A | 9/1996 | Nestler et al. |
| 5,556,838 A | 9/1996 | Mayer et al. |
| 5,574,052 A | 11/1996 | Rose et al. |
| 5,756,504 A | 5/1998 | Bock et al. |
| 5,762,925 A | 6/1998 | Sagen et al. |
| 5,780,472 A | 7/1998 | Cho et al. |
| 5,789,412 A | 8/1998 | Halazy et al. |
| 5,792,768 A | 8/1998 | Kulagowski et al. |
| 5,922,872 A | 7/1999 | Cook et al. |
| 6,028,195 A | 2/2000 | Cho et al. |
| 6,109,269 A | 8/2000 | Rise et al. |
| 6,124,299 A | 9/2000 | Baindur et al. |
| 6,204,284 B1 | 3/2001 | Beer et al. |
| 6,239,267 B1 | 5/2001 | Duckworth et al. |
| 6,329,395 B1 | 12/2001 | Dugar et al. |
| 6,335,180 B1 | 1/2002 | Julius et al. |
| 6,406,908 B1 | 6/2002 | McIntyre et al. |
| 6,723,730 B2 | 4/2004 | Bakthavatchalam et al. |
| 2003/0153596 A1 | 8/2003 | Suh et al. |
| 2003/0158188 A1 | 8/2003 | Lee et al. |
| 2003/0158198 A1 | 8/2003 | Lee et al. |

FOREIGN PATENT DOCUMENTS

| | | |
|---|---|---|
| EP | 1 014 116 | 6/2000 |
| EP | 1 122 242 | 8/2001 |
| WO | WO 96/21648 | 7/1996 |
| WO | WO 98/00402 | 1/1998 |
| WO | WO 98/25167 | 6/1998 |
| WO | WO 99/07672 | 2/1999 |

(Continued)

OTHER PUBLICATIONS

Martinez, Mini Reviews in Medicinal Chemistry, vol. 3, pp. 718-718(1) (2003) (Abstract).*
Valenzano et al. Current Medicinal Chemistry, vol. 11, pp. 3185-3202 (2004).*
Berkow et al., "The Merck Manual of Medical Information," pp. 345-350 (1997).
Berkow et al., "The Merck Manual of Medical Information," pp. 352-355 (1997).
Berkow et al., "The Merck Manual of Medical Information," pp. 496-500 (1997).
Berkow et al., "The Merck Manual of Medical Information," pp. 525-526 (1997).

(Continued)

*Primary Examiner*—Emily Bernhardt
(74) *Attorney, Agent, or Firm*—Jones Day

(57) ABSTRACT

A Compound of formula

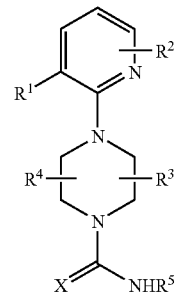

(wherein X is O or S and $R^1$-$R^5$ are disclosed herein) or a pharmaceutically acceptable salt thereof (each being a "Piperazine Compound"), pharmaceutical compositions comprising a Piperazine Compound and methods for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, amyotrophic lateral sclerosis, dementia, retinopathy, a muscle spasm, a migraine, vomiting, dyskinesia, or depression in an animal comprising administering to an animal in need thereof an effective amount of a Piperazine Compound are disclosed.

18 Claims, No Drawings

FOREIGN PATENT DOCUMENTS

| | | |
|---|---|---|
| WO | WO 99/37304 | 7/1999 |
| WO | WO 00/52001 | 9/2000 |
| WO | WO 02/05819 | 1/2002 |
| WO | WO 02/08221 | 1/2002 |
| WO | WO 02/16318 | 2/2002 |
| WO | WO 02/072536 | 9/2002 |
| WO | WO 02/076946 | 10/2002 |
| WO | WO 03/022809 | 3/2003 |
| WO | WO 03/062209 | 7/2003 |
| WO | WO 03/068749 | 8/2003 |

OTHER PUBLICATIONS

Berkow et al., "The Merck Manual of Medical Information," pp. 528-530 (1997).

Berkow et al., "The Merck Manual of Medical Information," pp. 530-532 (1997).

Berkow et al., "The Merck Manual of Medical Information," pp. 631-634 (1997).

Bevan et al., "Vanilloid Receptors: Pivotal Molecules in Nocciception," *Current Opinions in CPNS Investigational Drugs* 2(2): 178-185 (2000).

Chiamulera et al., "Reinforcing and locomotor stimulant effects of cocaine are absent in mGluR5 null mutant rice," *Nature Neuroscience* 4(9): 873-874 (2001).

Cooke, "Glycopyrrolate in bladder dysfunction," *SA Medical J.* 63:3 (1983).

Dogrul et al., "Peripheral and spinal antihyperalgesic activity of sib-1757, a metabotropic glutamate receptor (muGluR5) antagonist, in experimental neuropathic pain in rats," *Neuroscience Letters* 292(2): 115-118 (2000).

Foley, "Pain" *Cecil Textbook Of Medicine*, pp. 100-107 (1996).

Goodman and Gillman's *The Pharmaceutical Basis of Therapeutics*, pp. 506, 901-915 (J. Hardman and L. Limbird eds., 9th ed. 1996).

Herzog et al., "Urinary incontinence: Medical and psychosocial aspects," *Annu. Rev. Gerntol. Geriatr.* 9:74-119 (1989).

Kwak et al., "A Capsaicin-Receptor Antagonist, Capsazepine Reduces Inflammation-Induced Hyperalgesic Responses in the Rat: Evidence for an Endogenous Capsaicin-Like Substance," *Neuroscience* 86:619-26 (1998).

Levin et al., "Direct Measurement of the Anticholinergic Activity of a Series of Pharacological Compounds on the Canine and Rabbit Urinary Bladder," *J. Urology* 128:396-398 (1982).

Lopez-Rodriguez et al., "VRI receptor modulators as potential drugs for neuropathic pain," *Mini Rev. Med. Chem.* 3(7): 729-748 (2003).

Mirakhur et al., "Glycopyrrolate: Pharacology and clinical use," *Anaesthesia* 38: 1195-1204 (1983).

Ohkubo et al., "The Selective Capsaicin Antagonist Capsazepine Abolishes the Antinociceptive Action of Eugenol and Guaiacol," *J. Dent. Res.* 76(4): 848-851 (Apr. 1997).

Ossowska et al., "Blockade of the metabotropic glutamate receptor subtype 5 (mGluR5) produces antiparkinsonian-like effects in rats," *Neuropharmacol.* 41:413-420 (2001).

Pan et al., "Soluble Polymer-Supported Synthesis of Arylpiperazines," *Tett. Lett.* 39:9505-8 (1998).

Pomonis et al., "N-(4-Tertiarybutylphenyl)-4-(3-chlorphyridin-2-yl)tetrahyropyrazine-1(2H)-carbox-amide (BCTC), a novel, orally effective vanilloid receptor 1 antagonist with analgesic properties: II. In vivo characterization in rat models of inflammatory and neuropathic pain," *J Pharmacol Exp Ther.* 308(1):387-393 (2003).

Resnick, "Urinary Incontinence," *Lancet* 346:94-99 (1995).

Szallasi et al., "Vanilloid (Capsaicin) Receptors and Mechanisma," *Pharmacol. Revs* 51(2):159-211 (1999).

Tatarczynska et al., Potential anxiolytic- and antidepressant-like effects of mpep, a potent, selective and systemically active mglu5 receptor antagonist, *Brit. J. Pharmacol.* 132(7):1423-1430 (2001).

Tòth et al., "Design of a high-affinity competitive antagonist of the vanilloid receptor selective for the calcium entry-linked receptor population," *Mol. Pharmacol.* 65(2):282-291 (2004).

Urban et al., "In Vivo Pharmacology of SDZ 249-665, A Novel, Non-pungent Capsaicin Analogue," *Pain* 89:65-74 (2000).

Walker et al., "Metabotropic glutamate receptor subtype 5 (mglu5) and nociceptive function. I. Selective blockade of mglu5 receptors in models of acute, persistent and chronic pain," *Neuropharmacol.* 40:1-9 (2000).

Wang et al., "High affinity antagonists of the vanilloid receptor," *Mol. Pharmacol.* 62(4):947-56 (2002).

Wein, "Pharmacology of incontinence," *Urologic Clinics North Amer.* 22(3):557-577 (1995).

Will et al., "Novel allosteric antagonists shed light on mglu5 receptors and CNS disorders," *Trends in Pharmacological Sci.* 22(7):331-337 (2001).

Wrigglesworth et al., "Capsaicin-like Agonists," *Drugs of the Future* 23(5):531-538 (1998).

Wu et al., "Multiple Sensory and Functional Effects of Non-phenolic Aminodimethylene Nonivamide: An Approach to Capsaicin Antagonist, " *Gen. Pharmac.* 27(1):151-158 (1996).

\* cited by examiner

THERAPEUTIC AGENTS USEFUL FOR TREATING PAIN

This application is a continuation of U.S. application Ser. No. 10/355,186, filed Jan. 31, 2003, now U.S. Pat. No. 7,071,335, which claims the benefit of U.S. Provisional Application No. 60/352,855, filed Feb. 1, 2002, and U.S. Provisional Application No. 60/411,043, filed Sep. 17, 2002, all of which are incorporated herein by reference in their entirety.

1. FIELD OF THE INVENTION

The present invention relates to Piperazine Compounds; compositions comprising a Piperazine Compound; and methods for preventing or treating pain, urinary incontinence (UI), an ulcer, inflammatory-bowel disease (IBD), irritable-bowel syndrome (IBS), an addictive disorder, Parkinson's disease, parkinsonism, anxiety, epilepsy, stroke, a seizure, a pruritic condition, psychosis, a cognitive disorder, a memory deficit, restricted brain function, Huntington's chorea, amyotrophic lateral sclerosis (ALS), dementia, retinopathy, a muscle spasm, a migraine, vomiting, dyskinesia or depression, comprising administering to an animal in need thereof an effective amount of a Piperazine Compound.

2. BACKGROUND OF THE INVENTION

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, *Pain, in Cecil Textbook of Medicine* 100-107 (J. C. Bennett and F. Plum eds., 20th ed. 1996)).

Pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id.

UI is uncontrollable urination, generally caused by bladder-detrusor-muscle instability. UI affects people of all ages and levels of physical health, both in health care settings and in the community at large. At present, UI afflicts 15-30% of elderly people living at home, one-third of those living in acute-care settings, and at least one-half of those living in long-term care institutions (R. M. Resnick, *Lancet* 346:94 (1995)). Persons having UI are predisposed to also having urinary-tract infections, pressure ulcers, perineal rashes and urosepsis. Psychosocially, UI is associated with embarrassment, social stigmatization, depression and a risk of institutionalization (Herzo et al., *Annu. Rev. Gerontol. Geriatr.* 9:74 (1989)). Economically, the costs of UI are great; in the United States alone, health-care costs associated with UI are over $15 billion per annum.

Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity. For example, anticholinergics such as propantheline bromide and glycopyrrolate, and combinations of smooth-muscle relaxants such as a combination of racemic oxybutynin and dicyclomine or an anticholinergic, have been used to treat UI (See, e.g., A. J. Wein, *Urol. Clin. N. Am.* 22:557-577 (1995); Levin et al., *J. Urol.* 128:396-398 (1982); Cooke et al., *S. Afr. Med. J.* 63:3 (1983); R. K. Mirakhur et al., *Anaesthesia* 38:1195-1204 (1983)). These drugs are not effective, however, in all patients having uninhibited bladder contractions. Administration of anticholinergic medications represent the mainstay of this type of treatment.

None of the existing commercial drug treatments for UI, however, has achieved complete success in all classes of UI patients, nor has treatment occurred without significant adverse side effects. For example, drowsiness, dry mouth, constipation, blurred vision, headaches, tachycardia, and cardiac arrhythmia, which are related to the anticholinergic activity of traditional anti-UI drugs, can occur frequently and adversely affect patient compliance. Yet despite the prevalence of unwanted anticholinergic effects in many patients, anticholinergic drugs are currently prescribed for patients having UI. *The Merck Manual of Medical Information* 631-634 (R. Berkow ed., 1997).

Ulcers are sores occurring where the lining of the digestive tract has been eroded by stomach acids or digestive juices. The sores are typically well-defined round or oval lesions primarily occurring in the stomach and duodenum. About 1 in 10 people develop an ulcer. Ulcers develop as a result of an imbalance between acid-secretory factors, also known as "aggressive factors," such as stomach acid, pepsin, and *Helicobacter pylori* infection, and local mucosal-protective factors, such as secretion of bicarbonate, mucus, and prostaglandins.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Sucraflate is also used to treat ulcers. Sucraflate adheres to epithelial cells and is believed to form a protective coating at the base of an ulcer to promote healing. Sucraflate, however, can cause constipation, dry mouth, and interfere with the absorption of other drugs.

Antibiotics are used when *Helicobacter pylori* is the underlying cause of the ulcer. Often antibiotic therapy is coupled with the administration of bismuth compounds such as bismuth subsalicylate and colloidal bismuth citrate. The bismuth compounds are believed to enhance secretion of mucous and $HCO_3^-$, inhibit pepsin activity, and act as an antibacterial against *H. pylori*. Ingestion of bismuth compounds, however, can lead to elevated plasma concentrations of $Bi^{+3}$ and can interfere with the absorption of other drugs.

Prostaglandin analogues, such as misoprostal, inhibit secretion of acid and stimulate the secretion of mucous and bicarbonate and are also used to treat ulcers, especially ulcers in patients who require nonsteroidal anti-inflammatory drugs. Effective oral doses of prostaglandin analogues, however, can cause diarrhea and abdominal cramping. In addition, some prostaglandin analogues are abortifacients.

Carbenoxolone, a mineral corticoid, can also be used to treat ulcers. Carbenoxolone appears to alter the composition and quantity of mucous, thereby enhancing the mucosal barrier. Carbenoxolone, however, can lead to $Na^+$ and fluid retention, hypertension, hypokalemia, and impaired glucose tolerance.

Muscarinic cholinergic antagonists such as pirenzapine and telenzapine can also be used to reduce acid secretion and treat ulcers. Side effects of muscarinic cholinergic antagonists include dry mouth, blurred vision, and constipation. *The Merck Manual of Medical Information* 496-500 (R. Berkow ed., 1997) and *Goodman and Gilman's The Pharmacological Basis of Therapeutics* 901-915 (J. Hardman and L. Limbird eds., 9$^{th}$ ed. 1996).

IBD is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease typically affects the full thickness of the intestinal wall. Generally the disease affects the lowest portion of the small intestine (ileum) and the large intestine, but can occur in any part of the digestive tract.

Early symptoms of Crohn's disease are chronic diarrhea, crampy abdominal pain, fever, loss of appetite, and weight loss. Complications associated with Crohn's disease include the development of intestinal obstructions, abnormal connecting channels (fistulas), and abscesses. The risk of cancer of the large intestine is increased in people who have Crohn's disease. Often Crohn's disease is associated with other disorders such as gallstones, inadequate absorption of nutrients, amyloidosis, arthritis, episcleritis, aphthous stomatitis, erythema nodosum, pyoderma gangrenosum, ankylosing spondylitis, sacroilitis, uveitis, and primary sclerosing cholangitis. There is no known cure for Crohn's disease.

Cramps and diarrhea, side effects associated with Crohn's disease, can be relieved by anticholinergic drugs, diphenoxylate, loperamide, deodorized opium tincture, or codeine. Generally, the drug is taken orally before a meal.

Broad-spectrum antibiotics are often administered to treat the symptoms of Crohn's disease. The antibiotic metronidazole is often administered when the disease affects the large intestine or causes abscesses and fistulas around the anus. Long-term use of metronidazole, however, can damage nerves, resulting in pins-and-needles sensations in the arms and legs. Sulfasalazine and chemically related drugs can suppress mild inflammation, especially in the large intestine. These drugs, however, are less effective in sudden, severe flare-ups. Corticosteroids, such as prednisone, reduce fever and diarrhea and relieve abdominal pain and tenderness. Long-term corticosteroid therapy, however, invariably results in serious side effects such as high blood-sugar levels, increased risk of infection, osteoporosis, water retention, and fragility of the skin. Drugs such as azathioprine and mercaptourine can compromise the immune system and are often effective for Crohn's disease in patients that do not respond to other drugs. These drugs, however, usually need 3 to 6 months before they produce benefits and can cause serious side effects such as allergy, pancreatitis, and low white-blood-cell count.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. *The Merck Manual of Medical Information* 528-530 (R. Berkow ed., 1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely through out the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered. Sulfasalazine, olsalazie, prednisone, or mesalamine can be used to reduce inflammation. Azathioprine and mercaptopurine have been used to maintain remissions in ulcerative-colitis patients who would otherwise need long-term corticosteroid treatment. In severe cases of ulcerative colitis the patient is hospitalized and given corticosteroids intravenously. People with severe rectal bleeding can require transfusions and intravenous fluids. If toxic colitis develops and treatments fail, surgery to remove the large intestine can be necessary. Non-emergency surgery can be performed if cancer is diagnosed, precancerous legions are detected, or unremitting chronic disease would otherwise make the person an invalid or dependent on high doses of corticosteroids. Complete removal of the large intestine and rectum permanently cures ulcerative colitis. *The Merck Manual of Medical Information* 530-532 (R. Berkow ed., 1997) and *Goodman and Gilman's The Pharmacological Basis of Therapeutics* (J. Hardman and L. Limbird eds., 9$^{th}$ ed. 1996).

IBS is a disorder of motility of the entire gastrointestinal tract, causing abdominal pain, constipation, and/or diarrhea IBS affects three-times more women than men. In IBS stimuli such as stress, diet, drugs, hormones, or irritants can cause the gastrointestinal tract to contract abnormally. During an episode of IBS contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

There are two major types of IBS. The first type, spastic-colon type, is commonly triggered by eating, and usually produces periodic constipation and diarrhea with pain. Mucous often appears in the stool. The pain can come in bouts of continuous dull aching pain or cramps, usually in the lower abdomen. The person suffering from spastic-colon type IBS can also experience bloating, gas, nausea, headache, fatigue, depression, anxiety, and difficulty concentrating. The second type of IBS usually produces painless diarrhea or constipation. The diarrhea can begin suddenly and with extreme urgency. Often the diarrhea occurs soon after a meal and can sometimes occur immediately upon awakening.

Treatment of IBS typically involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. *The Merck Manual of Medical Information* 525-526 (R. Berkow ed., 1997).

Many drugs can cause physical and/or psychological addiction. Those most well known types of these drugs include opiates, such as heroin, opium, and morphine; sympathomimetics, including cocaine and amphetamines; sedative-hypnotics, including alcohol, benzodiazepines and barbiturates; and nicotine, which has effects similar to opioids and sympathomimetics. Drug addiction is characterized by a craving or compulsion for taking the drug and an inability to limit its intake. Additionally, drug dependence is associated with drug tolerance, the loss of effect of the drug following repeated administration, and withdrawal, the appearance of physical and behavioral symptoms when the drug is not consumed. Sensitization occurs if repeated administration of a drug leads to an increased response to each dose. Tolerance, sensitization, and withdrawal are phenomena evidencing a change in the central nervous system resulting from continued use of the drug. This change can motivate the addicted individual to continue consuming the drug despite serious social, legal, physical and/or professional consequences. (See, e.g., U.S. Pat. No. 6,109,269 to Rise et al.).

Certain pharmaceutical agents have been administered for treating addiction. U.S. Pat. No. 5,556,838 to Mayer et al. discloses the use of nontoxic NMDA-blocking agents co-administered with an addictive substance to prevent the development of tolerance or withdrawal symptoms. U.S. Pat. No. 5,574,052 to Rose et al. discloses co-administration of an addictive substance with an antagonist to partially block the pharmacological effects of the substance. U.S. Pat. No. 5,075,341 to Mendelson et al. discloses the use of a mixed opiate agonist/antagonist to treat cocaine and opiate addiction. U.S. Pat. No. 5,232,934 to Downs discloses administration of 3-phenoxypyridine to treat addiction. U.S. Pat. Nos. 5,039,680 and 5,198,459 to Imperato et al. disclose using a serotonin antagonist to treat chemical addiction. U.S. Pat. No. 5,556,837 to Nestler et. al. discloses infusing BDNF or NT-4 growth factors to inhibit or reverse neurological adaptive changes that correlate with behavioral changes in an addicted individual. U.S. Pat. No. 5,762,925 to Sagan discloses implanting encapsulated adrenal medullary cells into an animal's central nervous system to inhibit the development of opioid intolerance. U.S. Pat. No. 6,204,284 to Beer et al. discloses racemic (±)-1-(3,4-dichlorophenyl)-3-azabicyclo[3.1.0]hexane for use in the prevention or relief of a withdrawal syndrome resulting from addiction to drugs and for the treatment of chemical dependencies.

Parkinson's disease is a clinical syndrome comprising bradykinesia (slowness and poverty of movement), muscular rigidity, resting tremor (which usually abates during voluntary movement), and an impairment of postural balance leading to disturbance of gait and falling. The features of Parkinson's disease are a loss of pigmented, dopaminergic neurons of the substantia nigra pars compacta and the appearance of intracellular inclusions known as Lewy bodies (*Goodman and Gillman's The Pharmaceutical Basis of Therapeutics* 506 ($9^{th}$ ed. 1996)). Without treatment, Parkinson's disease progresses to a rigid akinetic state in which patients are incapable of caring for themselves. Death frequently results from complications of immobility, including aspiration pneumonia or pulmonary embolism. Drugs commonly used for the treatment of Parkinson's disease include carbidopa/levodopa, pergolide, bromocriptine, selegiline, amantadine, and trihexyphenidyl hydrochloride. There remains, however, a need for drugs useful for the treatment of Parkinson's disease and having an improved therapeutic profile.

Anxiety is a fear, apprehension, or dread of impending danger often accompanied by restlessness, tension, tachycardia, and dyspnea Other symptoms commonly associated with anxiety include depression, especially accompanied with dysthymic disorder (chronic "neurotic" depression); panic disorder; agoraphobia and other specific phobias; eating disorders; and many personality disorders. Often anxiety is unattached to a clearly identified treatable primary illness. If a primary illness is found, however, it can be desirable to deal with the anxiety at the same time as the primary illness.

Currently, benzodiazepines are the most commonly used anti-anxiety agents for generalized anxiety disorder. Benzodiazepines, however, carry the risk of producing impairment of cognition and skilled motor functions, particularly in the elderly, which can result in confusion, delerium, and falls with fractures. Sedatives are also commonly prescribed for treating anxiety. The azapirones, such as buspirone, are also used to treat moderate anxiety. The azapirones, however, are less useful for treating severe anxiety accompanied with panic attacks.

Epilepsy is a disorder characterized by the tendency to have recurring seizures. The etiology commonly consists of lesions in some part of the cortex, such as a tumor; developmental malformation; or damage due to trauma or stroke. In some cases the etiology is genetic. An epileptic seizure can be triggered by repetitive sounds, flashing lights, video games, or touching certain parts of the body. Epilepsy is typically treated with anti-seizure drugs. In epilepsy cases, where anti-seizure drugs are ineffective, and the defect in the brain is isolated to a small area of the brain, surgical removal of that part of the brain can be helpful in alleviating the seizures. In patients who have several sources for the seizures or who have seizures that spread quickly to all parts of the brain, surgical removal of the nerve fibers that connect the two sides of the brain can be helpful.

Examples of drugs for treating a seizure and epilepsy include carbamazepine, ethosuximide, gabapentin, lamotrignine, phenobarbital, phenytoin, primidone, valproic acid, trimethadione, bemzodiaepines, γ-vinyl GABA, acetazolamide, and felbamate. Anti-seizure drugs, however, can have side effects such as drowsiness; hyperactivity; hallucinations; inability to concentrate; central and peripheral nervous system toxicity, such as nystagmus, ataxia, diplopia, and vertigo; gingival hyperplasia; gastrointestinal disturbances such as nausea, vomiting, epigastric pain, and anorexia; endocrine effects such as inhibition of antidiuretic hormone, hyperglycemia, glycosuria, osteomalacia; and hypersensitivity such as scarlatiniform rash, morbilliform rash, Stevens-Johnson syndrome, systemic lupus erythematosus, and hepatic necrosis; and hematological reactions such as redcell aplasia, agranulocytosis, thrombocytopenia, aplastic anemia, and megaloblastic anemia *The Merck Manual of Medical Information* 345-350 (R. Berkow ed., 1997).

A seizure is the result of abnormal electrical discharge in the brain. The discharge can involve a small area of the brain and lead to the person only noticing an odd taste or smell or it can involve a large area of the brain and lead to convulsions, i.e., a seizure that causes jerking and spasms of the muscles throughout the body. Convulsions can also result in brief attacks of altered consciousness and loss of consciousness, muscle control, or bladder control. A seizures is often preceded by auras, i.e., unusual sensations of smell, taste, or vision or an intense feeling that a seizure is about to begin. A seizure typically lasts for about 2 to 5 minutes. When the seizure ends the person can have headache, sore muscles, unusual sensations, confusion, and profound fatigue (postictal state). Usually the person cannot remember what happened during the seizure.

A stroke or cerebrovascular accident, is the death of brain tissue (cerebral infarction) resulting from the lack of blood flow and insufficient oxygen to the brain. A stroke can be either ischemic or hemorrhagic. In an ischemic stroke, blood supply to the brain is cut off because of athersclerosis or a blood clot that has blocked a blood vessel. In a hemorrhagic stroke, a blood vessel bursts preventing normal blood flow and allowing blood to leak into an area of the brain and destroying it. Most strokes develop rapidly and cause brain damage within minutes. In some cases, however, strokes can continue to worsen for several hours or days. Symptoms of strokes vary depending on what part of the brain is effected. Symptoms include loss or abnormal sensations in an arm or leg or one side of the body, weakness or paralysis of an arm or leg or one side of the body, partial loss of vison or hearing, double vision, dizziness, slurred speech, difficulty in thinking of the appropriate word or saying it, inability to recognize parts of the body, unusual movements, loss of bladder control, imbalance, and falling, and fainting. The symptoms can be permanent and can be associated with coma or stupor. Strokes can cause edema or swelling of the brain which can further damage brain tissue. For persons suffering from a stroke, intensive rehabilitation can help overcome the disability caused by impairment of brain tissue. Rehabilitation trains other parts of the brain to assume the tasks previously performed by the damaged part.

Examples of drugs for treating strokes include anticoagulants such as heparin, drugs that break up clots such as streptokinase or tissue plasminogen activator, and drugs that reduce swelling such as mannitol or corticosteroids. *The Merck Manual of Medical Information* 352-355 (R. Berkow ed., 1997).

Pruritus is an unpleasant sensation that prompts scratching. Pruritus can be attributed to dry skin, scabies, dermatitis, herpetiformis, atopic dermatitis, pruritus vulvae et ani, miliaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, and fiberglass dermatitis. Conventionally, pruritus is treated by phototherapy with ultraviolet B or PUVA or with therapeutic agents such as naltrexone, nalmefene, danazol, tricyclics, and antidepressants.

Selective antagonists of the metabotropic glutamate receptor 5 ("mGluR5") have been shown to exert analgesic activity in in vivo animal models (K. Walker et al., *Neuropharmacology* 40:1-9 (2000) and A. Dogrul et al., *Neuroscience Letters,* 292(2):115-118 (2000)).

Selective antagonists of the mGluR5 receptor have also been shown to exert anxiolytic and anti-depressant activity in in vivo animal models (E. Tatarczynska et al., *Br. J. Pharmacol.* 132(7):1423-1430 (2001) and P. J. M. Will et al., *Trends in Pharmacological Sciences* 22(7):331-37 (2001)).

Selective antagonists of the mGluR5 receptor have also been shown to exert anti-Parkinson activity in vivo (K. J. Ossowska et al., *Neuropharmacology* 41(4):413-20 (2001) and P. J. M. Will et al., *Trends in Pharmacological Sciences* 22(7):331-37 (2001)).

Selective antagonists of the mGluR5 receptor have also been shown to exert anti-dependence activity in vivo (C. Chiamulera et al., *Nature Neuroscience* 4(9):873-74 (2001)).

International publication no. WO 02/08221 describes diaryl piperazine compounds and related compounds useful as selective modulators of capsaicin receptors and useful in the treatment of chronic and acute pain conditions, itch, and urinary incontinence.

International publication no. WO 99/37304 describes substituted oxoazaheterocycly compounds useful for inhibiting factor Xa.

U.S. Pat. No. 6,124,299 to Baindur et al. describes piperazine compounds that are useful as calcitonin mimetics.

International publication no. WO 02/16318 describes urea and thiourea compounds that are modulators of the vanilloid receptor.

International publication no. WO 98/25167 describes aryl piperazine compounds that are modulators of chemokine receptors.

U.S. Pat. No. 5,922,872 to Cook et al. describes meta-benzylic and alpha-amido compounds that are useful as antibacterials.

There remains, however, a clear need in the art for new drugs useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression.

Citation of any reference in Section 2 of this application is not to be construed as an admission that such reference is prior art to the present application.

3. SUMMARY OF THE INVENTION

The present invention encompasses compounds having the formula (I):

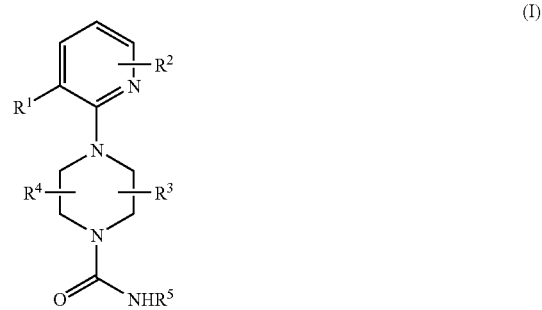

and pharmaceutically acceptable salts thereof, wherein:
R₁ is methyl or halo;

$R^2$ is:
(a) —$(C_2-C_6)$alkyl, —$(C_2-C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —$NO_2$, —CH=$NR^6$, or —$NR^6$OH;
(b) —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6$OH; or
(c) —H, -halo, —$NO_2$, —CN, or —$NH_2$;
$R^3$ is:
(a) —$(C_1-C_6)$alkyl, —$(C_2-C_6)$alkenyl, —$(C_2-C_6)$alkynyl, —$(CH_2)_nOR^6$, which is unsubstituted or substituted with one or more of —CN, —OH, -halo, —$NO_2$, —CH=$NR^6$, or —$NR^6$OH; or
(b) —H, -halo, —$NO_2$, —CN, or —$NH_2$;
$R^4$ is —H;
$R^5$ is:
(a) —$(C_1-C_6)$alkyl, —$(C_2-C_6)$alkenyl, or —$(C_2-C_6)$alkynyl; or
(b) —$(C_3-C_8)$cycloalkyl, —$(C_5-C_8)$cycloalkenyl, —$(C_6)$aryl, —$(C_{10})$aryl, —$(C_{14})$aryl, —$(C_3-C_7)$heterocycle, —$(C_1-C_6)$alkyl$(C_6)$aryl, —$(C_1-C_6)$alkyl$(C_{10})$aryl, —$(C_1-C_6)$alkyl$(C_{14})$aryl, —$(C_1-C_6)$alkyl$(C_3-C_7)$heterocycle, —$(C_2-C_6)$alkenyl$(C_6)$aryl, —$(C_2-C_6)$alkenyl$(C_{10})$aryl, —$(C_2-C_6)$alkenyl$(C_{14})$aryl, —$(C_2-C_6)$alkenyl$(C_3-C_7)$heterocycle, —$(C_2-C_6)$alkynyl$(C_3-C_8)$cycloalkyl, —$(C_2-C_6)$alkynyl$(C_5-C_8)$cycloalkenyl, —$(C_2-C_6)$alkynyl$(C_6)$aryl, —$(C_2-C_6)$alkynyl$(C_{10})$aryl, —$(C_2-C_6)$alkynyl$(C_{14})$aryl, or —$(C_2-C_6)$alkynyl$(C_3-C_7)$heterocycle, which is unsubstituted or substituted with one or more $R^7$ groups;
each $R^6$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_6)$aryl, —$(C_3-C_5)$heterocycle, C(halo)$_3$, or CH(halo)$_2$;
each $R^7$ is independently —$(C_1-C_6)$alkyl, —$(C_2-C_6)$alkenyl, —$(C_2-C_6)$alkynyl, —$(CH_2)_n(C_3-C_8)$cycloalkyl, —$(CH_2)$—$(C_5-C_8)$cycloalkenyl, —$(CH_2)_n(C_6)$aryl, —$(CH_2)_nSR^6$, —$(CH_2)_nCH(halo)_2$, —$(CH_2)_nC(halo)_3$, -halo, —$(CH_2)_nOR^6$; and
n is an integer ranging from 0 to 2.

The present invention also encompasses compounds having the formula (II):

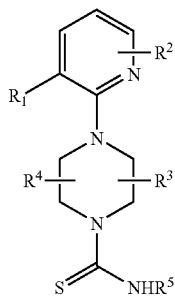

(II)

and pharmaceutically acceptable salts thereof, wherein:
$R_1$ is methyl or halo;
$R^2$ is:
(a) —$(C_2-C_6)$alkyl, —$(C_2-C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —$NO_2$, —CH=$NR^6$, or —$NR^6$OH;
(b) —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6$OH; or
(c) —H, -halo, —$NO_2$, —CN, or —$NH_2$;
$R^3$ is:
(a) —$(C_1-C_6)$alkyl, —$(C_2-C_6)$alkenyl, —$(C_2-C_6)$alkynyl, —$(CH_2)_nOR^6$, which is unsubstituted or substituted with one or more of —CN, —OH, -halo, —$NO_2$, —CH=$NR^6$, or —$NR^6$OH; or
(b) —H, -halo, —$NO_2$, —CN, or —$NH_2$;
$R^4$ is —H;
$R^5$ is:
(a) —$(C_1-C_6)$alkyl, —$(C_2-C_6)$alkenyl, or —$(C_2-C_6)$alkynyl; or
(b) —$(C_3-C_8)$cycloalkyl, —$(C_5-C_8)$cycloalkenyl, —$(C_6)$aryl, —$(C_{10})$aryl, —$(C_{14})$aryl, —$(C_3-C_7)$heterocycle, —$(C_1-C_6)$alkyl$(C_6)$aryl, —$(C_1-C_6)$alkyl$(C_{10})$aryl, —$(C_1-C_6)$alkyl$(C_{14})$aryl, —$(C_1-C_6)$alkyl$(C_3-C_7)$heterocycle, —$(C_2-C_6)$alkenyl$(C_6)$aryl, —$(C_2-C_6)$alkenyl$(C_{10})$aryl, —$(C_2-C_6)$alkenyl$(C_{14})$aryl, —$(C_2-C_6)$alkenyl$(C_3-C_7)$heterocycle, —$(C_2-C_6)$alkynyl$(C_3-C_8)$cycloalkyl, —$(C_2-C_6)$alkynyl$(C_5-C_8)$cycloalkenyl, —$(C_2-C_6)$alkynyl$(C_6)$aryl, —$(C_2-C_6)$alkynyl$(C_{10})$aryl, —$(C_2-C_6)$alkynyl$(C_{14})$aryl, or —$(C_2-C_6)$alkynyl$(C_3-C_7)$heterocycle, which is unsubstituted or substituted with one or more $R^7$ groups;
each $R^6$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_6)$aryl, —$(C_3-C_5)$heterocycle, C(halo)$_3$, or CH(halo)$_2$;
each $R^7$ is independently —$(C_1-C_6)$alkyl, —$(C_2-C_6)$alkenyl, —$(C_2-C_6)$alkynyl, —$(CH_2)_n(C_3-C_8)$cycloalkyl, —$(CH_2)$—$(C_5-C_8)$cycloalkenyl, —$(CH_2)_n(C_6)$aryl, —$(CH_2)_nSR^6$, —$(CH_2)_nCH(halo)_2$, —$(CH_2)_nC(halo)_3$, -halo, —$(CH_2)_nOR^6$; and
n is an integer ranging from 0 to 2.

The present invention also encompasses compounds having the formula (III):

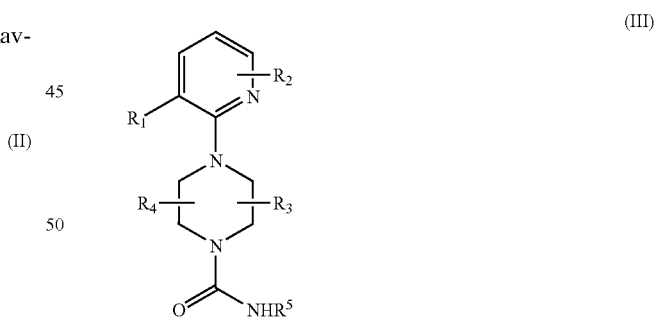

(III)

and pharmaceutically acceptable salts thereof, wherein:
$R_1$ is halo;
$R^2$ is:
(a) —$(C_2-C_6)$alkyl, —$(C_2-C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —$NO_2$, —CH=$NR^6$, or —$NR^6$OH;
(b) —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6$OH; or
(c) —H, -halo, —$NO_2$, —CN, or —$NH_2$;

$R^3$ is:
(a) —$(C_1-C_6)$alkyl, —$(C_2-C_6)$alkenyl, —$(C_2-C_6)$alkynyl, —$(CH_2)_nOR^6$, which is unsubstituted or substituted with one or more of —CN, —OH, -halo, —$NO_2$, —CH=$NR^6$, or —$NR^6$OH; or
(b) —H, -halo, —$NO_2$, —CN, or —$NH_2$;

$R^4$ is —H;

$R^5$ is:
(a) —$(C_1-C_6)$alkyl, —$(C_2-C_6)$alkenyl, or —$(C_2-C_6)$alkynyl; or
(b) —$(C_3-C_8)$cycloalkyl, —$(C_5-C_8)$cycloalkenyl, —$(C_6)$aryl, —$(C_{10})$aryl, —$(C_{14})$aryl, —$(C_3-C_7)$heterocycle, —$(C_1-C_6)$alkyl$(C_6)$aryl, —$(C_1-C_6)$alkyl$(C_{10})$aryl, —$(C_1-C_6)$alkyl$(C_{14})$aryl, —$(C_1-C_6)$alkyl$(C_3-C_7)$heterocycle, —$(C_2-C_6)$alkenyl$(C_6)$aryl, —$(C_2-C_6)$alkenyl$(C_{10})$aryl, —$(C_2-C_6)$alkenyl$(C_{14})$aryl, —$(C_2-C_6)$alkenyl$(C_3-C_7)$heterocycle, —$(C_2-C_6)$alkynyl$(C_3-C_8)$cycloalkyl, —$(C_2-C_6)$alkynyl$(C_5-C_8)$cycloalkenyl, —$(C_2-C_6)$alkynyl$(C_6)$aryl, —$(C_2-C_6)$alkynyl$(C_{10})$aryl, —$(C_2-C_6)$alkynyl$(C_{14})$aryl, or —$(C_2-C_6)$alkynyl$(C_3-C_7)$heterocycle, which is unsubstituted or substituted with one or more $R^7$ groups;

each $R^6$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_6)$aryl, —$(C_3-C_5)$heterocycle, C(halo)$_3$, or CH(halo)$_2$;

each $R^7$ is independently —$(C_2-C_6)$alkenyl, —$(C_2-C_6)$alkynyl, —$(CH_2)_n(C_3-C_8)$cycloalkyl, —$(CH_2)_n(C_5-C_8)$cycloalkenyl, —$(CH_2)_n(C_6)$aryl, —$(CH_2)_nSR^6$, —$(CH_2)_nCH(halo)_2$, —$(CH_2)_nC(halo)_3$, -halo, —$(CH_2)_nOR^6$; and n is an integer ranging from 0 to 2.

The present invention also encompasses compounds having the formula (IV):

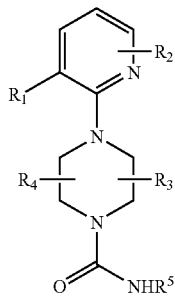

(IV)

and pharmaceutically acceptable salts thereof, wherein:
$R_1$ is methyl or halo;
$R^2$ is:
(a) —$(C_2-C_6)$alkyl, —$(C_2-C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —$NO_2$, —CH=$NR^6$, or —$NR^6$OH;
(b) —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6$OH; or
(c) —H, -halo, —$NO_2$, —CN, or —$NH_2$;

$R^3$ is:
(a) —$(C_2-C_6)$alkenyl, —$(C_2-C_6)$alkynyl, —$(CH_2)_nOR^6$, which is unsubstituted or substituted with one or more of —CN, —OH, -halo, —$NO_2$, —CH=$NR^6$, or —$NR^6$OH; or
(b) —H, -halo, —$NO_2$, —CN, or —$NH_2$;

$R^4$ is —H;

$R^5$ is:
(a) —$(C_1-C_6)$alkyl, —$(C_2-C_6)$alkenyl, or —$(C_2-C_6)$alkynyl; or
(b) —$(C_{10})$aryl, —$(C_{14})$aryl, —$(C_3-C_7)$heterocycle, —$(C_1-C_6)$alkyl$(C_6)$aryl, —$(C_1-C_6)$alkyl$(C_{10})$aryl, —$(C_1-C_6)$alkyl$(C_{14})$aryl, —$(C_1-C_6)$alkyl$(C_3-C_7)$heterocycle, —$(C_2-C_6)$alkenyl$(C_6)$aryl, —$(C_2-C_6)$alkenyl$(C_{10})$aryl, —$(C_2-C_6)$alkenyl$(C_{14})$aryl, —$(C_2-C_6)$alkenyl$(C_3-C_7)$heterocycle, —$(C_2-C_6)$alkyl$(C_3-C_8)$cycloalkyl, —$(C_2-C_6)$alkynyl$(C_5-C_8)$cycloalkenyl, —$(C_2-C_6)$alkynyl$(C_6)$aryl, —$(C_2-C_6)$alkynyl$(C_{10})$aryl, —$(C_2-C_6)$alkynyl$(C_{14})$aryl, or —$(C_2-C_6)$alkynyl$(C_3-C_7)$heterocycle, which is unsubstituted or substituted with one or more $R^7$ groups; or
(c) —$(C_6)$aryl, optionally substituted with one or more —$(C_2-C_6)$alkenyl, —$(C_2-C_6)$alkynyl, —$(CH_2)_n(C_3-C_8)$cycloalkyl, —$(CH_2)_n(C_5-C_8)$cycloalkenyl, —$(CH_2)_n(C_6)$aryl, —$(CH_2)_nSR^6$, —$(CH_2)_nCH(halo)_2$, —$(CH_2)_nC(halo)_3$, -halo or —$(CH_2)_nOR^6$ groups;

each $R^6$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_6)$aryl, —$(C_3-C_5)$heterocycle, C(halo)$_3$, or CH(halo)$_2$;

each $R^7$ is independently —$(C_1-C_6)$alkyl, —$(C_2-C_6)$alkenyl, —$(C_2-C_6)$alkynyl, —$(CH_2)_n(C_3-C_8)$cycloalkyl, —$(CH_2)_n(C_5-C_8)$cycloalkenyl, —$(CH_2)_n(C_6)$aryl, —$(CH_2)_nSR^6$, —$(CH_2)_nCH(halo)_2$, —$(CH_2)_nC(halo)_3$, -halo, —$(CH_2)_nOR^6$; and n is an integer ranging from 0 to 2.

The present invention also encompasses compounds having the formula (V):

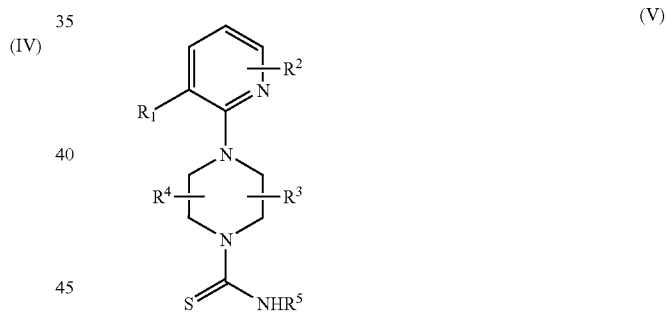

(V)

and pharmaceutically acceptable salts thereof, wherein:
$R_1$ is methyl or halo;
$R^2$ is:
(a) —$(C_2-C_6)$alkyl, —$(C_2-C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —$NO_2$, —CH=$NR^6$, or —$NR^6$OH;
(b) —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6$OH; or
(c) —H, -halo, —$NO_2$, —CN, or —$NH_2$;

$R^3$ is:
(a) —$(C_1-C_6)$alkyl, —$(C_2-C_6)$alkenyl, —$(C_2-C_6)$alkynyl, —$(CH_2)_nOR^6$, which is unsubstituted or substituted with one or more of —CN, —OH, -halo, —$NO_2$, —CH=$NR^6$, or —$NR^6$OH; or
(b) —H, -halo, —$NO_2$, —CN, or —$NH_2$;

$R^4$ is —H;

R⁵ is:
(a) —(C₁-C₆)alkyl, —(C₂-C₆)alkenyl, or —(C₂-C₆)alkynyl; or
(b) —(C₃-C₈)cycloalkyl, —(C₅-C₈)cycloalkenyl, —(C₁₀)aryl, —(C₁₄)aryl, —(C₃-C₇)heterocycle, —(C₁-C₆)alkyl(C₆)aryl, —(C₁-C₆)alkyl(C₁₀)aryl, —(C₁-C₆)alkyl(C₁₄)aryl, —(C₁-C₆)alkyl(C₃-C₇)heterocycle, —(C₂-C₆)alkenyl(C₆)aryl, —(C₂-C₆)alkenyl(C₁₀)aryl, —(C₂-C₆)alkenyl(C₁₄)aryl, —(C₂-C₆)alkenyl(C₃₋₇)heterocycle, —(C₂-C₆)alkynyl(C₃-C₈)cycloalkyl, —(C₂-C₆)alkynyl(C₅-C₈)cycloalkenyl, —(C₂-C₆)alkynyl(C₆)aryl, —(C₂-C₆)alkynyl(C₁₀)aryl, —(C₂-C₆)alkynyl(C₁₄)aryl, or —(C₂-C₆)alkynyl(C₃-C₇)heterocycle, which is unsubstituted or substituted with one or more R⁷ groups; or
(c) —(C₆)aryl, optionally substituted with one or more of —(C₂-C₆)alkenyl, —(C₂-C₆)alkynyl, —(CH₂)ₙ(C₃-C₈)cycloalkyl, —(CH₂)ₙ(C₅-C₈)cycloalkenyl, —(CH₂)ₙ(C₆)aryl, —(CH₂)ₙSR⁶, —(CH₂)ₙCH(halo)₂, —(CH₂)ₘC(halo)₃, -halo, —(CH₂)ₙOR⁶;

each R⁶ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, —(C₆)aryl, —(C₃-C₅)heterocycle, —C(halo)₃, or CH(halo)₂;

each R⁷ is independently —(C₁-C₆)alkyl, —(C₂-C₆)alkenyl, —(C₂-C₆)alkynyl, —(CH₂)ₙ(C₃-C₈)cycloalkyl, —(CH₂)ₙ(C₅-C₈)cycloalkenyl, —(CH₂)ₙ(C₆)aryl, —(CH₂)ₙSR⁶, —(CH₂)ₙCH(halo)₂, —(CH₂)ₙC(halo)₃, -halo, —(CH₂)ₙOR⁶;

n is an integer ranging from 0 to 2.

The present invention also encompasses compounds having the formula (VI):

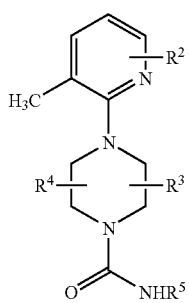

(VI)

and pharmaceutically acceptable salts thereof, wherein:
R² is:
(a) —(C₂-C₆)alkyl, —(C₂-C₃)alkenyl, —(CH₂)ₙC(O)R⁶, —(CH₂)ₙOR⁶, —(CH₂)ₙSR⁶, which is unsubstituted or substituted with one or more of —CN, —OH, -halo, —NO₂, —CH=NR⁶, or —NR⁶OH;
(b) —CH₃, —CH₂F, or —CHF₂, which is unsubstituted or substituted with one or more of —CN, —OH, —Cl, —Br, —I, —NO₂, —CH=NR⁶, or —NR⁶OH; or
(c) —H, -halo, —NO₂, —CN, or —NH₂;
R³ is:
(a) —(C₁-C₆)alkyl, —(C₂-C₆)alkenyl, —(C₂-C₆)alkynyl, —(CH₂)ₙOR⁶, which is unsubstituted or substituted with one or more of —CN, —OH, -halo, —NO₂, —CH=NR⁶, or —NR⁶OH; or
(b) —H, -halo, —NO₂, —CN, or —NH₂;
R⁴ is —H;

R⁵ is:
(a) —(C₁-C₆)alkyl, —(C₂-C₆)alkenyl, or —(C₂-C₆)alkynyl; or
(b) —(C₃-C₈)cycloalkyl, —(C₅-C₈)cycloalkenyl, —(C₁₀)aryl, —(C₁₄)aryl, —(C₃-C₇)heterocycle, —(C₁-C₆)alkyl(C₆)aryl, —(C₁-C₆)alkyl(C₁₀)aryl, —(C₁-C₆)alkyl(C₁₄)aryl, —(C₁-C₆)alkyl(C₃-C₇)heterocycle, —(C₂-C₆)alkenyl(C₆)aryl, —(C₂-C₆)alkenyl(C₁₀)aryl, —(C₂-C₆)alkenyl(C₁₄)aryl, —(C₂-C₆)alkenyl(C₃₋₇)heterocycle, —(C₂-C₆)alkynyl(C₃-C₈)cycloalkyl, —(C₂-C₆)alkynyl(C₅-C₈)cycloalkenyl, —(C₂-C₆)alkynyl(C₆)aryl, —(C₂-C₆)alkynyl(C₁₀)aryl, —(C₂-C₆)alkynyl(C₁₄)aryl, or —(C₂-C₆)alkynyl(C₃-C₇)heterocycle, which is unsubstituted or substituted with one or more R⁷ groups; or
(c) —(C₆)aryl, optionally substituted with one or more (C₂-C₆)alkenyl, —(C₂-C₆)alkynyl, —(CH₂)ₙ(C₃-C₈)cycloalkyl, —(CH₂)ₙ(C₅-C₈)cycloalkenyl, —(CH₂)ₙ(C₆)aryl, —(CH₂)ₙSR⁶, —(CH₂)ₙCH(halo)₂, —(CH₂)ₙC(halo)₃, -halo or —(CH₂)ₙOR⁶ groups;

each R⁶ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, —(C₆)aryl, —(C₃-C₅)heterocycle, C(halo)₃, or CH(halo)₂;

each R⁷ is independently —(C₁-C₆)alkyl, —(C₂-C₆)alkenyl, —(C₂-C₆)alkynyl, —(CH₂)ₙ(C₃-C₈)cycloalkyl, —(CH₂)ₙ(C₅-C₈)cycloalkenyl, —(CH₂)ₙ(C₆)aryl, —(CH₂)ₙSR⁶, —(CH₂)ₙCH(halo)₂, —(CH₂)ₙC(halo)₃, -halo, —(CH₂)ₙOR⁶; and n is an integer ranging from 0 to 2.

The present invention also encompasses compounds having the formula (VII):

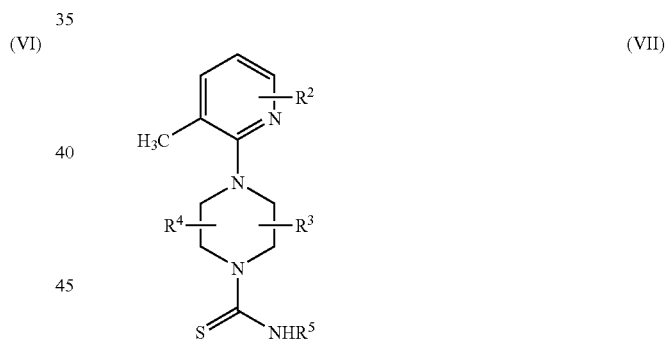

(VII)

and pharmaceutically acceptable salts thereof, wherein:
R² is:
(a) —(C₂-C₆)alkyl, —(C₂-C₃)alkenyl, —(CH₂)ₙC(O)R⁶, —(CH₂)ₙOR⁶, —(CH₂)ₙSR⁶, which is unsubstituted or substituted with one or more of —CN, —OH, -halo, —NO₂, —CH=NR⁶, or —NR⁶OH;
(b) —CH₃, —CH₂F, or —CHF₂, which is unsubstituted or substituted with one or more of —CN, —OH, —Cl, —Br, —I, —NO₂, —CH=NR⁶, or —NR⁶OH; or
(c) —H, -halo, —NO₂, —CN, or —NH₂;
R³ is:
(a) —(C₁-C₆)alkyl, —(C₂-C₆)alkenyl, —(C₂-C₆)alkynyl, —(CH₂)ₙOR⁶, which is unsubstituted or substituted with one or more of —CN, —OH, -halo, —NO₂, —CH=NR⁶, or —NR⁶OH; or
(b) —H, -halo, —NO₂, —CN, or —NH₂;
R⁴ is —H;

$R^5$ is:
(a) —$(C_1-C_6)$alkyl, —$(C_2-C_6)$alkenyl, or —$(C_2-C_6)$alkynyl; or
(b) —$(C_3-C_8)$cycloalkyl, —$(C_5-C_8)$cycloalkenyl, —$(C_6)$aryl, —$(C_{10})$aryl, —$(C_{14})$aryl, —$(C_3-C_7)$heterocycle, —$(C_1-C_6)$alkyl$(C_6)$aryl, —$(C_1-C_6)$alkyl$(C_{10})$aryl, —$(C_1-C_6)$alkyl$(C_{14})$aryl, —$(C_1-C_6)$alkyl$(C_3-C_7)$heterocycle, —$(C_2-C_6)$alkenyl$(C_6)$aryl, —$(C_2-C_6)$alkenyl$(C_{10})$aryl, —$(C_2-C_6)$alkenyl$(C_{14})$aryl, —$(C_2-C_6)$alkenyl$(C_3-C_7)$heterocycle, —$(C_2-C_6)$alkynyl$(C_3-C_8)$cycloalkyl, —$(C_2-C_6)$alkynyl$(C_5-C_8)$cycloalkenyl, —$(C_2-C_6)$alkynyl$(C_6)$aryl, —$(C_2-C_6)$alkynyl$(C_{10})$aryl, —$(C_2-C_6)$alkynyl$(C_{14})$aryl, or —$(C_2-C_6)$alkynyl$(C_3-C_7)$heterocycle, which is unsubstituted or substituted with one or more $R^7$ groups;

each $R^6$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, —$(C_6)$aryl, —$(C_3-C_5)$heterocycle, C(halo)$_3$, or CH(halo)$_2$;

each $R^7$ is independently —$(C_1-C_6)$alkyl, —$(C_2-C_6)$alkenyl, —$(C_2-C_6)$alkynyl, —$(CH_2)_n(C_3-C_8)$cycloalkyl, —$(CH_2)$—$(C_5-C_8)$cycloalkenyl, —$(CH_2)_n(C_6)$aryl, —$(CH_2)_n SR^6$, —$(CH_2)_n CH(halo)_2$, —$(CH_2)_n C(halo)_3$, -halo, —$(CH_2)_n OR^6$; and n is an integer ranging from 0 to 2.

The present invention also encompasses compounds having the formula (VIII):

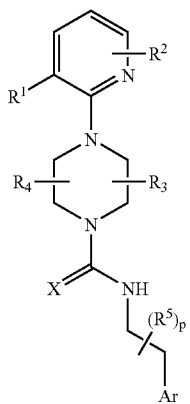

(VIII)

and pharmaceutically acceptable salts thereof, wherein:
X is O or S;
$R^1$ is —$CH_3$ or -halo;
$R^2$ is:
(a) —$(C_2-C_6)$alkyl, —$(C_2-C_3)$alkenyl, —$(CH_2)_n C(O)R^6$, —$(CH_2)_n OR^6$, —$(CH_2)_n SR^6$, which is unsubstituted or substituted with one or more of —CN, —OH, -halo, —NO$_2$, —CH=NR$^6$, or —NR$^6$OH;
(b) —$CH_3$, —$CH_2F$, or —$CHF_2$, which is unsubstituted or substituted with one or more of —CN, —OH, —Cl, —Br, —I, —NO$_2$, —CH=NR$^6$, or —NR$^6$OH; or
(c) —H, -halo, —NO$_2$, —CN, or —NH$_2$;
$R^3$ is:
(a) —$(C_1-C_6)$alkyl, —$(C_2-C_6)$alkenyl, —$(C_2-C_6)$alkynyl, —$(CH_2)_n OR^6$, which is unsubstituted or substituted with one or more of —CN, —OH, -halo, —NO$_2$, —CH=NR$^6$, or —NR$^6$OH; or
(b) —H, -halo, —NO$_2$, —CN, or —NH$_2$;
$R^4$ is —H;

Ar is —$(C_6)$aryl, —$(C_{10})$aryl, —$(C_{14})$aryl, —$(C_3-C_8)$cycloalkyl or —$(C_5-C_8)$cycloalkenyl, which is unsubstituted or substituted with one or more $R^7$ groups;

each $R^5$ is independently —$(C_1-C_6)$alkyl, —$(C_2-C_6)$alkenyl, —$(C_2-C_6)$alkynyl, —$(CH_2)_n(C_3-C_8)$cycloalkyl, —$(CH_2)_n(C_5-C_8)$cycloalkenyl, —$(CH_2)_n(C_6)$aryl, —$(CH_2)_n SR^6$, —$(CH_2)_n CH(halo)_2$, —$(CH_2)_n C(halo)_3$, -halo, —$(CH_2)_n OR^6$;

each $R^6$ is independently —$(C_1-C_6)$alkyl, —$(C_2-C_6)$alkenyl, —$(C_2-C_6)$alkynyl, —$(C_6)$aryl, —$(C_{10})$aryl, or —$(C_{14})$aryl;

each $R^7$ is independently —$(C_1-C_6)$alkyl, —$(C_2-C_6)$alkenyl, —$(C_2-C_6)$alkynyl, —$(CH_2)_n(C_3-C_8)$cycloalkyl, —$(CH_2)_n(C_5-C_8)$cycloalkenyl, —$(CH_2)_n(C_6)$aryl, —$(CH_2)_n SR^6$, —$(CH_2)_n CH(halo)_2$, —$(CH_2)_n C(halo)_3$, -halo, —$(CH_2)_n OR^6$;

n is an integer ranging from 0 to 2; and
p is an integer ranging from 0 to 2.

The present invention also encompasses compounds having the formula (IX):

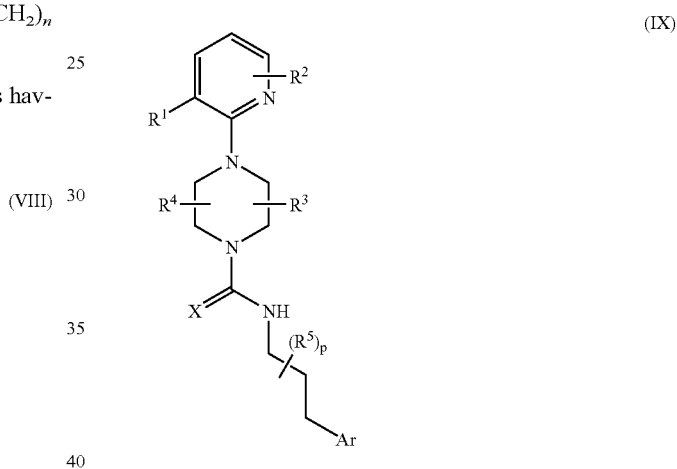

(IX)

and pharmaceutically acceptable salts thereof, wherein:
X is O or S;
$R^1$ is —$CH_3$ or -halo;
$R^2$ is:
(a) —$(C_2-C_6)$alkyl, —$(C_2-C_3)$alkenyl, —$(CH_2)_n C(O)R^6$, —$(CH_2)_n OR^6$, —$(CH_2)_n SR^6$, which is unsubstituted or substituted with one or more of —CN, —OH, -halo, —NO$_2$, —CH=NR$^6$, or —NR$^6$OH;
(b) —$CH_3$, —$CH_2F$, or —$CHF_2$, which is unsubstituted or substituted with one or more of —CN, —OH, —Cl, —Br, —I, —NO$_2$, —CH=NR$^6$, or —NR$^6$OH; or
(c) —H, -halo, —NO$_2$, —CN, or —NH$_2$;
$R^3$ is:
(a) —$(C_1-C_6)$alkyl, —$(C_2-C_6)$alkenyl, —$(C_2-C_6)$alkynyl, —$(CH_2)_n OR^6$, which is unsubstituted or substituted with one or more of —CN, —OH, -halo, —NO$_2$, —CH=NR$^6$, or —NR$^6$OH; or
(b) —H, -halo, —NO$_2$, —CN, or —NH$_2$;
Ar is —$(C_6)$aryl, —$(C_{10})$aryl, —$(C_{14})$aryl, —$(C_3-C_8)$cycloalkyl or —$(C_5-C_8)$cycloalkenyl, which is unsubstituted or substituted with one or more $R^7$ groups;
$R^4$ is —H;
each $R^5$ is independently —$(C_1-C_6)$alkyl, —$(C_2-C_6)$alkenyl, —$(C_2-C_6)$alkynyl, —$(CH_2)_n(C_3-C_8)$cycloalkyl, —(CH$_2$)$_n$(C$_5$-C$_8$)cycloalkenyl, —(CH$_2$)$_n$(C$_6$)aryl, —(CH$_2$)$_n$SR$^6$, —(CH$_2$)$_n$CH(halo)$_2$, —(CH$_2$)$_n$C(halo)$_3$, -halo, —(CH$_2$)$_n$OR$^6$;

each R$^6$ is independently —(C$_1$-C$_6$)alkyl, —(C$_2$-C$_6$)alkenyl, —(C$_2$-C$_6$)alkynyl, —(C$_6$)aryl, —(C$_{10}$)aryl, or —(C$_{14}$)aryl;

each R$^7$ is independently —(C$_1$-C$_6$)alkyl, —(C$_2$-C$_6$)alkenyl, —(C$_2$-C$_6$)alkynyl, —(CH$_2$)$_n$(C$_3$-C$_8$)cycloalkyl, —(CH$_2$)$_n$(C$_5$-C$_8$)cycloalkenyl, —(CH$_2$)$_n$(C$_6$)aryl, —(CH$_2$)$_n$SR$^6$, —(CH$_2$)$_n$CH(halo)$_2$, —(CH$_2$)$_n$C(halo)$_3$, -halo, —(CH$_2$)$_n$OR$^6$;

n is an integer ranging from 0 to 2; and p is an integer ranging from 0 to 2.

A compound of formulas (I)-(IX) or a pharmaceutically acceptable salt thereof (a "Piperazine Compound") is useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal.

The invention also relates to compositions comprising an effective amount of a Piperazine Compound and a pharmaceutically acceptable carrier or excipient. The compositions are useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal.

The invention further relates to methods for treating pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression comprising administering to an animal in need thereof an effective amount of a Piperazine Compound.

The invention further relates to methods for preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression comprising administering to an animal in need thereof an effective amount of a Piperazine Compound.

The invention still further relates to methods for inhibiting Vanilloid Receptor 1 ("VR1") function in a cell, comprising contacting a cell capable of expressing VR1 with an effective amount of a Piperazine Compound.

The invention still further relates to methods for inhibiting mGluR5 function in a cell, comprising contacting a cell capable of expressing mGluR5 with an effective amount of a Piperazine Compound.

The invention still further relates to methods for inhibiting metabotropic glutamate receptor 1 ("mGluR1") function in a cell, comprising contacting a cell capable of expressing mGluR1 with an effective amount of a Piperazine Compound.

The invention still further relates to a method for preparing a composition comprising the step of admixing a Piperazine Compound and a pharmaceutically acceptable carrier or excipient.

The invention still further relates to a kit comprising a container containing an effective amount of a Piperazine Compound.

The present invention can be understood more fully by reference to the following detailed description and illustrative examples, which are intended to exemplify non-limiting embodiments of the invention.

4. DETAILED DESCRIPTION OF THE INVENTION

As stated above, the present invention encompasses compounds of Formula (I)

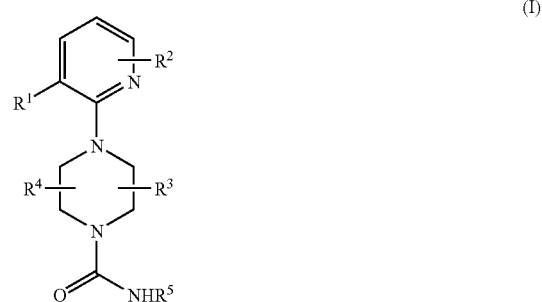

(I)

and pharmaceutically acceptable salts thereof, where R$^1$-R$^5$ are defined above.

In one embodiment, R$_1$ is methyl.

In another embodiment, R$_1$ is halo.

In another embodiment, R$_2$ is —(C$_2$-C$_6$)alkyl, —(C$_2$-C$_3$)alkenyl, —(CH$_2$)$_n$C(O)R$^6$, —(CH$_2$)$_n$OR$^6$, —(CH$_2$)$_n$SR$^6$, which is unsubstituted or substituted with one or more of —CN, —OH, -halo, —NO$_2$, —CH=NR$^6$, or —NR$^6$OH.

In another embodiment, R$_2$ is —CH$_3$, —CH$_2$F, or —CHF$_2$, which is unsubstituted or substituted with one or more of —CN, —OH, —Cl, —Br, —I, —NO$_2$, —CH=NR$^6$, or —NR$^6$OH.

In another embodiment, R$_2$ is —H, -halo, —NO$_2$, —CN, or —NH$_2$.

In another embodiment, R$_2$ is —H.

In another embodiment, R$^3$ is —(C$_1$-C$_6$)alkyl, —(C$_2$-C$_6$)alkenyl, —(C$_2$-C$_6$)alkynyl, —(CH$_2$)$_n$OR$^6$, which can be unsubstituted or substituted with one or more of —CN, —OH, -halo, —NO$_2$, —CH=NR$^6$, or —NR$^6$OH.

In another embodiment, R$^3$ is —H, -halo, —NO$_2$, —CN, or —NH$_2$.

In another embodiment, R$^3$ is —H.

In another embodiment, R$^3$ is —CH$_3$.

In another embodiment, R$^5$ is —(C$_2$-C$_6$)alkenyl, or —(C$_2$-C$_6$)alkynyl.

In another embodiment, R$^5$ is —(C$_3$-C$_8$)cycloalkyl, —(C$_5$-C$_8$)cycloalkenyl, —(C$_6$)aryl, —(C$_{10}$)aryl, —(C$_{14}$)aryl, —(C$_3$-C$_7$)heterocycle, —(C$_1$-C$_6$)alkyl(C$_6$)aryl, —(C$_1$-C$_6$)alkyl(C$_{10}$)aryl, —(C$_1$-C$_6$)alkyl(C$_{14}$)aryl, —(C$_1$-C$_6$)alkyl(C$_3$-C$_7$)heterocycle, —(C$_2$-C$_6$)alkenyl(C$_6$)aryl, —(C$_2$-C$_6$)alkenyl(C$_{10}$)aryl, —(C$_2$-C$_6$)alkenyl(C$_{14}$)aryl, —(C$_2$-C$_6$)alkenyl(C$_3$-C$_7$)heterocycle, —(C$_2$-C$_6$)alkynyl(C$_3$-C$_8$)cycloalkyl, —(C$_2$-C$_6$)alkynyl(C$_5$-C$_8$)cycloalkenyl, —(C$_2$-C$_6$)alkynyl(C$_6$)aryl, —(C$_2$-C$_6$)alkynyl(C$_{10}$)aryl, —(C$_2$-C$_6$)alkynyl(C$_{14}$)aryl, or —(C$_2$-C$_6$)alkynyl(C$_3$-C$_7$)heterocycle, which is unsubstituted or substituted with one or more R$^7$ groups.

In another embodiment, $R^5$ is phenyl optionally substituted with a —$(C_1-C_6)$ alkyl group. In another embodiment, the —$(C_1-C_6)$ alkyl group is substituted at the phenyl group's 4-position. In another embodiment, the —$(C_1-C_6)$ alkyl group is a t-butyl group.

In another embodiment, $R^1$ is methyl and $R^5$ is phenyl. In another embodiment, $R^1$ is methyl and $R^5$ is phenyl substituted with a —$(C_1-C_6)$ alkyl group. In another embodiment, $R^1$ is methyl and $R^5$ is phenyl substituted with a —$(C_1-C_6)$ alkyl group at the phenyl group's 4-position. In another embodiment, $R^1$ methyl and $R^5$ is phenyl substituted with a t-butyl group at the phenyl group's 4-position.

In another embodiment, $R^1$ is -halo and $R^5$ is phenyl. In another embodiment, $R^1$ is -halo and $R^5$ is phenyl substituted with a —$(C_1-C_6)$ alkyl group. In another embodiment, $R^1$-halo and $R^5$ is phenyl substituted with a —$(C_1-C_6)$ alkyl group at the phenyl group's 4-position. In another embodiment, $R^1$-halo and $R^5$ is phenyl substituted with a t-butyl group at the phenyl group's 4-position.

In another embodiment, $R^1$ is -chloro and $R^5$ is phenyl. In another embodiment, $R^1$ is -chloro and $R^5$ is phenyl substituted with a —$(C_1-C_6)$ alkyl group. In another embodiment, $R^1$-chloro and $R^5$ is phenyl substituted with a —$(C_1-C_6)$ alkyl group at the phenyl group's 4-position. In another embodiment, $R^1$-chloro and $R^5$ is phenyl substituted with a t-butyl group at the phenyl group's 4-position.

The present invention also encompasses compounds of Formula (II)

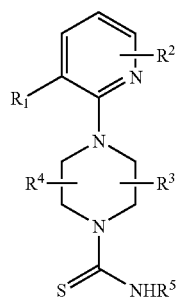

(II)

and pharmaceutically acceptable salts thereof, where $R^1$-$R^5$ are defined above.

In one embodiment, $R_1$ is methyl.

In another embodiment, $R_1$ is halo.

In another embodiment, $R_2$ is —$(C_2-C_6)$alkyl, —$(C_2-C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —$NO_2$, —CH=$NR^6$, or —$NR^6OH$.

In another embodiment, $R_2$ is —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6OH$.

In another embodiment, $R_2$ is —H, -halo, —$NO_2$, —CN, or —$NH_2$.

In another embodiment, $R_2$ is —H.

In another embodiment, $R^3$ is —$(C_1-C_6)$alkyl, —$(C_2-C_6)$alkenyl, —$(C_2-C_6)$alkynyl, —$(CH_2)_nOR^6$, which can be unsubstituted or substituted with one or more of —CN, —OH, -halo, —$NO_2$, —CH=$NR^6$, or —$NR^6OH$.

In another embodiment, $R^3$ is —H, -halo, —$NO_2$, —CN, or —$NH_2$.

In another embodiment, $R^3$ is —H.

In another embodiment, $R^3$ is —$CH_3$.

In another embodiment, $R^5$ is —$(C_1-C_6)$alkyl, —$(C_2-C_6)$alkenyl, or —$(C_2-C_6)$alkynyl.

In another embodiment, $R^5$ is —$(C_3-C_8)$cycloalkyl, —$(C_5-C_8)$cycloalkenyl, —$(C_6)$aryl, —$(C_{10})$aryl, —$(C_{14})$aryl, —$(C_3-C_7)$heterocycle, —$(C_1-C_6)$alkyl$(C_6)$aryl, —$(C_1-C_6)$alkyl$(C_{10})$aryl, —$(C_1-C_6)$alkyl$(C_{14})$aryl, —$(C_1-C_6)$alkyl$(C_3-C_7)$heterocycle, —$(C_2-C_6)$alkenyl$(C_6)$aryl, —$(C_2-C_6)$alkenyl$(C_{10})$aryl, —$(C_2-C_6)$alkenyl$(C_{14})$aryl, —$(C_2-C_6)$alkenyl$(C_3-C_7)$heterocycle, —$(C_2-C_6)$alkynyl$(C_3-C_8)$cycloalkyl, —$(C_2-C_6)$alkynyl$(C_5-C_8)$cycloalkenyl, —$(C_2-C_6)$alkynyl$(C_6)$aryl, —$(C_2-C_6)$alkynyl$(C_{10})$aryl, —$(C_2-C_6)$alkynyl$(C_{14})$aryl, or —$(C_2-C_6)$alkynyl$(C_3-C_7)$heterocycle, which is unsubstituted or substituted with one or more $R^7$ groups.

In another embodiment, $R^5$ is phenyl optionally substituted with a —$(C_1-C_6)$ alkyl group. In another embodiment, the —$(C_1-C_6)$ alkyl group is substituted at the phenyl group's 4-position. In another embodiment, the —$(C_1-C_6)$ alkyl group is a t-butyl group.

In another embodiment, $R^1$ is methyl and $R^5$ is phenyl. In another embodiment, $R^1$ is methyl and $R^5$ is phenyl substituted with a —$(C_1-C_6)$ alkyl group. In another embodiment, $R^1$ methyl and $R^5$ is phenyl substituted with a —$(C_1-C_6)$ alkyl group at the phenyl group's 4-position. In another embodiment, $R^1$ methyl and $R^5$ is phenyl substituted with a t-butyl group at the phenyl group's 4-position.

In another embodiment, $R^1$ is -halo and $R^5$ is phenyl. In another embodiment, $R^1$ is -halo and $R^5$ is phenyl substituted with a —$(C_1-C_6)$ alkyl group. In another embodiment, $R^1$-halo and $R^5$ is phenyl substituted with a —$(C_1-C_6)$ alkyl group at the phenyl group's 4-position. In another embodiment, $R^1$-halo and $R^5$ is phenyl substituted with a t-butyl group at the phenyl group's 4-position.

In another embodiment, $R^1$ is -chloro and $R^5$ is phenyl. In another embodiment, $R^1$ is -chloro and $R^5$ is phenyl substituted with a —$(C_1-C_6)$ alkyl group. In another embodiment, $R^1$-chloro and $R^5$ is phenyl substituted with a —$(C_1-C_6)$ alkyl group at the phenyl group's 4-position. In another embodiment, $R^1$-chloro and $R^5$ is phenyl substituted with a t-butyl group at the phenyl group's 4-position.

The present invention also encompasses compounds of Formula (III):

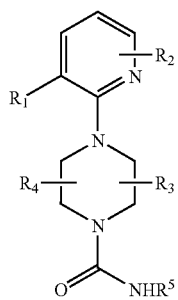

(III)

and pharmaceutically acceptable salts thereof, where $R^1$-$R^5$ are defined above. In a preferred embodiment, $R^5$ is phenyl.

In one embodiment $R^1$ is -chloro.

In another embodiment, $R^1$ is -bromo.

In another embodiment, $R^1$ is -iodo.

In another embodiment, $R^1$ is -fluoro.

In another embodiment, $R^2$ is —$(C_2-C_6)$alkyl, —$(C_2-C_3)$alkenyl, —$(CH)_nC(O)R^6$, $(CH_2)_nOR^6$, —$(CH_2)_nSR^6$, which is unsubstituted or substituted with one or more of —CN, —OH, -halo, —NO$_2$, —CH=NR$^6$, or —NR$^6$OH.

In another embodiment, R$^2$ is —CH$_3$, —CH$_2$F, or —CHF$_2$, which is unsubstituted or substituted with one or more of —CN, —OH, —Cl, —Br, —I, —NO$_2$, —CH=NR$^6$, or —NR$^6$OH.

In another embodiment, R$^2$ is —H, -halo, —NO$_2$, —CN, or —NH$_2$.

In another embodiment, R$_2$ is —H.

In another embodiment, R$^3$ is —(C$_1$-C$_6$)alkyl, —(C$_2$-C$_6$)alkenyl, —(C$_2$-C$_6$)alkynyl, —(CH$_2$)$_n$OR$^6$, which is unsubstituted or substituted with one or more of —CN, —OH, -halo, —NO$_2$, —CH=NR$^6$, or —NR$^6$OH.

In another embodiment, R$^3$ is —H, -halo, —NO$_2$, —CN, or —NH$_2$.

In another embodiment, R$^3$ is —H.

In another embodiment, R$^3$ is —CH$_3$.

In another embodiment, R$^5$ is —(C$_2$-C$_6$)alkenyl, or —(C$_2$-C$_6$)alkynyl.

In another embodiment, R$^5$ is —(C$_3$-C$_8$)cycloalkyl, —(C$_5$-C$_8$)cycloalkenyl, —(C$_6$)aryl, —(C$_{10}$)aryl, —(C$_{14}$)aryl, —(C$_3$-C$_7$)heterocycle, —(C$_1$-C$_6$)alkyl(C$_6$)aryl, —(C$_1$-C$_6$)alkyl(C$_{10}$)aryl, —(C$_1$-C$_6$)alkyl(C$_{14}$)aryl, —(C$_1$-C$_6$)alkyl(C$_3$-C$_7$)heterocycle, —(C$_2$-C$_6$)alkenyl(C$_6$)aryl, —(C$_2$-C$_6$)alkenyl(C$_{10}$)aryl, —(C$_2$-C$_6$)alkenyl(C$_{14}$)aryl, —(C$_2$-C$_6$)alkenyl(C$_3$-C$_7$)heterocycle, —(C$_2$-C$_6$)alkynyl(C$_3$-C$_8$)cycloalkyl, —(C$_2$-C$_6$)alkynyl(C$_5$-C$_8$)cycloalkenyl, —(C$_2$-C$_6$)alkynyl(C$_6$)aryl, —(C$_2$-C$_6$)alkynyl(C$_{10}$)aryl, —(C$_2$-C$_6$)alkynyl(C$_{14}$)aryl, or —(C$_2$-C$_6$)alkynyl(C$_3$-C$_7$)heterocycle, which is unsubstituted or substituted with one or more R$^7$ groups.

In another embodiment, R$^5$ is phenyl optionally substituted with a —(C$_1$-C$_6$) alkyl group. In another embodiment, the —(C$_1$-C$_6$) alkyl group is substituted at the phenyl group's 4-position. In another embodiment, the —(C$_1$-C$_6$) alkyl group is a t-butyl group.

In another embodiment, R$^1$ is -chloro and R$^5$ is phenyl. In another embodiment, R$^1$ is -chloro and R$^5$ is phenyl substituted with a —(C$_1$-C$_6$) alkyl group. In another embodiment, R$^1$-chloro and R$^5$ is phenyl substituted with a —(C$_1$-C$_6$) alkyl group at the phenyl group's 4-position. In another embodiment, R$^1$-chloro and R$^5$ is phenyl substituted with a t-butyl group at the phenyl group's 4-position.

In another embodiment, R$^1$ is -bromo and R$^5$ is phenyl. In another embodiment, R$^1$ is -bromo and R$^5$ is phenyl substituted with a —(C$_1$-C$_6$) alkyl group. In another embodiment, R$^1$-bromo and R$^5$ is phenyl substituted with a —(C$_1$-C$_6$) alkyl group at the phenyl group's 4-position. In another embodiment, R$^1$-bromo and R$^5$ is phenyl substituted with a t-butyl group at the phenyl group's 4-position.

In an another embodiment, R$^1$ is -iodo and R$^5$ is phenyl. In another embodiment, R$^1$ is -iodo and R$^5$ is phenyl substituted with a —(C$_1$-C$_6$) alkyl group. In another embodiment, R$^1$-iodo and R$^1$ is phenyl substituted with a —(C$_1$-C$_6$) alkyl group at the phenyl group's 4-position. In another embodiment, R$^1$-iodo and R$^5$ is phenyl substituted with a t-butyl group at the phenyl group's 4-position.

In another embodiment, R$^1$ is -fluoro and R$^5$ is phenyl. In another embodiment, R$^1$ is -fluoro and R$^5$ is phenyl substituted with a —(C$_1$-C$_6$) alkyl group. In another embodiment, R$^1$-fluoro and R$^5$ is phenyl substituted with a —(C$_1$-C$_6$) alkyl group at the phenyl group's 4-position. In another embodiment, R$^1$-fluoro and R$^5$ is phenyl substituted with a t-butyl group at the phenyl group's 4-position.

The present invention also encompasses compounds of Formula (IV):

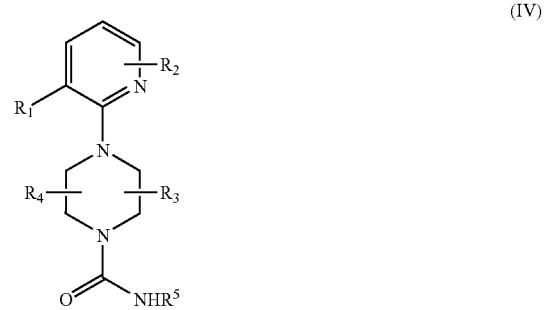

(IV)

and pharmaceutically acceptable salts thereof, where R$^1$-R$^5$ are defined above. In a preferred embodiment, R$^5$ is phenyl.

In one embodiment, R$_1$ is methyl.

In another embodiment, R$_1$ is halo.

In another embodiment R$^1$ is -chloro.

In another embodiment, R$^1$ is -bromo.

In another embodiment, R$^1$ is -iodo.

In another embodiment, R$^1$ is -fluoro.

In another embodiment, R$^2$ is —(C$_2$-C$_6$)alkyl, —(C$_2$-C$_3$)alkenyl, —(CH$_2$)$_n$C(O)R$^6$, —(CH$_2$)$_n$OR$^6$, —(CH$_2$)$_n$SR$^6$, which is unsubstituted or substituted with one or more of —CN, —OH, -halo, —NO$_2$, —CH=NR$^6$, or —NR$^6$OH;

In another embodiment, R$^2$ is —CH$_3$, —CH$_2$F, or —CHF$_2$, which is unsubstituted or substituted with one or more of —CN, —OH, —Cl, —Br, —I, —NO$_2$, —CH=NR$^6$, or —NR$^6$OH.

In another embodiment, R$^2$ is —H, -halo, —NO$_2$, —CN, or —NH$_2$.

In another embodiment, R$_2$ is —H.

In another embodiment, R$^3$ is —(C$_2$-C$_6$)alkenyl, —(C$_2$-C$_6$)alkynyl, —(CH$_2$)$_n$OR$^6$, which R$^3$ and R$^4$ are each independently unsubstituted or substituted with one or more of —CN, —OH, -halo, —NO$_2$, —CH=NR$^6$, or —NR$^6$OH.

In another embodiment, R$^3$ is —H, -halo, —NO$_2$, —CN, or —NH$_2$.

In another embodiment R$^3$ is —H.

In another embodiment, R$^3$ is —CH$_3$.

In another embodiment R$^5$ is —(C$_2$-C$_6$)alkenyl, or —(C$_2$-C$_6$)alkynyl.

In another embodiment R$^5$ is —(C$_{10}$)aryl, —(C$_{14}$)aryl, —(C$_3$-C$_7$)heterocycle, —(C$_1$-C$_6$)alkyl(C$_6$)aryl, —(C$_1$-C$_6$)alkyl(C$_{10}$)aryl, —(C$_1$-C$_6$)alkyl(C$_{14}$)aryl, —(C$_1$-C$_6$)alkyl(C$_3$-C$_7$)heterocycle, —(C$_2$-C$_6$)alkenyl(C$_6$)aryl, —(C$_2$-C$_6$)alkenyl(C$_{10}$)aryl, —(C$_2$-C$_6$)alkenyl(C$_{14}$)aryl, —(C$_2$-C$_6$)alkenyl(C$_{3-7}$)heterocycle, —(C$_2$-C$_6$)alkynyl(C$_3$-C$_8$)cycloalkyl, —(C$_2$-C$_6$)alkynyl(C$_5$-C$_8$)cycloalkenyl, —(C$_2$-C$_6$)alkynyl(C$_6$)aryl, —(C$_2$-C$_6$)alkynyl(C$_{10}$)aryl, —(C$_2$-C$_6$)alkynyl(C$_{14}$)aryl, or —(C$_2$-C$_6$)alkynyl(C$_3$-C$_7$)heterocycle, which is unsubstituted or substituted with one or more R$^7$ groups.

In another embodiment R$^5$ is —(C$_6$)aryl, optionally substituted with one or more —(C$_2$-C$_6$)alkenyl, —(C$_2$-C$_6$)alkynyl, —(CH$_2$)$_n$(C$_3$-C$_8$)cycloalkyl, —(CH$_2$)$_n$(C$_5$-C$_8$)cycloalkenyl, —(CH$_2$)$_n$(C$_6$)aryl, —(CH$_2$)$_n$SR$^6$, —(CH$_2$)$_n$CH(halo)$_2$, —(CH$_2$)$_n$C(halo)$_3$, -halo or —(CH$_2$)$_n$OR$^6$ groups.

In another embodiment, R$^5$ is phenyl optionally substituted with a —(C$_2$-C$_6$)alkenyl group. In another embodiment, the —(C$_2$-C$_6$)alkenyl group is substituted at the phenyl group's 4-position.

In another embodiment, R$^1$ is methyl and R$^5$ is phenyl optionally substituted with a —(C$_2$-C$_6$)alkenyl group. In another embodiment, $R^1$ is methyl and $R^5$ is phenyl substituted with a —$(C_2-C_6)$alkenyl group at the phenyl group's 4-position.

In another embodiment, $R^1$ is -chloro and $R^5$ is phenyl optionally substituted with a —$(C_2-C_6)$alkenyl group. In another embodiment, $R^1$ is -chloro and $R^5$ is phenyl substituted with a —$(C_2-C_6)$alkenyl group at the phenyl group's 4-position.

In another embodiment, $R^1$ is -bromo and $R^5$ is phenyl optionally substituted with a —$(C_2-C_6)$alkenyl group. In another embodiment, $R^1$ is -bromo and $R^5$ is phenyl substituted with a —$(C_2-C_6)$alkenyl group at the phenyl group's 4-position.

In another embodiment, $R^1$ is -iodo and $R^5$ is phenyl optionally substituted with a —$(C_2-C_6)$alkenyl group. In another embodiment, $R^1$ is -iodo and $R^5$ is phenyl substituted with a —$(C_2-C_6)$alkenyl group at the phenyl group's 4-position.

In another embodiment, $R^1$ is -fluoro and $R^5$ is phenyl optionally substituted with a —$(C_2-C_6)$alkenyl group. In another embodiment, $R^1$ is -fluoro and $R^5$ is phenyl substituted with a —$(C_2-C_6)$alkenyl group at the phenyl group's 4-position.

The present invention also encompasses compounds of Formula (V):

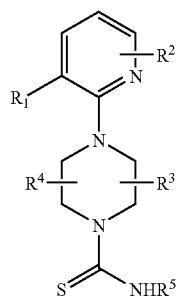

(V)

and pharmaceutically acceptable salts thereof, where $R^1$-$R^5$ are defined above.

In one embodiment, $R_1$ is methyl.
In another embodiment, $R_1$ is halo;
In another embodiment $R^1$ is -chloro.
In another embodiment, $R^1$ is -bromo.
In another embodiment, $R^1$ is -iodo.
In another embodiment, $R^1$ is -fluoro.
In another embodiment, $R^2$ is —$(C_2-C_6)$alkyl, —$(C_2-C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —$NO_2$, —CH=$NR^6$, or —$NR^6OH$.

In another embodiment, $R^2$ is —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6OH$.

In another embodiment, $R^2$ is —H, -halo, —$NO_2$, —CN, or —$NH_2$.
In another embodiment, $R_2$ is —H.
In another embodiment, $R^3$ is —$(C_1-C_6)$alkyl, —$(C_2-C_6)$alkenyl, —$(C_2-C_6)$alkynyl, —$(CH_2)_nOR^6$, which $R^3$ and $R^4$ are each independently unsubstituted or substituted with one or more of —CN, —OH, -halo, —$NO_2$, —CH=$NR^6$, or —$NR^6OH$.

In another embodiment, $R^3$ is —H, -halo, —$NO_2$, —CN, or —$NH_2$.
In another embodiment, $R^3$ is —H.
In another embodiment, $R^3$ is —$CH_3$.

In another embodiment, $R^5$ is —$(C_1-C_6)$alkyl, —$(C_2-C_6)$alkenyl, or —$(C_2-C_6)$alkynyl.

In another embodiment, $R^5$ is —$(C_3-C_8)$cycloalkyl, —$(C_5-C_8)$cycloalkenyl, —$(C_{10})$aryl, —$(C_{14})$aryl, —$(C_3-C_7)$heterocycle, —$(C_1-C_6)$alkyl$(C_6)$aryl, —$(C_1-C_6)$alkyl$(C_{10})$aryl, —$(C_1-C_6)$alkyl$(C_{14})$aryl, —$(C_1-C_6)$alkyl$(C_3-C_7)$heterocycle, —$(C_2-C_6)$alkenyl$(C_6)$aryl, —$(C_2-C_6)$alkenyl$(C_{10})$aryl, —$(C_2-C_6)$alkenyl$(C_{14})$aryl, —$(C_2-C_6)$alkenyl$(C_3-C_7)$heterocycle, —$(C_2-C_6)$alkynyl$(C_3-C_8)$cycloalkyl, —$(C_2-C_6)$alkynyl$(C_5-C_8)$cycloalkenyl, —$(C_2-C_6)$alkynyl$(C_6)$aryl, —$(C_2-C_6)$alkynyl$(C_{10})$aryl, —$(C_2-C_6)$alkynyl$(C_{14})$aryl, or —$(C_2-C_6)$alkynyl$(C_3-C_7)$heterocycle, which is unsubstituted or substituted with one or more $R^7$ groups.

In another embodiment, $R^5$ is —$(C_6)$aryl, optionally substituted with one or more of —$(C_2-C_6)$alkenyl, —$(C_2-C_6)$alkynyl, —$(CH_2)_n(C_3-C_8)$cycloalkyl, —$(CH_2)_n(C_5-C_8)$cycloalkenyl, —$(CH_2)_n(C_6)$aryl, —$(CH_2)_nSR^6$, —$(CH_2)_nCH(halo)_2$, —$(CH_2)_mC(halo)_3$, -halo, —$(CH_2)_nOR^6$.

In another embodiment, $R^5$ is phenyl optionally substituted with a —$(C_2-C_6)$alkenyl group. In another embodiment, the —$(C_2-C_6)$alkenyl group is substituted at the phenyl group's 4-position.

In another embodiment, $R^1$ is methyl and $R^5$ is phenyl optionally substituted with a —$(C_2-C_6)$alkenyl group. In another embodiment, $R^1$ is methyl and $R^5$ is phenyl substituted with a —$(C_2-C_6)$alkenyl group at the phenyl group's 4-position.

In another embodiment, $R^1$ is -chloro and $R^5$ is phenyl optionally substituted with a —$(C_2-C_6)$alkenyl group. In another embodiment, $R^1$ is -chloro and $R^5$ is phenyl substituted with a —$(C_2-C_6)$alkenyl group at the phenyl group's 4-position.

In another embodiment, $R^1$ is -bromo and $R^5$ is phenyl optionally substituted with a —$(C_2-C_6)$alkenyl group. In another embodiment, $R^1$ is -bromo and $R^5$ is phenyl substituted with a —$(C_2-C_6)$alkenyl group at the phenyl group's 4-position.

In another embodiment, $R^1$ is -iodo and $R^5$ is phenyl optionally substituted with a —$(C_2-C_6)$alkenyl group. In another embodiment, $R^1$ is -iodo and $R^5$ is phenyl substituted with a —$(C_2-C_6)$alkenyl group at the phenyl group's 4-position.

In another embodiment, $R^1$ is -fluoro and $R^5$ is phenyl optionally substituted with a —$(C_2-C_6)$alkenyl group. In another embodiment, $R^1$ is -fluoro and $R^5$ is phenyl substituted with a —$(C_2-C_6)$alkenyl group at the phenyl group's 4-position.

The present invention also encompasses compounds of Formula (VI):

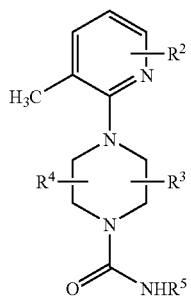

(VI)

and pharmaceutically acceptable salts thereof, where $R^1$-$R^5$ are defined above.

In one embodiment, $R^2$ is —$(C_2-C_6)$alkyl, —$(C_2-C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —NO$_2$, —CH=NR$^6$, or —NR$^6$OH.

In another embodiment, R$^2$ is —CH$_3$, —CH$_2$F, or —CHF$_2$, which is unsubstituted or substituted with one or more of —CN, —OH, —Cl, —Br, —I, —NO$_2$, —CH=NR$^6$, or —NR$^6$OH.

In another embodiment, R$^2$ is —H, -halo, —NO$_2$, —CN, or —NH$_2$.

In another embodiment, R$_2$ is —H.

In another embodiment, R$^3$ is —(C$_1$-C$_6$)alkyl, —(C$_2$-C$_6$)alkenyl, —(C$_2$-C$_6$)alkynyl, —(CH$_2$)$_n$OR$^6$, which R$^3$ and R$^4$ are each independently unsubstituted or substituted with one or more of —CN, —OH, -halo, —NO$_2$, —CH=NR$^6$, or —NR$^6$OH.

In another embodiment, R$^3$ is —H, -halo, —NO$_2$, —CN, or —NH$_2$.

In another embodiment, R$^3$ is —H.

In another embodiment, R$^3$ is —CH$_3$.

In another embodiment, R$^5$ is —(C$_1$-C$_6$)alkyl, —(C$_2$-C$_6$)alkenyl, or —(C$_2$-C$_6$)alkynyl.

In another embodiment, R$^5$ is —(C$_3$-C$_8$)cycloalkyl, —(C$_5$-C$_8$)cycloalkenyl, —(C$_6$)aryl, —(C$_{10}$)aryl, —(C$_3$-C$_7$)heterocycle, —(C$_1$-C$_6$)alkyl(C$_6$)aryl, —(C$_1$-C$_6$)alkyl(C$_{10}$)aryl, —(C$_1$-C$_6$)alkyl(C$_{14}$)aryl, —(C$_1$-C$_6$)alkyl(C$_3$-C$_7$)heterocycle, —(C$_2$-C$_6$)alkenyl(C$_6$)aryl, —(C$_2$-C$_6$)alkenyl(C$_{10}$)aryl, —(C$_2$-C$_6$)alkenyl(C$_{14}$)aryl, —(C$_2$-C$_6$)alkenyl(C$_3$-C$_7$)heterocycle, —(C$_2$-C$_6$)alkynyl(C$_3$-C$_8$)cycloalkyl, —(C$_2$-C$_6$)alkynyl(C$_5$-C$_8$)cycloalkenyl, —(C$_2$-C$_6$)alkynyl(C$_6$)aryl, —(C$_2$-C$_6$)alkynyl(C$_{10}$)aryl, —(C$_2$-C$_6$)alkynyl(C$_{14}$)aryl, or —(C$_2$-C$_6$)alkynyl(C$_3$-C$_7$)heterocycle, which is unsubstituted or substituted with one or more R$^7$ groups.

In another embodiment, R$^5$ is —(C$_6$)aryl, optionally substituted with one or more (C$_2$-C$_6$)alkenyl, —(C$_2$-C$_6$)alkynyl, —(CH$_2$)$_n$(C$_3$-C$_8$)cycloalkyl, —(CH$_2$)$_n$(C$_5$-C$_8$)cycloalkenyl, —(CH$_2$)$_n$(C$_6$)aryl, —(CH$_2$)$_n$SR$^6$, —(CH$_2$)$_n$CH(halo)$_2$, —(CH$_2$)$_n$C(halo)$_3$, -halo or —(CH$_2$)$_n$OR$^6$ groups.

In another embodiment, R$^5$ is phenyl optionally substituted with a —(C$_2$-C$_6$)alkenyl group. In another embodiment, the —(C$_2$-C$_6$)alkenyl group is substituted at the phenyl group's 4-position.

In another embodiment, R$^5$ is phenyl optionally substituted with a —(C$_1$-C$_6$) alkyl group. In another embodiment, the —(C$_1$-C$_6$) alkyl group is substituted at the phenyl group's 4-position. In another embodiment, the —(C$_1$-C$_6$) alkyl group is a t-butyl group.

The present invention also encompasses compounds of Formula (VII):

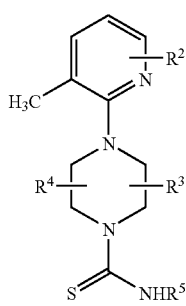

(VII)

The present invention also encompasses compounds of Formula (VIII):

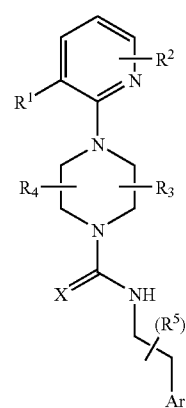

(VIII)

and pharmaceutically acceptable salts thereof, where R$^1$-R$^5$ are defined above.

In one embodiment, R$^2$ is —(C$_2$-C$_6$)alkyl, —(C$_2$-C$_3$)alkenyl, —(CH$_2$)$_n$C(O)R$^6$, —(CH$_2$)$_n$OR$^6$, —(CH$_2$)$_n$SR$^6$, which is unsubstituted or substituted with one or more of —CN, —OH, -halo, —NO$_2$, —CH=NR$^6$, or —NR$^6$OH.

and pharmaceutically acceptable salts thereof, where R$^1$-R$^5$, Ar, X and p are defined above for formula (VIII).

In one embodiment, X is O.

In another embodiment, X is S.

In another embodiment, R$^1$ is methyl.

In another embodiment, R$^1$ is halo.

In another embodiment R$^1$ is -chloro.

In another embodiment, R$^1$ is -bromo.

In another embodiment, R$^1$ is -iodo.

In another embodiment, R$^1$ is -fluoro.

In another embodiment, X is O and R$^1$ is methyl.

In another embodiment, X is O and $R^1$ is halo.
In another embodiment X is O and $R^1$ is -chloro.
In another embodiment, X is O and $R^1$ is -bromo.
In another embodiment, X is O and $R^1$ is -iodo.
In another embodiment, X is O and $R^1$ is -fluoro.
In another embodiment, X is S and $R^1$ is methyl.
In another embodiment, X is S and $R^1$ is halo.
In another embodiment X is S and $R^1$ is -chloro.
In another embodiment, X is S and $R^1$ is -bromo.
In another embodiment, X is S and $R^1$ is -iodo.
In another embodiment, X is S and $R^1$ is -fluoro.
In another embodiment, $R^2$ is —$(C_2-C_6)$alkyl, —$(C_2-C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —$NO_2$, —CH=$NR^6$, or —$NR^6$OH.
In another embodiment, $R^2$ is —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6$OH.
In another embodiment, $R^2$ is —H, -halo, —$NO_2$, —CN, or —$NH_2$.
In another embodiment, $R_2$ is —H.
In another embodiment, $R^3$ is —$(C_1-C_6)$alkyl, —$(C_2-C_6)$alkenyl, —$(C_2-C_6)$alkynyl, —$(CH_2)_nOR^6$, which is unsubstituted or substituted with one or more of —CN, —OH, -halo, —$NO_2$, —CH=$NR^6$, or —$NR^6$OH.
In another embodiment, $R^3$ is —H, -halo, —$NO_2$, —CN, or —$NH_2$.
In another embodiment, $R^3$ is —H.
In another embodiment, $R^3$ is —$CH_3$.
In another embodiment, Ar is —$(C_6)$aryl, which is unsubstituted or substituted with one or more $R^1$ groups.
In another embodiment, Ar is —$(C_{10})$aryl, which is unsubstituted or substituted with one or more $R^7$ groups.
In another embodiment, Ar is —$(C_{14})$aryl, which is unsubstituted or substituted with one or more $R^7$ groups.
In another embodiment, Ar is —$(C_3-C_8)$cycloalkyl, which is unsubstituted or substituted with one or more $R^7$ groups.
In another embodiment, Ar is —$(C_5-C_8)$cycloalkenyl, which is unsubstituted or substituted with one or more $R^7$ groups.
In another embodiment, $R^1$ is methyl and Ar is phenyl, optionally substituted with a —$(C_1-C_6)$ alkyl group. In another embodiment, the —$(C_1-C_6)$ alkyl group is a t-butyl group.
In another embodiment, $R^1$ is methyl and Ar is phenyl, substituted in the 4-position with a —$(C_1-C_6)$ alkyl group. In another embodiment, the —$(C_1-C_6)$ alkyl group is a t-butyl group.
In another embodiment, $R^1$ is -halo and Ar is phenyl, optionally substituted with a —$(C_1-C_6)$ alkyl group. In another embodiment, the —$(C_1-C_6)$ alkyl group is a t-butyl group.
In another embodiment, $R^1$ is -halo and Ar is phenyl, substituted in the 4-position with a —$(C_1-C_6)$ alkyl group. In another embodiment, the —$(C_1-C_6)$ alkyl group is a t-butyl group.
In another embodiment, $R^1$ is -chloro and Ar is phenyl, optionally substituted with a —$(C_1-C_6)$ alkyl group. In another embodiment, the —$(C_1-C_6)$ alkyl group is a t-butyl group.
In another embodiment, $R^1$ is -chloro and Ar is phenyl, substituted in the 4-position with a —$(C_1-C_6)$ alkyl group. In another embodiment, the —$(C_1-C_6)$ alkyl group is a t-butyl group.
In another embodiment, $R^1$ is -bromo and Ar is phenyl, optionally substituted with a —$(C_1-C_6)$ alkyl group. In another embodiment, the —$(C_1-C_6)$ alkyl group is a t-butyl group.
In another embodiment, $R^1$ is -bromo and Ar is phenyl, substituted in the 4-position with a —$(C_1-C_6)$ alkyl group. In another embodiment, the —$(C_1-C_6)$ alkyl group is a t-butyl group.
In another embodiment, $R^1$ is -iodo and Ar is phenyl, optionally substituted with a —$(C_1-C_6)$ alkyl group. In another embodiment, the —$(C_1-C_6)$ alkyl group is a t-butyl group.
In another embodiment, $R^1$ is -iodo and Ar is phenyl, substituted in the 4-position with a —$(C_1-C_6)$ alkyl group. In another embodiment, the —$(C_1-C_6)$ alkyl group is a t-butyl group.
In another embodiment, $R^1$ is -fluoro and Ar is phenyl, optionally substituted with a —$(C_1-C_6)$ alkyl group. In another embodiment, the —$(C_1-C_6)$ alkyl group is a t-butyl group.
In another embodiment, $R^1$ is -fluoro and Ar is phenyl, substituted in the 4-position with a —$(C_1-C_6)$ alkyl group. In another embodiment, the —$(C_1-C_6)$ alkyl group is a t-butyl group.
In another embodiment, p is 0.
In another embodiment, p is 1.
In another embodiment, p is 2.
In another embodiment, p is 1 and $R^5$ is —$CH_3$.
In another embodiment, p is 2 and each $R^5$ is —$CH_3$.
The present invention also encompasses compounds of Formula (IX):

(IX)

or a pharmaceutically acceptable salt thereof, where $R^1$-$R^5$, Ar, X and p are defined above for formula (IX).
In one embodiment, X is O.
In another embodiment, X is S.
In another embodiment, $R^1$ is methyl.
In another embodiment, $R^1$ is halo.
In another embodiment $R^1$ is -chloro.
In another embodiment, $R^1$ is -bromo.
In another embodiment, $R^1$ is -iodo.
In another embodiment, $R^1$ is -fluoro.
In another embodiment, X is O and $R^1$ is methyl.
In another embodiment, X is O and $R^1$ is halo.
In another embodiment X is O and $R^1$ is -chloro.
In another embodiment, X is O and $R^1$ is -bromo.
In another embodiment, X is O and $R^1$ is -iodo.
In another embodiment, X is O and $R^1$ is -fluoro.
In another embodiment, X is S and $R^1$ is methyl.

In another embodiment, X is S and $R^1$ is halo.
In another embodiment X is S and $R^1$ is -chloro.
In another embodiment, X is S and $R^1$ is -bromo.
In another embodiment, X is S and $R^1$ is -iodo.
In another embodiment, X is S and $R^1$ is -fluoro.

In another embodiment, $R^2$ is —$(C_2$-$C_6)$alkyl, —$(C_2$-$C_3)$alkenyl, —$(CH_2)_nC(O)R^6$, —$(CH_2)_nOR^6$, —$(CH_2)_nSR^6$, which is unsubstituted or substituted with one or more of —CN, —OH, -halo, —$NO_2$, —CH=$NR^6$, or —$NR^6$OH.

In another embodiment, $R^2$ is —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6$OH.

In another embodiment, $R^2$ is —H, -halo, —$NO_2$, —CN, or —$NH_2$.

In another embodiment, $R_2$ is —H.

In another embodiment, $R^3$ is —$(C_1$-$C_6)$alkyl, —$(C_2$-$C_6)$alkenyl, —$(C_2$-$C_6)$alkynyl, —$(CH_2)_nOR^6$, which is unsubstituted or substituted with one or more of —CN, —OH, -halo, —$NO_2$, —CH=$NR^6$, or —$NR^6$OH.

In another embodiment, $R^3$ is —H, -halo, —$NO_2$, —CN, or —$NH_2$.

In another embodiment, $R^3$ is —H.
In another embodiment, $R^3$ is —$CH_3$.

In another embodiment, Ar is —$(C_6)$aryl, which is unsubstituted or substituted with one or more $R^7$ groups.

In another embodiment, Ar is —$(C_{10})$aryl, which is unsubstituted or substituted with one or more $R^7$ groups.

In another embodiment, Ar is —$(C_{14})$aryl, which is unsubstituted or substituted with one or more $R^7$ groups.

In another embodiment, Ar is —$(C_3$-$C_8)$cycloalkyl, which is unsubstituted or substituted with one or more $R^1$ groups.

In another embodiment, Ar is —$(C_5$-$C_8)$cycloalkenyl, which is unsubstituted or substituted with one or more $R^7$ groups.

In another embodiment, $R^1$ is methyl and Ar is phenyl, optionally substituted with a —$(C_1$-$C_6)$ alkyl group. In another embodiment, the —$(C_1$-$C_6)$ alkyl group is a t-butyl group.

In another embodiment, $R^1$ is methyl and Ar is phenyl, substituted in the 4-position with a —$(C_1$-$C_6)$ alkyl group. In another embodiment, the —$(C_1$-$C_6)$ alkyl group is a t-butyl group.

In another embodiment, $R^1$ is -halo and Ar is phenyl, optionally substituted with a —$(C_1$-$C_6)$ alkyl group. In another embodiment, the —$(C_1$-$C_6)$ alkyl group is a t-butyl group.

In another embodiment, $R^1$ is -halo and Ar is phenyl, substituted in the 4-position with a —$(C_1$-$C_6)$ alkyl group. In another embodiment, the —$(C_1$-$C_6)$ alkyl group is a t-butyl group.

In another embodiment, $R^1$ is -chloro and Ar is phenyl, optionally substituted with a —$(C_1$-$C_6)$ alkyl group. In another embodiment, the —$(C_1$-$C_6)$ alkyl group is a t-butyl group.

In another embodiment, $R^1$ is -chloro and Ar is phenyl, substituted in the 4-position with a —$(C_1$-$C_6)$ alkyl group. In another embodiment, the —$(C_1$-$C_6)$ alkyl group is a t-butyl group.

In another embodiment, $R^1$ is -bromo and Ar is phenyl, optionally substituted with a —$(C_1$-$C_6)$ alkyl group. In another embodiment, the —$(C_1$-$C_6)$ alkyl group is a t-butyl group.

In another embodiment, $R^1$ is -bromo and Ar is phenyl, substituted in the 4-position with a —$(C_1$-$C_6)$ alkyl group. In another embodiment, the —$(C_1$-$C_6)$ alkyl group is a t-butyl group.

In another embodiment, $R^1$ is -iodo and Ar is phenyl, optionally substituted with a —$(C_1$-$C_6)$ alkyl group. In another embodiment, the —$(C_1$-$C_6)$ alkyl group is a t-butyl group.

In another embodiment, $R^1$ is -iodo and Ar is phenyl, substituted in the 4-position with a —$(C_1$-$C_6)$ alkyl group. In another embodiment, the —$(C_1$-$C_6)$ alkyl group is a t-butyl group.

In another embodiment, $R^1$ is -fluoro and Ar is phenyl, optionally substituted with a —$(C_1$-$C_6)$ alkyl group. In another embodiment, the —$(C_1$-$C_6)$ alkyl group is a t-butyl group.

In another embodiment, $R^1$ is -fluoro and Ar is phenyl, substituted in the 4-position with a —$(C_1$-$C_6)$ alkyl group. In another embodiment, the —$(C_1$-$C_6)$ alkyl group is a t-butyl group.

In another embodiment, p is 0.
In another embodiment, p is 1.
In another embodiment, p is 2
In another embodiment, p is 1 and $R^5$ is —$CH_3$.
In another embodiment, p is 2 and each $R^5$ is —$CH_3$.

Illustrative Piperazine Compounds, obtainable by the methods declared herein, are:

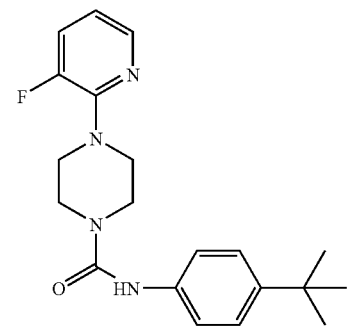

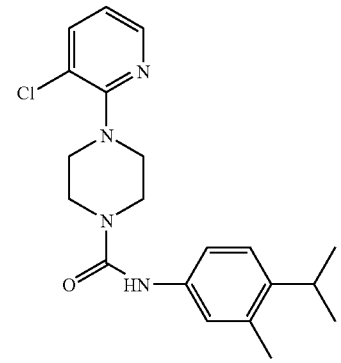

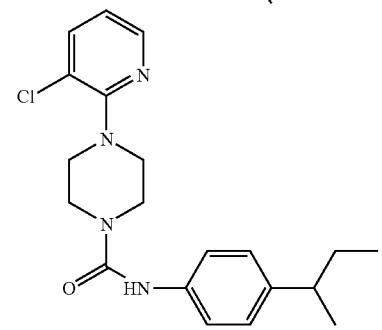

-continued
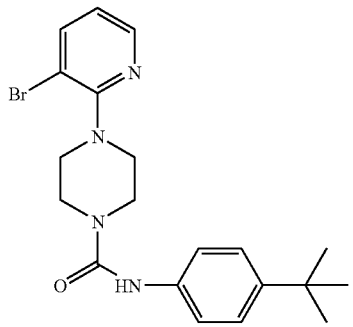
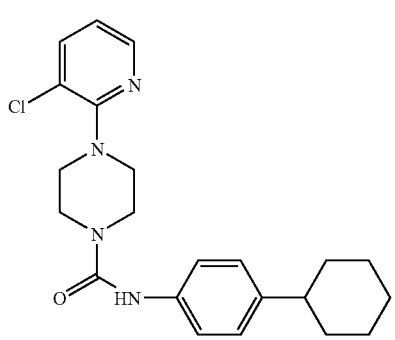
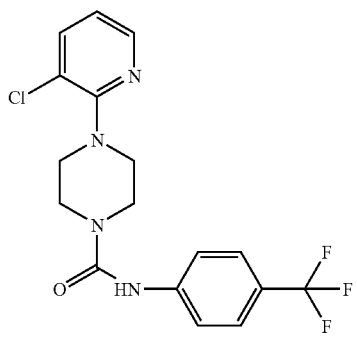
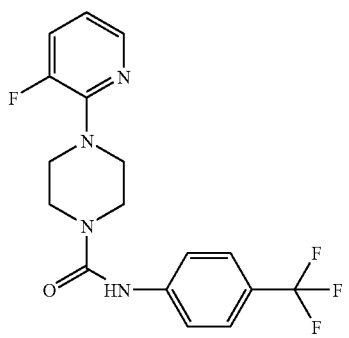
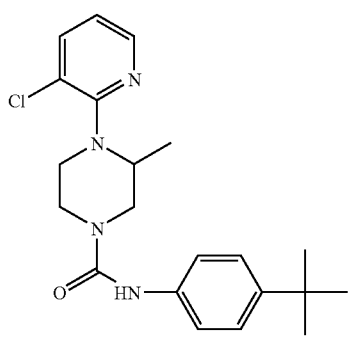
-continued
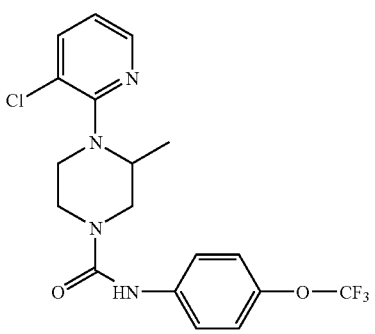
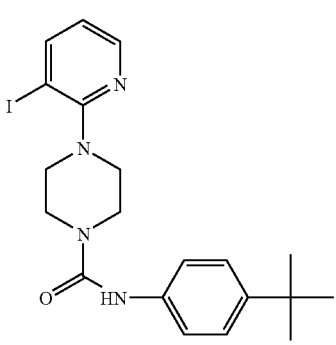
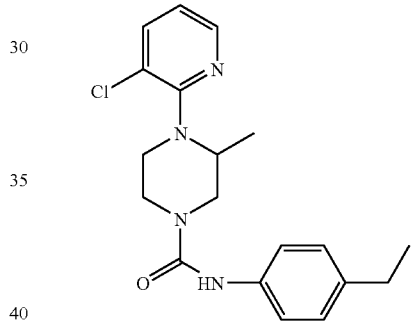
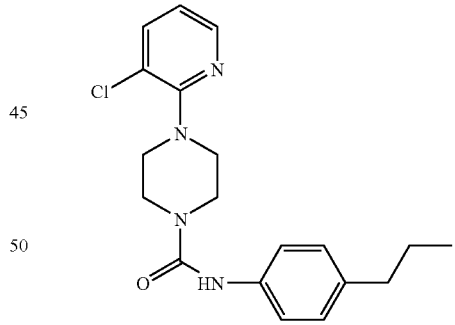
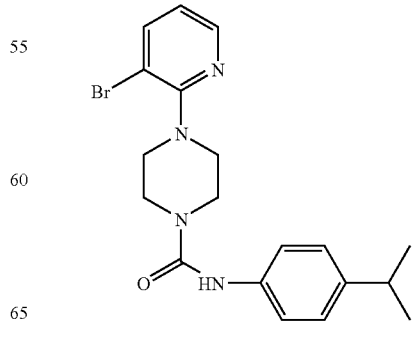

-continued
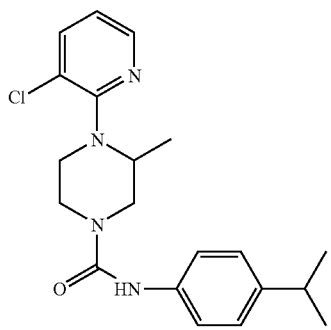
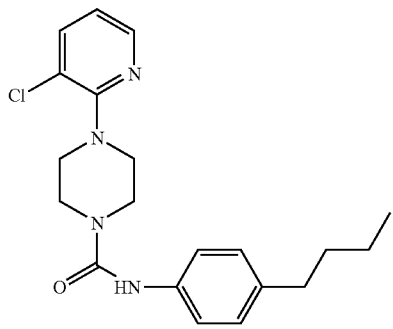
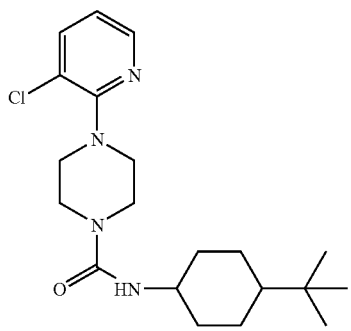
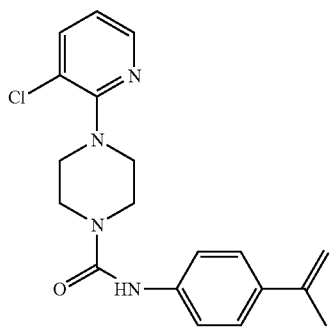
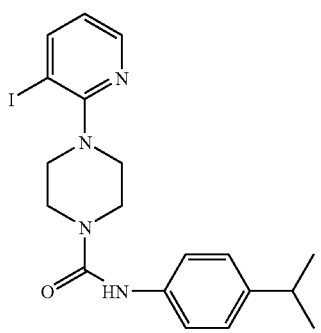
-continued
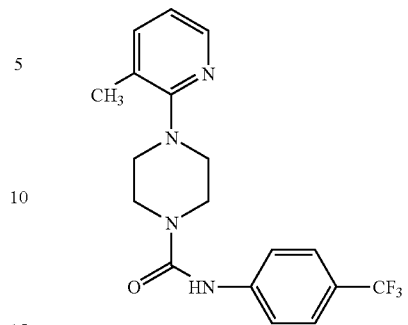
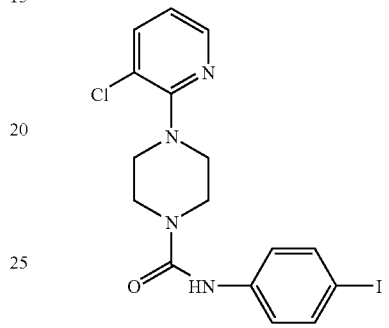
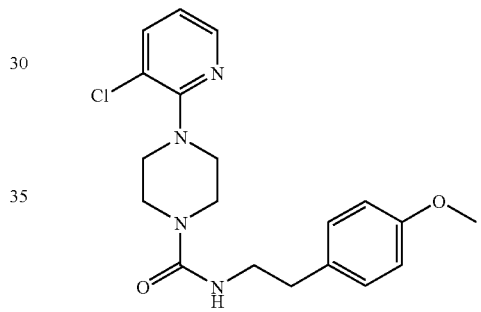
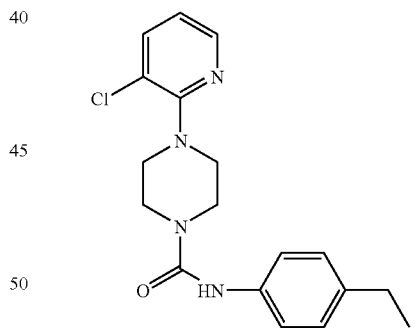
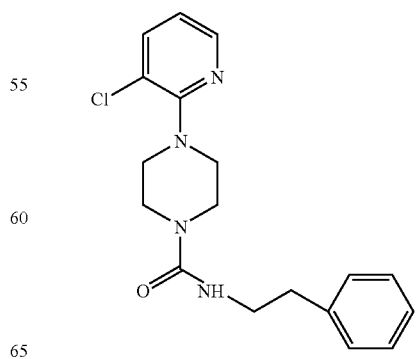

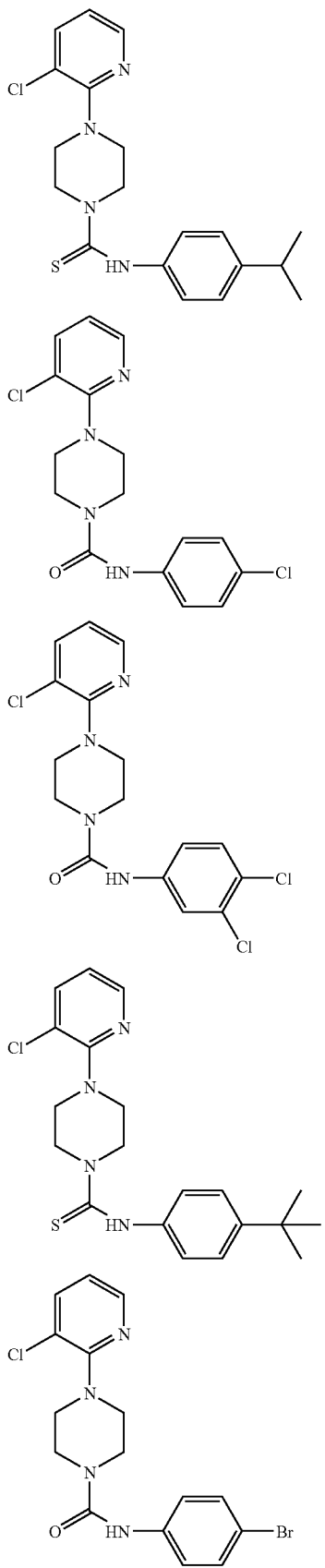
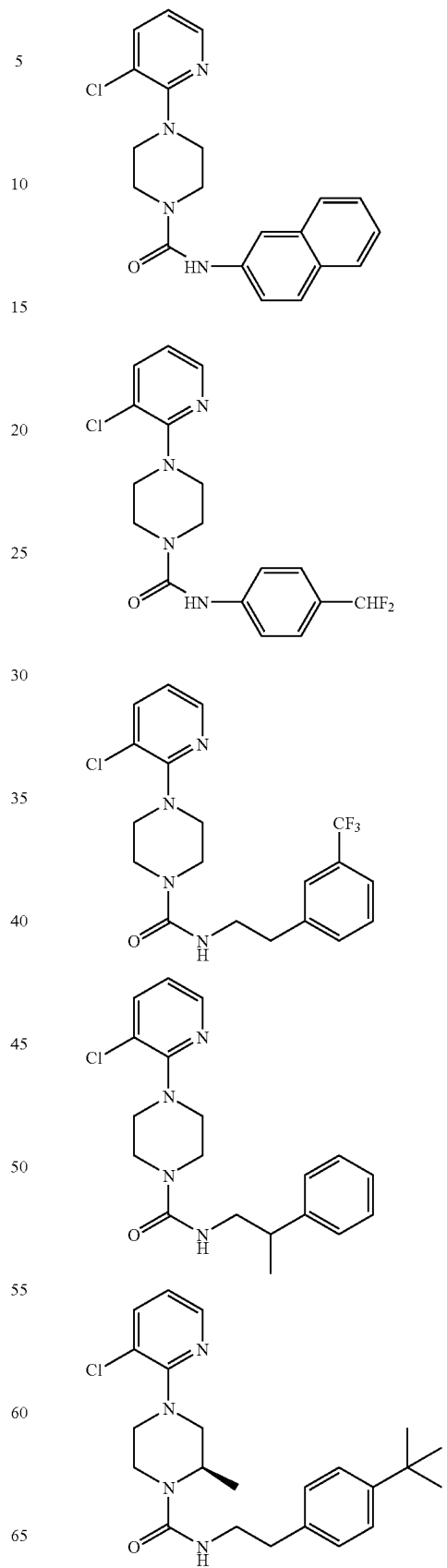

-continued
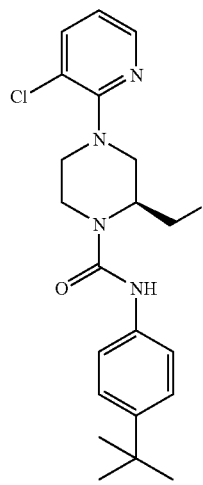
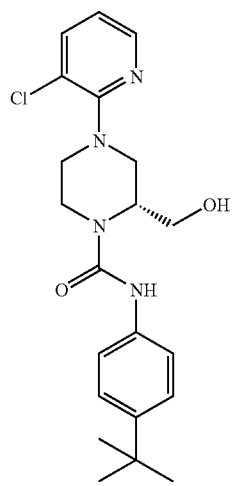
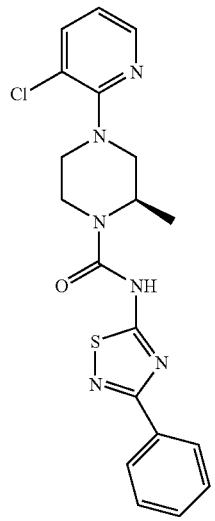
-continued
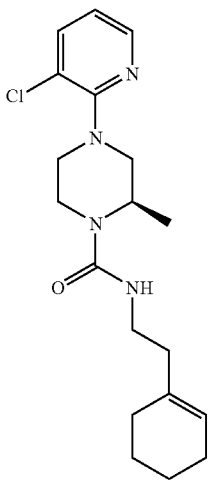
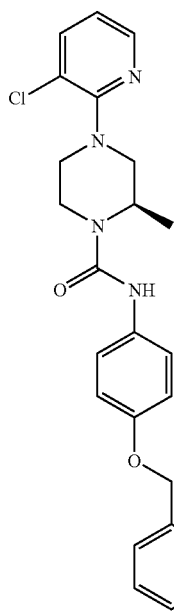
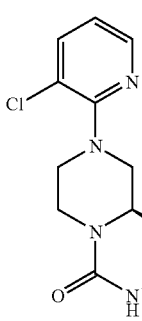
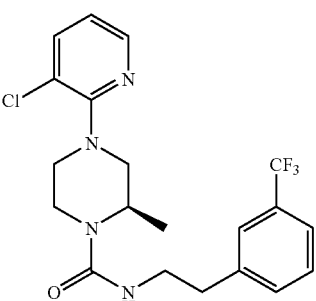
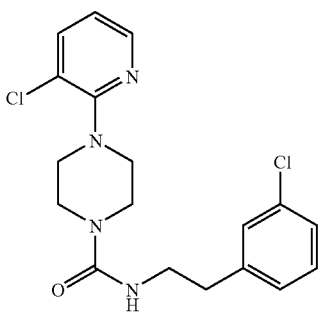

-continued
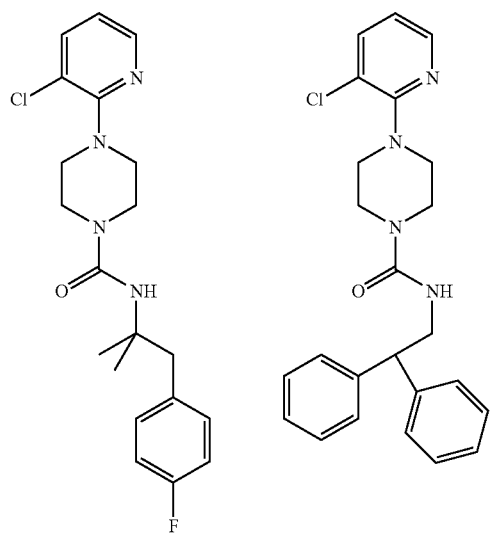
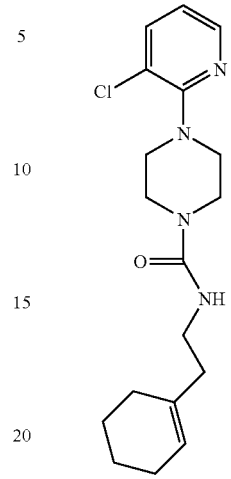
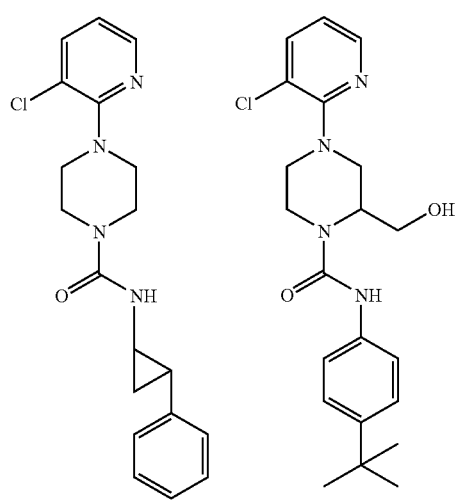
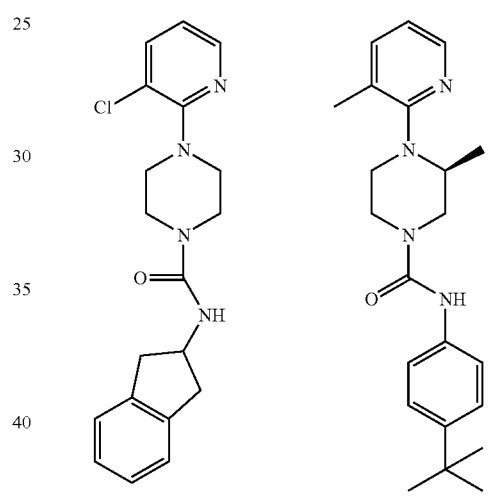
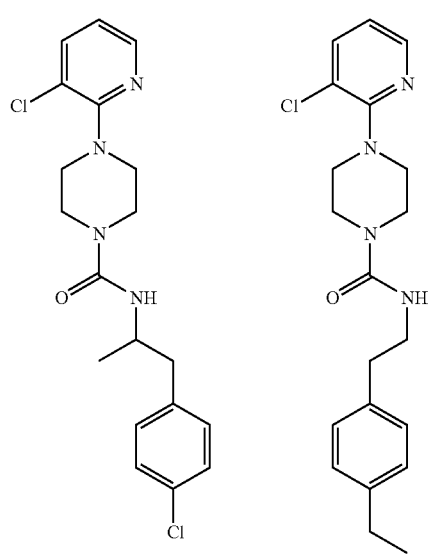
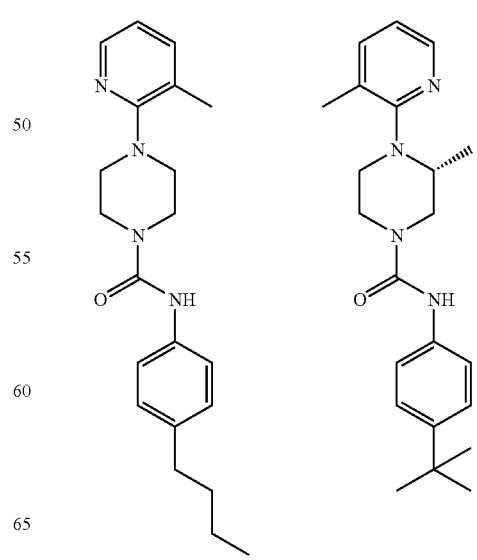

-continued
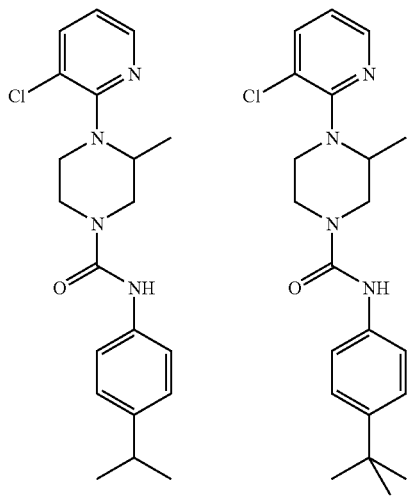
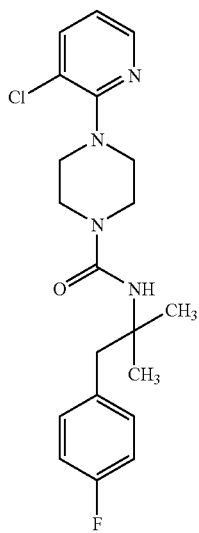
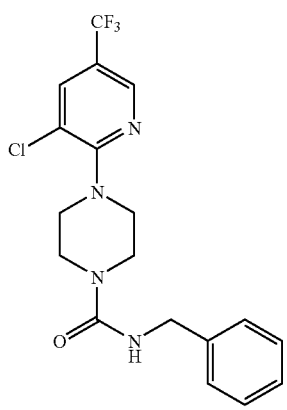
-continued
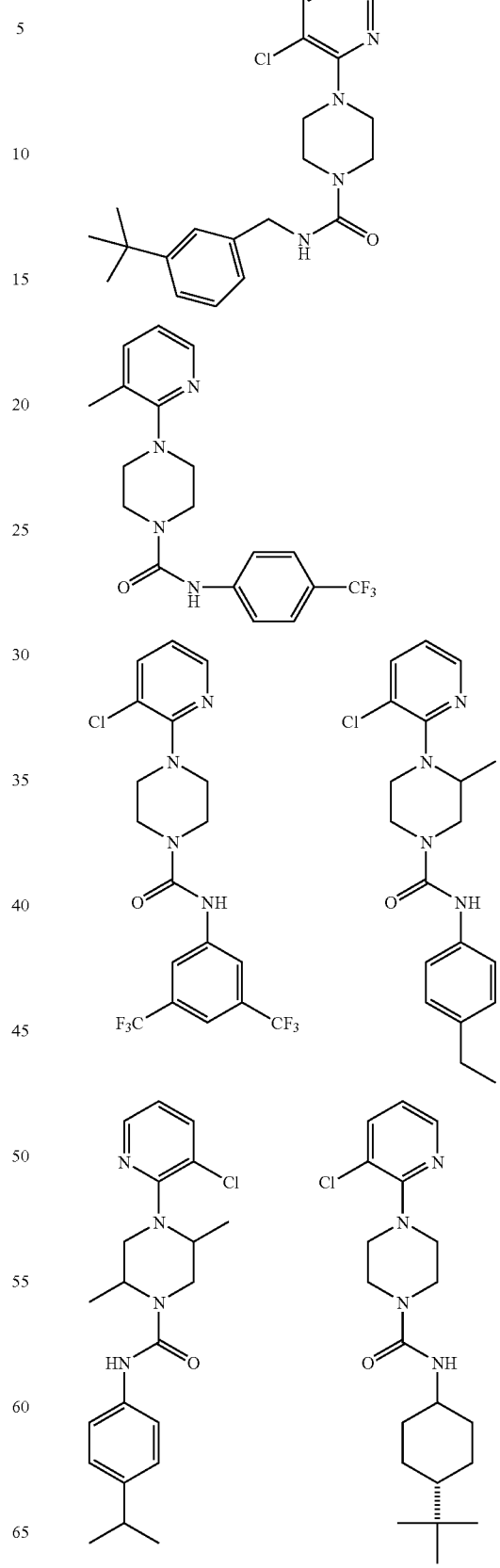

-continued
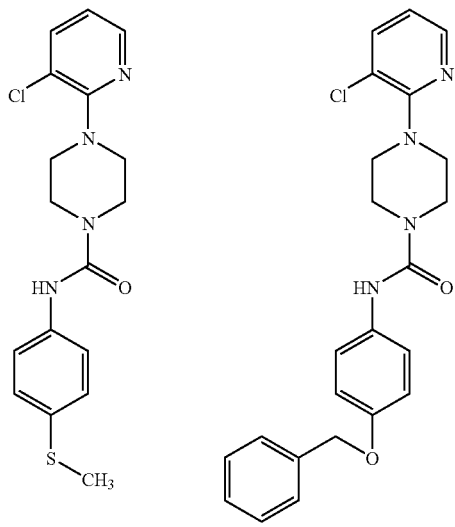 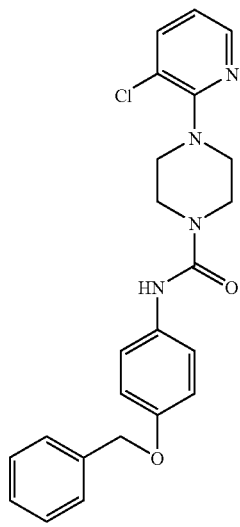 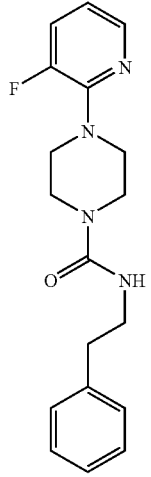 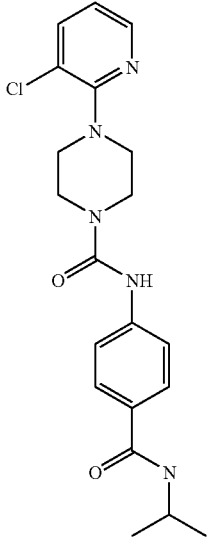
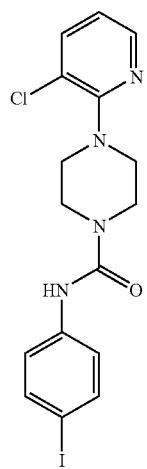 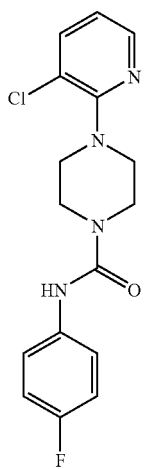 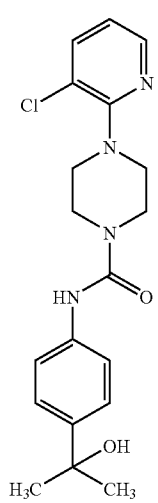 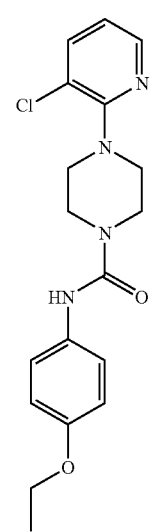
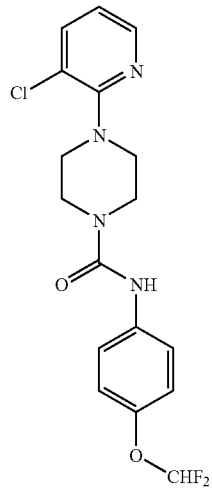 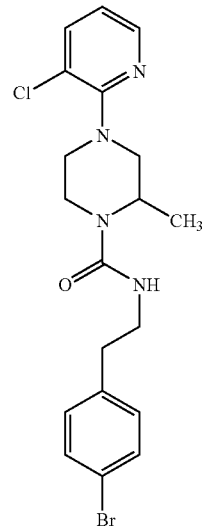 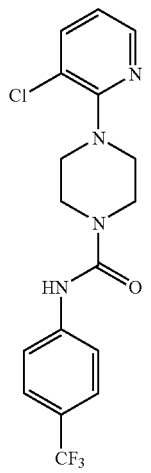 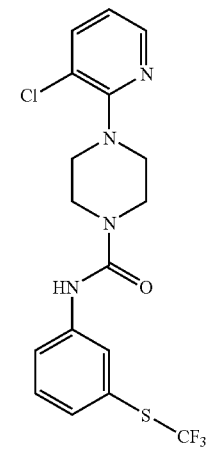

-continued
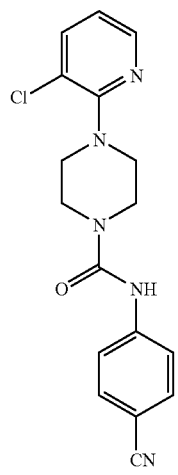 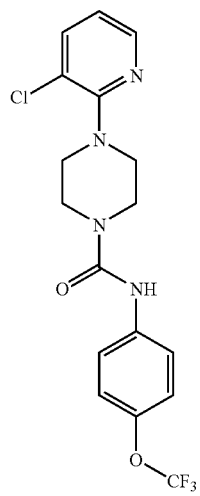 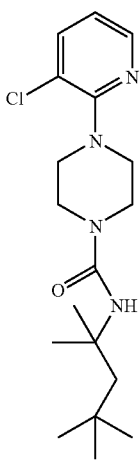 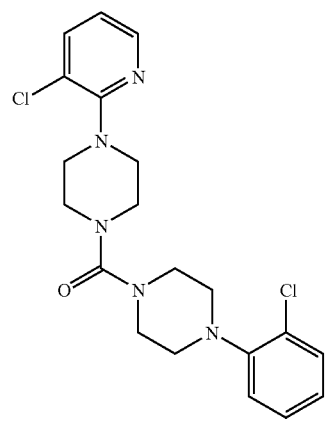
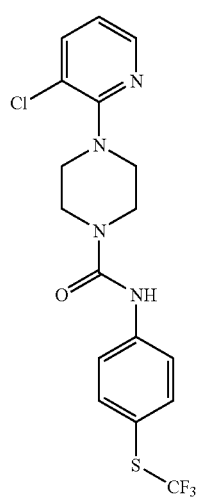 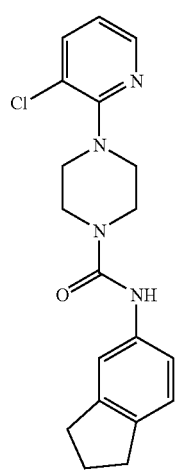 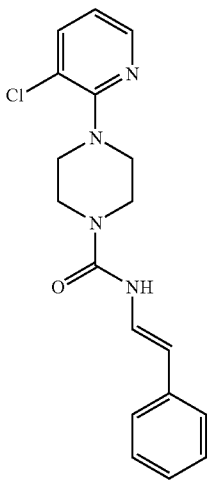 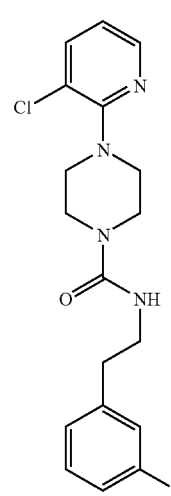
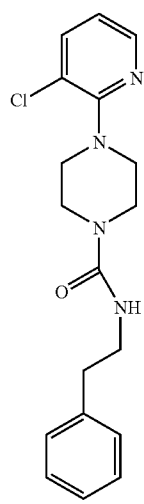 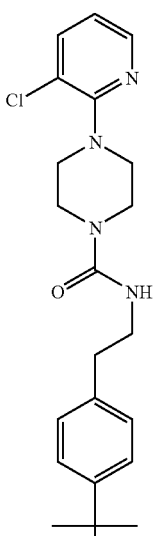 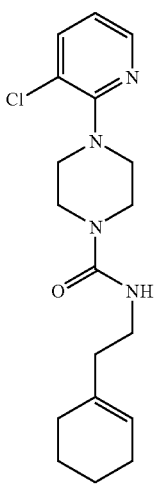 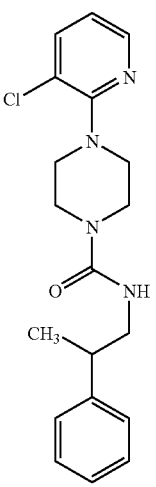

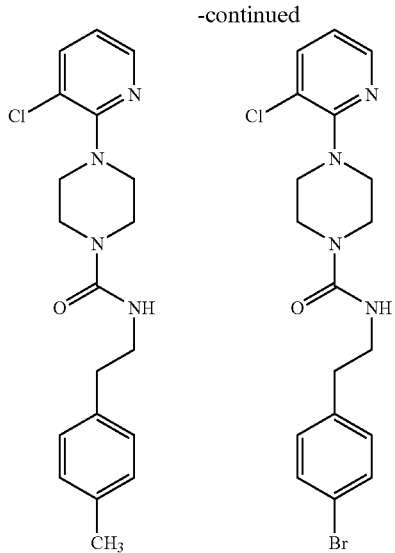

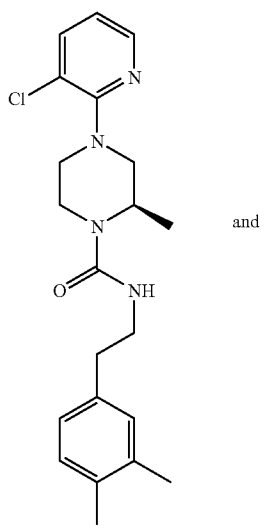

and

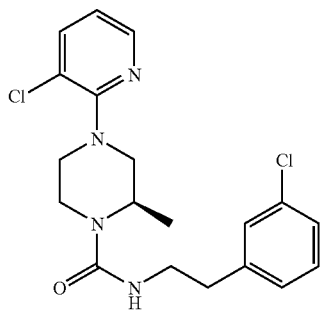

and pharmaceutically acceptable salts thereof.

In one embodiment the invention relates to methods for inhibiting mGluR1 function in a cell comprising contacting a cell capable of expressing mGluR1 with an effective amount of a compound of formula (I)-(IX), defined above, or a pharmaceutically acceptable salt thereof.

In one embodiment the invention relates to methods for inhibiting mGluR5 function in a cell comprising contacting a cell capable of expressing mGluR5 with an effective amount of a compound of formula (I)-(IX), defined above, or a pharmaceutically acceptable salt thereof.

In another embodiment the invention relates to methods for treating or preventing pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal, comprising administering to an animal in need thereof an effective amount of a compound or pharmaceutically acceptable salt of a compound of formula (I)-(IX).

In another embodiment the invention relates to methods for treating or preventing an addictive disorder, Parkinson's disease, parkinsonism, anxiety, epilepsy, stroke, a seizure, psychosis, a cognitive disorder, a memory deficit, restricted brain function, Huntington's chorea, ALS, dementia, retinopathy, a muscle spasm, a migraine, vomiting, dyskinesia, or depression in an animal, comprising administering to an animal in need thereof an effective amount of a compound or pharmaceutically acceptable salt of a compound of formula (I)-(IX).

In another embodiment the invention relates to methods for treating or preventing pain, an addictive disorder, Parkinson's disease, parkinsonism, anxiety, a pruritic condition, or psychosis in an animal, comprising administering to an animal in need thereof an effective amount of a compound or pharmaceutically acceptable salt of a compound of formula (I)-(IX).

In another embodiment the invention relates to methods for treating or preventing an addictive disorder, Parkinson's disease, parkinsonism, anxiety, or psychosis in an animal, comprising administering to an animal in need thereof an effective amount of a compound or pharmaceutically acceptable salt of a compound of formula (I)-(IX).

Illustrative examples of compounds of formula (I) or (II) useful in the above methods are:

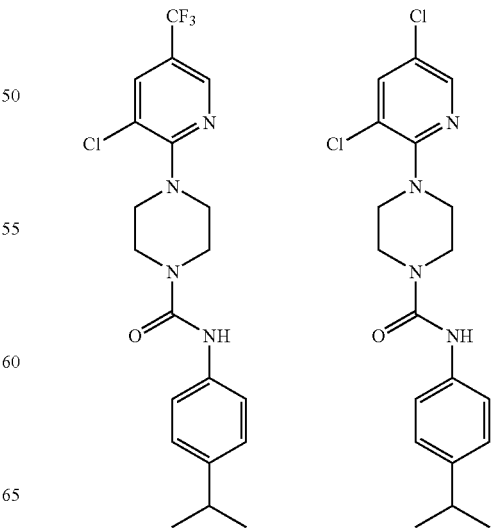

-continued
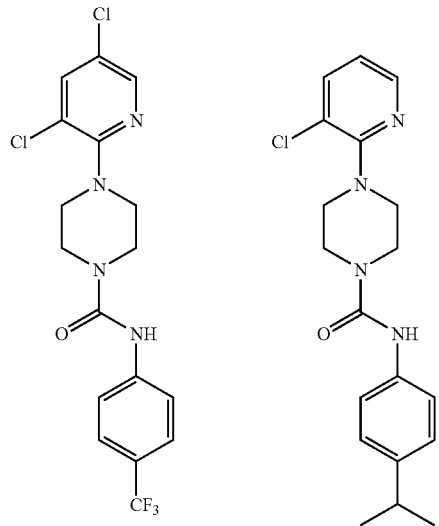
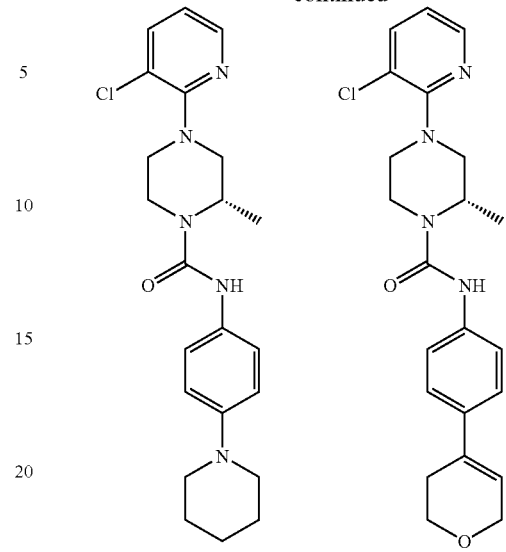
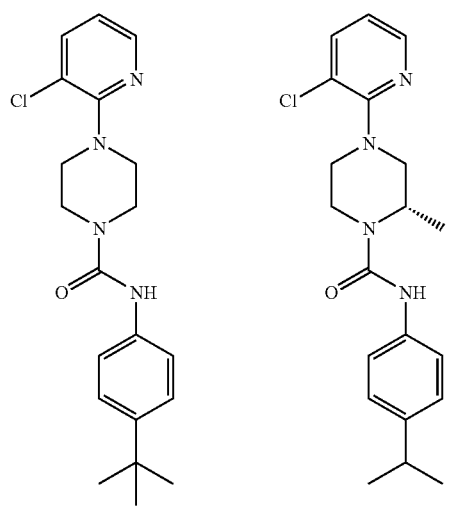
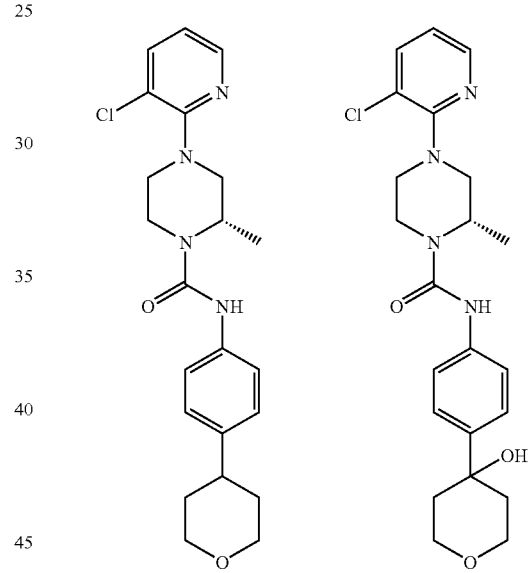
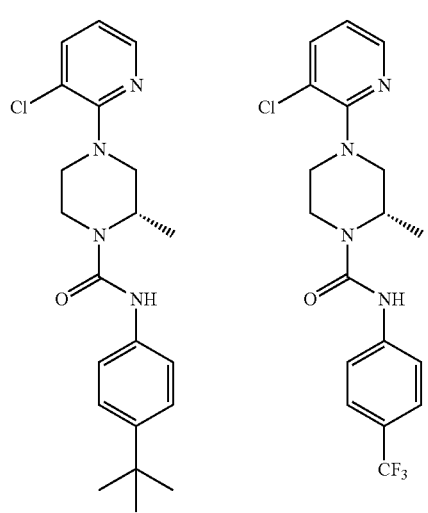
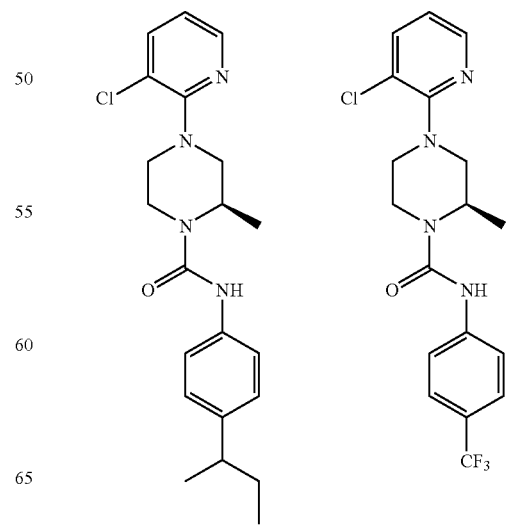

-continued
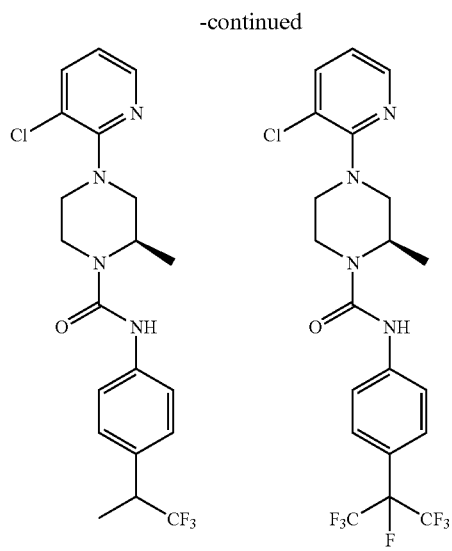
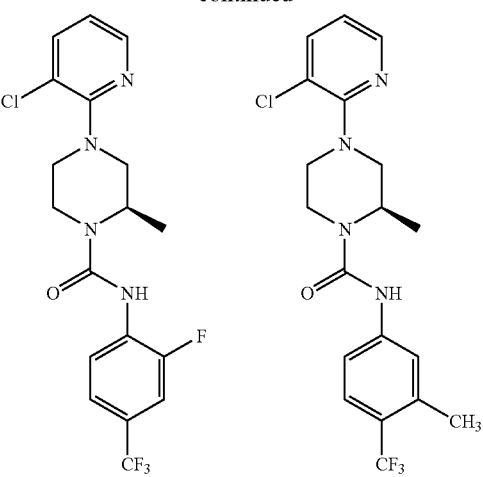
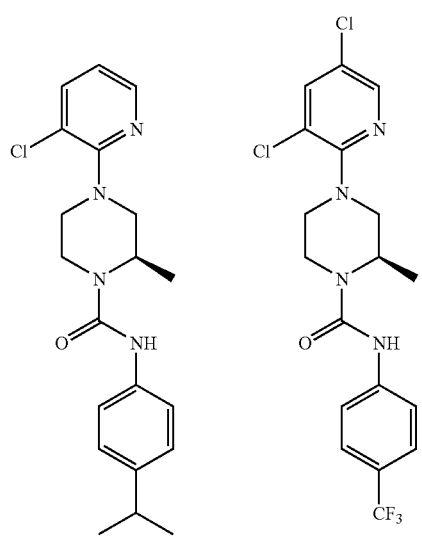
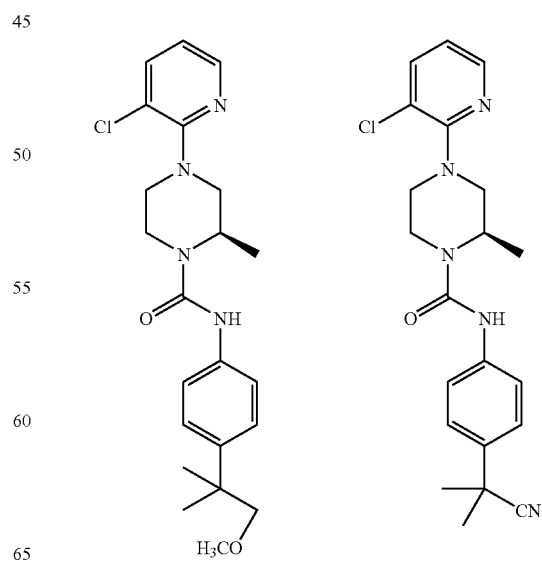

-continued
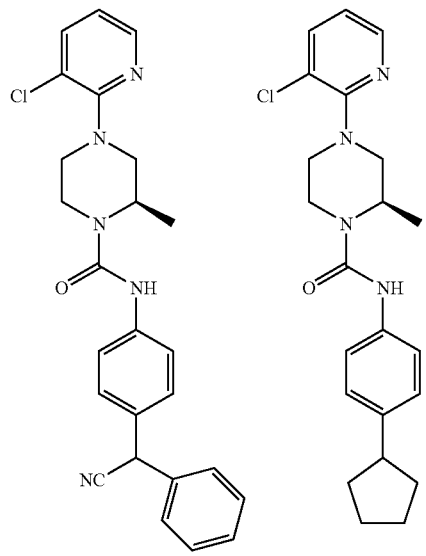
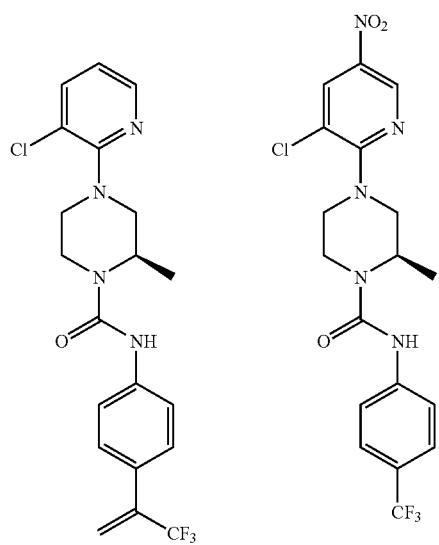
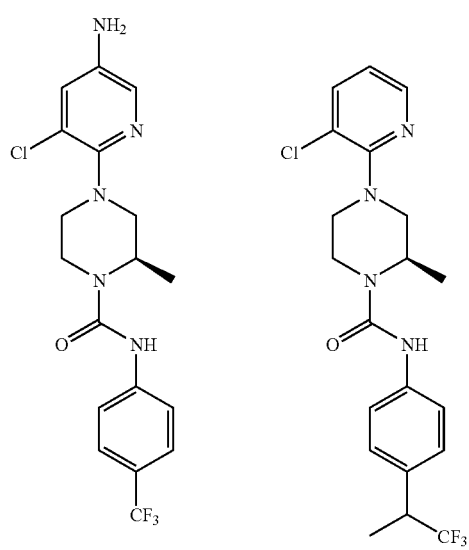
-continued
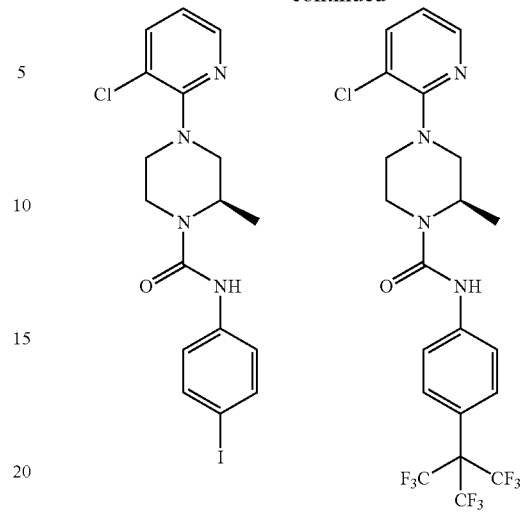
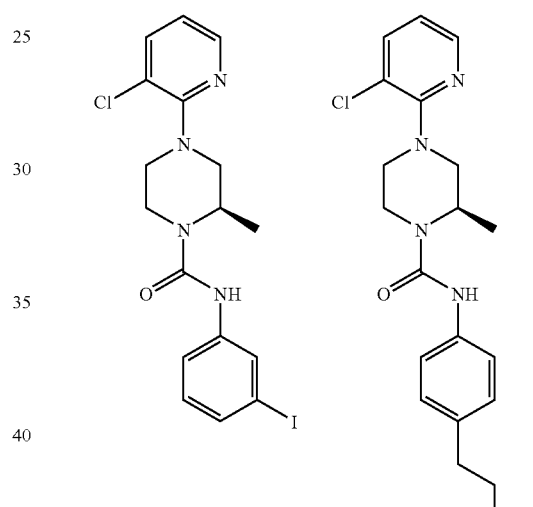
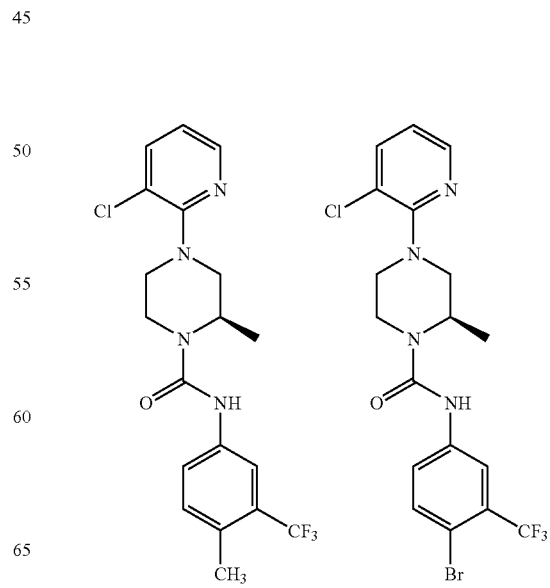

-continued
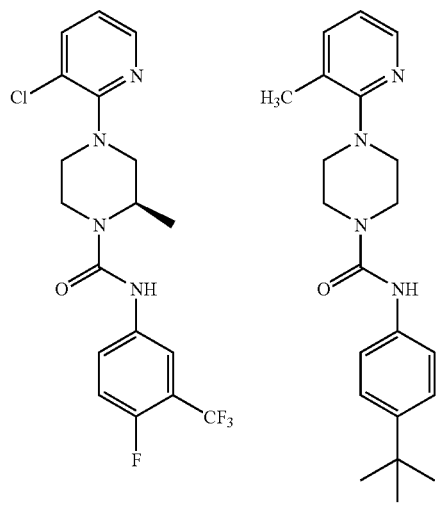
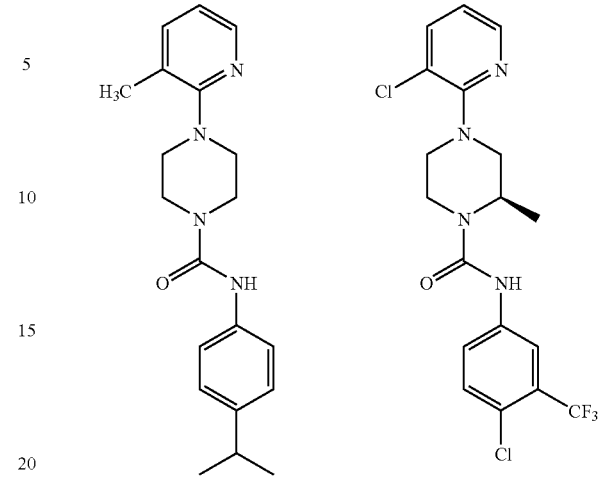
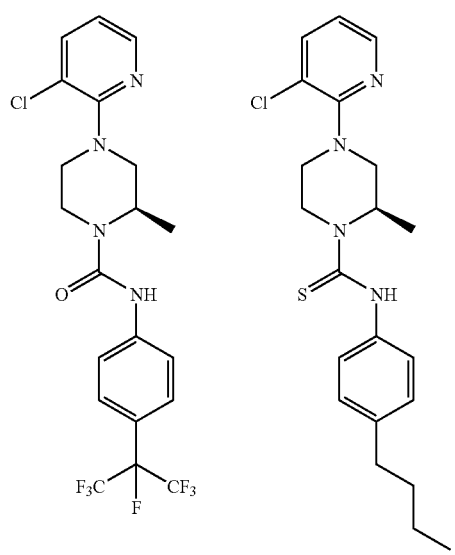
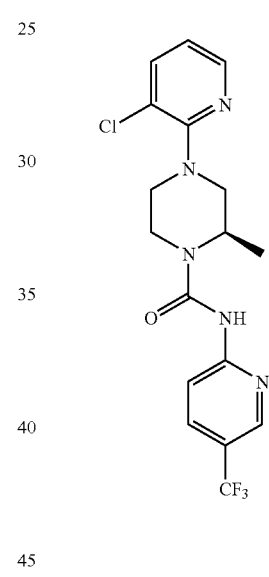
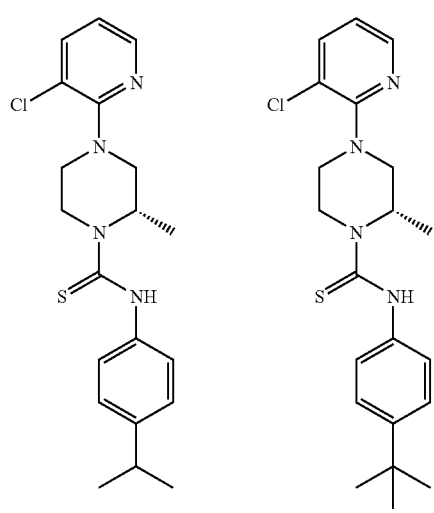
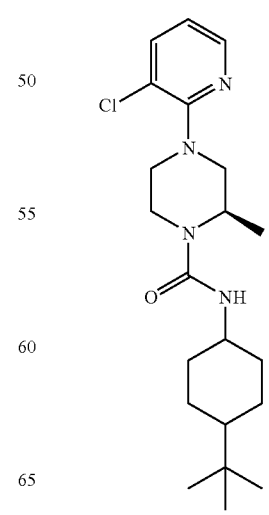

-continued
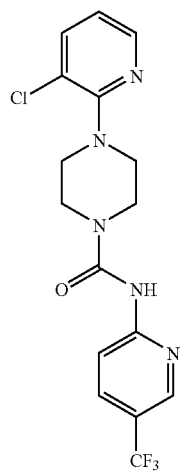 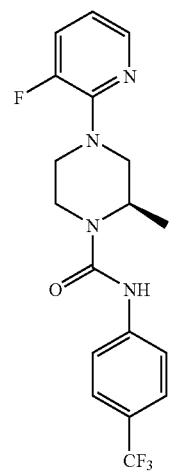 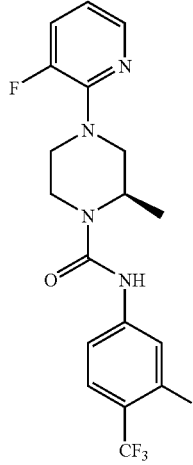 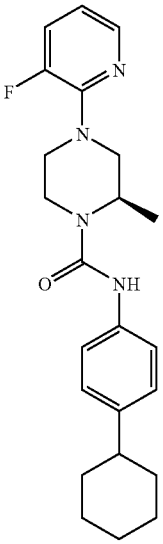
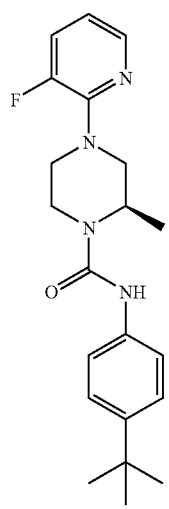 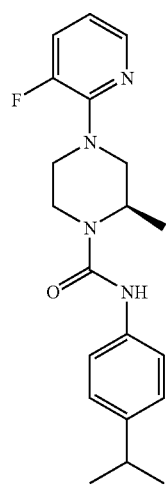 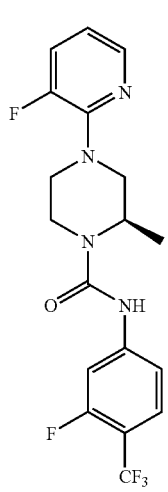 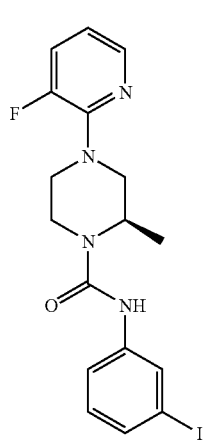
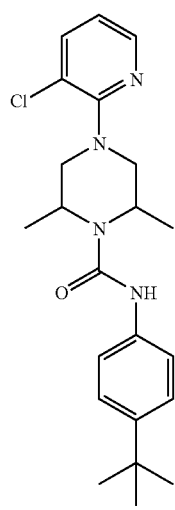 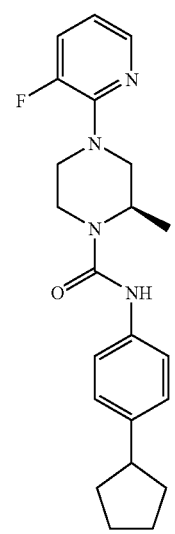

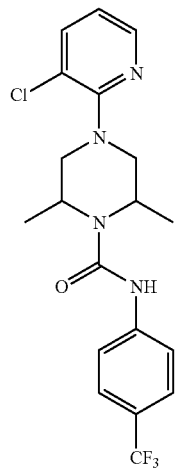
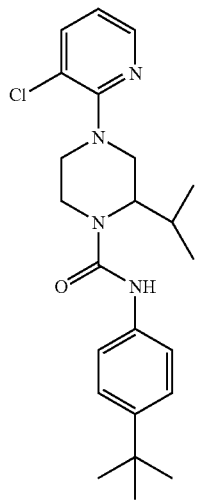
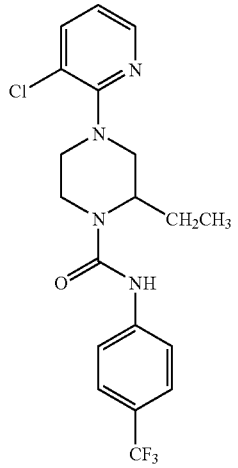
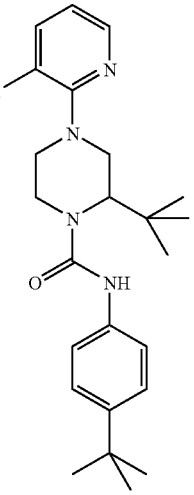
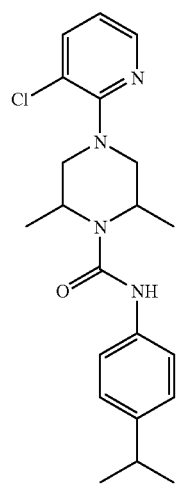
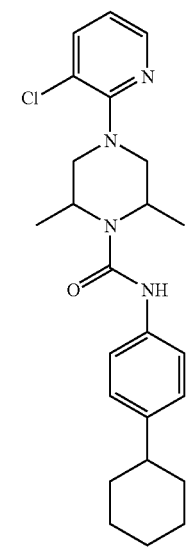
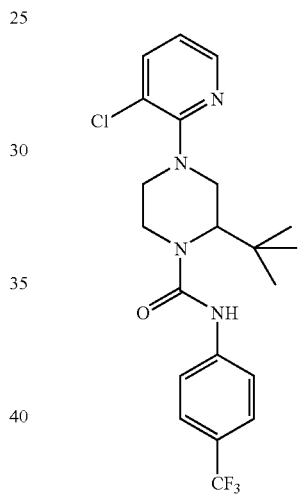
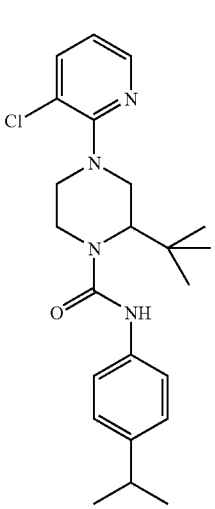
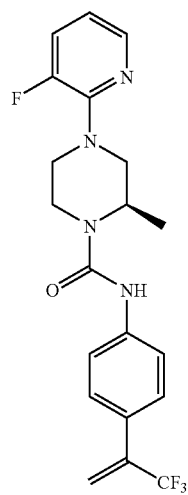
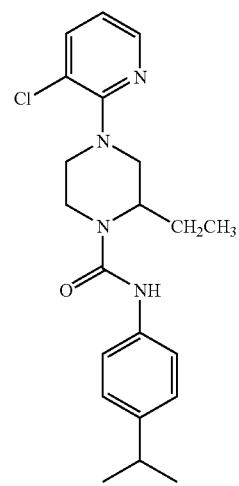
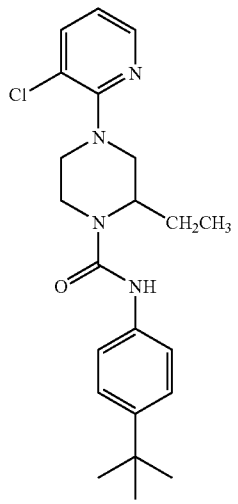
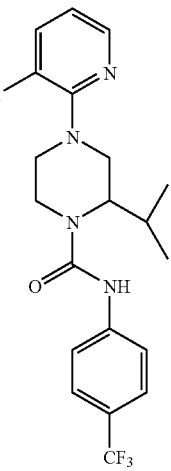

-continued

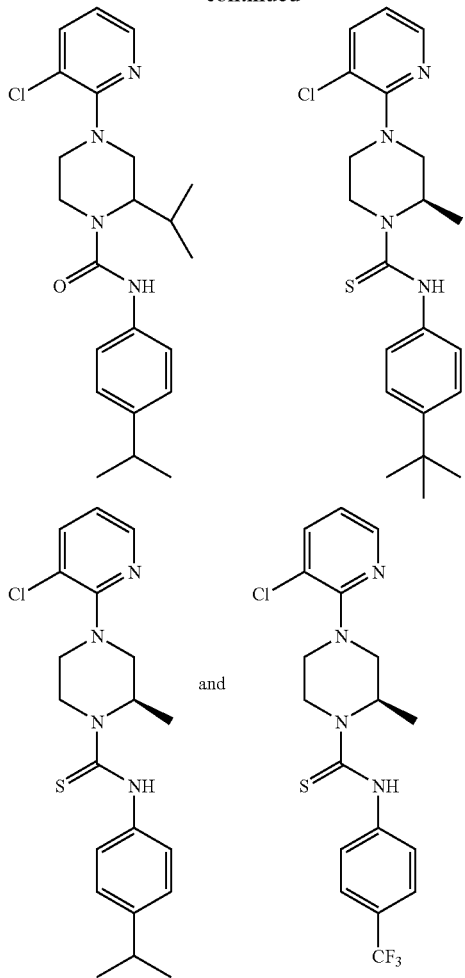

and pharmaceutically acceptable salts thereof.

4.1 Definitions

As used herein, the terms used above having following meaning:

"-Alkyl" means a straight chain or branched non-cyclic hydrocarbon having from 1 to 10 carbon atoms. "—($C_1$-$C_4$) alkyl" means an alkyl group having from 1 and 4 carbon atoms. "—($C_1$-$C_6$)alkyl" means an alkyl group having from 1 and 6 carbon atoms. "—($C_2$-$C_6$)alkyl" means an alkyl group having from 2 and 6 carbon atoms. Representative straight chain alkyls include -methyl, -ethyl, -n-propyl, -n-butyl, -n-pentyl, -n-hexyl, -n-heptyl, -n-octyl, -n-nonly and -n-decyl; while branched alkyls include -isopropyl, -sec-butyl, -isobutyl, -tert-butyl, -isopentyl, 2-methylbutyl, and the like.

"-Alkenyl" means a straight chain or branched non-cyclic hydrocarbon having from 2 to 10 carbon atoms and including at lease one carbon-carbon double bond. "—($C_2$-$C_6$) alkenyl" means an alkenyl group having from 2 to 6 carbon atoms. "—($C_2$-$C_3$)alkenyl" means an alkenyl group having from 2 to 3 carbon atoms. Representative straight chain and branched alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, and the like.

"-Alkynyl" means a straight chain or branched non-cyclic hydrocarbon having from 2 to 10 carbon atoms and including at lease one carbon-carbon triple bond. "—($C_2$-$C_6$) alkynyl" means an alkynyl group having from 2 to 6 carbon atoms. Representative straight chain and branched alkynyls include -acetylenyl, -propynyl, -1-butynyl, -2-butynyl, -1-pentynyl, -2-pentynyl, -3-methyl-1-butynyl, and the like.

"-Cycloalkyl" means a saturated cyclic hydrocarbon having from 3 to 10 carbon atoms. "—($C_3$-$C_8$)cycloalkyl" means a cycloalkyl group having from 3 and 8 carbon atoms. Representative cycloalkyls include -cyclopropyl, -cyclobutyl, -cyclopentyl, -cyclohexyl, -cycloheptyl, -cyclooctyl, -cyclononyl, and -cyclodecyl. Cycloalkyls also include bi- and tri-cyclic ring systems having from 8 to 14 carbon atoms such as a cycloalkyl (such as cyclopentane or cyclohexane) fused to one or more aromatic (such as phenyl) or non-aromatic (such as cyclohexane) carbocyclic rings.

"-Cycloalkenyl" means a cyclic hydrocarbon having at least one carbon-carbon double bond in the cyclic system and from 5 to 10 carbon atoms. "—($C_5$-$C_8$)cycloalkenyl" means a cycloalkenyl group having from 5 and 8 carbon atoms Representative cycloalkenyl include -cyclopentenyl, -cyclopentatienyl, -cyclohexenyl, -cyclohexadienyl, cycloheptenyl, cycloheptadienyl, cycloheptatrienyl, cyclooctenyl, cyclooctadienyl, cyclooctatrienyl, cyclooctatetraenyl, and the like. Cycloalkenyls also include bi- and tri-cyclic ring systems having from 8 to 14 carbon atoms such as a cycloalkenyl (such as cyclopentene or cyclohexene) fused to one or more aromatic (such as phenyl) or non-aromatic (such as cyclohexane) carbocyclic rings.

"-Halogen" or "-Halo" means fluorine, chlorine, bromine or iodine.

"-Aryl" means an aromatic carbocyclic moiety such as phenyl, naphthyl and anthracenyl. "—($C_6$)aryl" means an aryl group having 6 carbon atoms. "—($C_{10}$)aryl" means an aryl group having 10 carbon atoms. "—($C_{14}$)aryl" means an aryl group having 14 carbon atoms.

"-Heteroaryl" means an aromatic heterocycle ring of 5 to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"-Heterocycle" or "-Heterocyclo" means a 3- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. "—($C_3$-$C_5$)heterocycle" means a heterocycle having from 3 and 5 ring atoms. "—($C_3$-$C_7$)heterocycle" means a heterocycle having from 3 and 7 ring atoms. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"-Alkylaryl" means an alkyl having at least one alkyl hydrogen atom replaced with an aryl moiety, defined above. Illustrative -alkylaryl groups include benzyl, —(CH$_2$)$_2$phenyl, —(CH$_2$)$_3$phenyl, —CH(phenyl)$_2$, and the like.

"-Alkylheterocycle" means an alkyl group wherein at least one hydrogen of the alkyl group is substituted with a heterocycle group, defined above.

"-Alkenylaryl" means an alkenyl having at least one hydrogen atom of the alkenyl group replaced with an aryl group, defined above.

"-Alkenylheterocycle" means an alkenyl having at least one hydrogen atom of the alkenyl group replaced with an heterocycle group, defined above.

"-Alkynylcycloalkyl" means an alkynyl having at least one hydrogen atom of the alkynyl group replaced with a cycloalkyl group, defined above.

"-Alkynylcycloalkenyl" means an alkynyl having at least one hydrogen atom of the alkynyl group replaced with a cycloalkenyl group, defined above.

"-Alkynylaryl" means an alkynyl having at least one hydrogen atom of the alkynyl group replaced with an aryl group, defined above.

"-Alkynylheterocycle" means an alkynyl having at least one hydrogen atom of the alkynyl group replaced with a heterocycle group, defined above.

The Piperazine Compounds can have a substituent, for example R$_5$, having a first and a second group. Examples of substiuents having a having a first and a second group are —(C$_3$-C$_8$)cycloalkyl, —(C$_5$-C$_8$)cycloalkenyl, —(C$_6$)aryl, —(C$_{10}$)aryl, —(C$_{14}$)aryl, —(C$_3$-C$_7$)heterocycle, —(C$_1$-C$_6$)alkyl(C$_6$)aryl, —(C$_1$-C$_6$)alkyl(C$_{10}$)aryl, —(C$_1$-C$_6$)alkyl(C$_{14}$)aryl, —(C$_1$-C$_6$)alkyl(C$_3$-C$_7$)heterocycle, —(C$_2$-C$_6$)alkenyl(C$_6$)aryl, —(C$_2$-C$_6$)alkenyl(C$_{10}$)aryl, —(C$_2$-C$_6$)alkenyl(C$_{14}$)aryl, —(C$_2$-C$_6$)alkenyl(C$_3$-C$_7$)heterocycle, —(C$_2$-C$_6$)alkynyl(C$_3$-C$_8$)cycloalkyl, —(C$_2$-C$_6$)alkynyl(C$_5$-C$_8$)cycloalkenyl, —(C$_2$-C$_6$)alkynyl(C$_6$)aryl, —(C$_2$-C$_6$)alkynyl(C$_{10}$)aryl, —(C$_2$-C$_6$)alkynyl(C$_{14}$)aryl, and —(C$_2$-C$_6$)alkynyl(C$_3$-C$_7$)heterocycle., wherein each first and second group is defined above.

Where a substituent includes a first and a second group, for example, —(C$_1$-C$_6$)alkyl(C$_6$)aryl, wherein (C$_1$-C$_6$)alkyl is the first group and (C$_6$)aryl, is the second group, it is to be understood that the first group forms a bond with the Piperazine Compound's backbone and the second group is a substituent of the first group.

"Patient" means an animal, including, but not limited to, a cow, monkey, chimpanzee, baboon, horse, sheep, pig, chicken, turkey, quail, cat, dog, mouse, rat, rabbit, and guinea pig, and is more preferably a mammal, and most, preferably a human.

The phrase "pharmaceutically acceptable salt," as used herein, is a salt formed from an acid and the basic nitrogen group of one of the Piperazine Compounds. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a Piperazine Compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The term "UI" means urinary incontinence.

The term "IBD" means inflammatory-bowel disease.

The term "IBS" means irritable-bowel syndrome.

The term "ALS" means amyotrophic lateral sclerosis.

The phrase "treatment of" and "treating" includes the amelioration or cessation of pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression, or a symptom thereof.

The phrase "prevention of" and "preventing" includes the avoidance of the onset of pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression, or a symptom thereof.

The phrase "effective amount," when used in connection with a Piperazine Compound means an amount effective for: (a) treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression; or (b) inhibiting VR1, mGluR1, or mGluR5 function in a cell.

The phrase "effective amount," when used in connection with the another therapeutic agent means an amount for providing the therapeutic effect of the therapeutic agent.

When a first group is "substituted with one or more" second groups, one or more hydrogen atoms of the first group is replaced with a corresponding number of second groups. When the number of second groups is two or greater, each second group can be the same or different. In one embodiment, the number of second groups is one or two. In another embodiment, the number of second groups is one.

The phrase "pyridyl group", as used herein, means

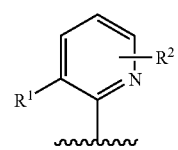

wherein R$^1$ and R$^2$ are defined above for the Piperazine Compounds of formulas (I)-(IX).

The group

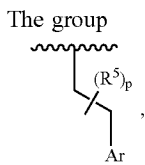

as used herein, means an ethylene group attached to a terminal Ar group, wherein one or each of two of the hydrogens of the ethylene group can optionally be substituted with an $R^5$ group.

The group

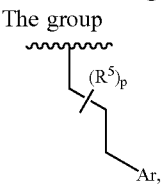

as used herein, means a n-propylene group attached to a terminal Ar group, wherein one or each of two of the hydrogens of the propylene group can optionally be substituted with an $R^5$ group.

It is to be understood that when $R^2$ is —$(CH_2)_nC(O)R^6$, —$(CH_2)_nOR^6$, or —$(CH_2)_nSR^6$; n is 0; and $R^6$ is —H, then $R^2$ is unsubstituted.

4.2 Methods for Making the Piperazine Compounds

The Piperazine Compounds can be obtained using conventional organic syntheses or by the following illustrative methods shown in the scheme below:

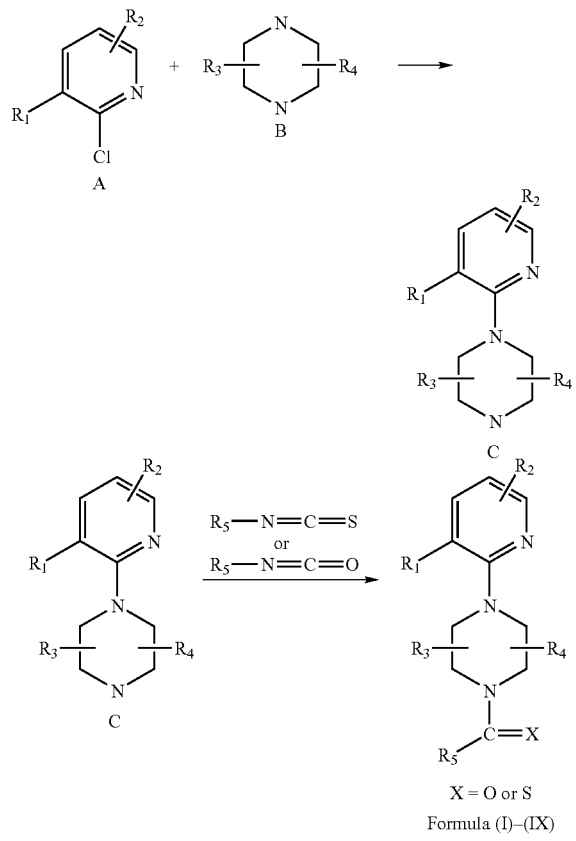

wherein $R_1$, $R_2$, $R_3$, $R_4$, and $R_5$ are as defined above.

Compound A is reacted with Compound B in an aprotic solvent, preferably with heating, to provide Compound C. Suitable aprotic solvents include, but are not limited to, dimethylsulfoxide (DMSO), dimethylformamide (DMF), dichloromethane (DCM), 1,2-dichloroethane, and dioxane. Compound C is isolated from the reaction mixture and purified, preferably using column chromatography or recrystallization. Compound C is then reacted with an isocyanate ($R_5$—N=C=O) or isothiocyanate ($R_5$—N=C=S) in a suitable solvent, preferably dichloromethane, at a suitable temperature, preferably at room temperature, to provide the compound of Formula (I) wherein X=O or X=S, respectively.

If Compound C is substituted with a hydroxyl group or thiol group, then the hydroxyl or thiol group of compound B is preferably protected with a suitable protecting group before being reacted with the isocyanate or isothiocyanate. Suitable protecting groups for hydroxyl group include, but are not limited to, methyl ether, methoxymethyl ether, methoxythiomethyl ether, 2-methoxyethoxymethyl ether, bis(2-chloroethoxy)ethyl ether, tetrahydropyranyl ether, tetrahydrothiopyranyl ether, 4-methoxytetrahydropyranyl ether, methoxytetrahydrothiopyranyl ether, tetrahydrofuranyl ether, tetrahydrothiofuranyl ether, 1-ethoxyethyl ether, 1-methyl-1-methoxyethyl ether, 2-(phenylselenyl ether), t-butyl ether, allyl ether, benzyl ether, o-nitrobenzyl ether, triphenylmethyl ether, o-napthyldiphenylmethyl ether, -methoxydiphenylmethyl ether, 9-(9-phenyl-10-oxo)anthryl ether (tritylone), trimethylsilyl ether, isopropyldimethylsilyl ether, t-butyldimethylsilyl ether, t-butyldiphenylsilyl ether, tribenzylsilyl ether, triisopropylsilyl ether, formate ester, acetate ester, trichloroacetate ester, phenoxyacetate ester, isobutyrate ester, pivaloate ester, adamantoate ester, benzoate ester, 2,4,6-trimethyl (mesitoate) ester, methyl carbonate, 2,2,2-trichlorocarbonate, allyl carbonate, p-nitrophenyl carbonate, benzyl carbonate, p-nitrobenzyl carbonate, S-benzylthiocarbonate, N-phenylcarbamate, nitrate ester, and 2,4-dinitrophenylsulfenate ester (See, e.g., T. W. Greene, *Protective Groups in Organic Synthesis*, John Wiley-Interscience Publication, New York, (1981)).

Suitable protecting groups for thiol group include, but are not limited to, S-benzyl thioether, S-p-methoxybenzyl thioether, S-p-nitrobenzyl thioether, S-4-picolyl thioether, S-2-picolyl N-oxide thioether, S-9-anthrylmethyl thioether, S-diphenylmethyl thioether, S-di(p-methoxyphenyl)methyl thioether, S-triphenylmethyl thioether, S-2,4-dinitrophenyl thioether, S-t-butyl thioether, S-isobutoxymethyl hemithioacetal, S-2tetrahydropyranyl hemithioacetal, S-acetamidomethyl aminothioacetal, S-cyanomethyl thioether, S-2-nitro-1-phenylethyl thioether, S-2,2-bis(carboethoxy)ethyl thioether, S-benzoyl derivative, S-(N-ethylcarbamate), and S-ethyldisulfide. Id.

Compound A wherein $R_1$ is Cl or $CH_3$ is commercially available from Aldrich Chemical Co., Milwaukee, Wis., USA; Compound A wherein $R_1$ is Br is commercially available from Specs B. V., Rijswijk, the Netherlands; and Compound A wherein $R_1$ is I is commercially available from Apollo Scientific Ltd., Derbyshire, United Kingdom. Compound A wherein $R_1$ is F can be obtained by combining 3-amino 2-chloropyridine (commercially available from Aldrich Chemical Co., Milwaukee, Wis.) with HF in pyridine at 0° C., adding 1.3 eq. (based on 3-amino 2-chloropyridine) of $NaNO_2$, allowing the reaction mixture to warm up to 40-45° C., and maintaining the reaction mixture at 40-45° C. for from 10 and 30 minutes.

Isocyanates $R_5$—N=C=O are commercially available or preparable by reacting $R_5NH_2$ with phosgene according to well-known methods (See, e.g., H. Eckert and B. Foster, *Angew. Chem. Int. Ed. Engl.*, 26, 894 (1987); H. Eckert, Ger. Offen. DE 3 440 141; *Chem Abstr.* 106, 4294d, (1987); and L. Contarca et al., *Synthesis*, 553-576 (1996)). For example an amine, $R_5$—$NH_2$ can be reacted with triphosgene according to the scheme shown below.

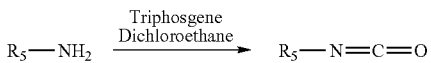

Typically, a solution of triphosgene (0.3 eq) in 1,2-dichloromethane (0.3 M) is slowly added to a stirred solution of the amine (1.0 eq.) in 1,2-dichloroethane (0.3 M) at room temperature. The reaction mixture is then stirred at room temperature for 10 min. and the temperature then raised to 70° C. After stirring at 70° C. for 3 h., the reaction mixture is cooled to room temperature, filtered, and the filtrate concentrated to give the desired isocyanate.

Isothiocyanates $R_5$—N=C=S are commercially available or preparable by reacting $R_5NH_2$ with thiophosgene as shown in the scheme below (See, e.g., *Tetrahedron. Lett.*, 41 (37), 7207-7209 (2000); *Synlett*, (11), 1784-1786 (1999); *Heterocycles*, 32, 2343-2355 (1991); *Org. Prep., Proced., Int.*, 23 (6), 729-734 (1991); *J. Heterocycle Chem.*, 28 (4), 1091-1097 (1991); *J. Fluorine Chem.*, 41 (3), 303-310 (1988); and *J. Med. Chem.*, 32 (6) 1173-1176 and 1392-1398 (1989); and Tett. Lett., 42 (32), 5414-5416 (2001).

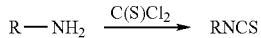

Alternatively, isothiocyanates $R_5$—N=C=S can be prepared by reacting $R_5NH2$, with carbon disulfide in the presence of triethylamine in tetrahydrofuran, followed by reaction with hydrogen peroxide and hydrochloric acid in water as shown in the scheme below (See, e.g., J. Org. Chem., 62 (13), 4539-4540 (1997)).

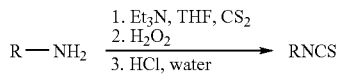

The Piperazine Compounds can also be prepared by reacting $R_5NH_2$ with 4-nitophenyl chloroformate (commercially available from Aldrich Chemical Co. of Milwaukee, Wis.) to provide a carbamate, Compound D, and then reacting Compound D with Compound C as shown in the scheme below (See, e.g., *J. Org. Chem.*, 63(23), 8515-8521, (1998) and European Patent Publication No. 549 039).

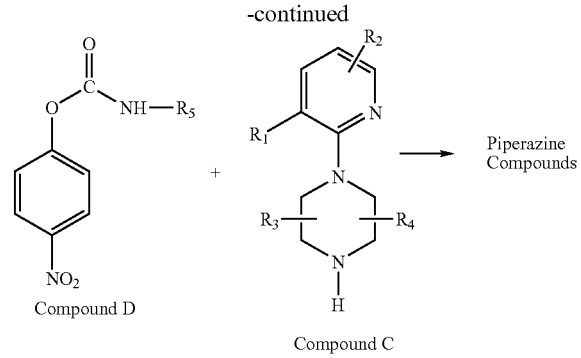

Compound D

-continued

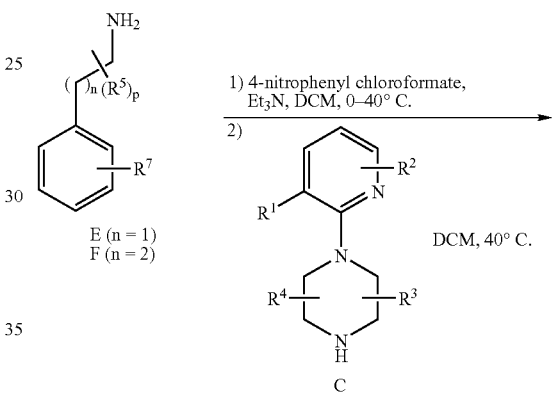

Compound C

The scheme below illustrates methods for making the Piperazine Compounds of formula (VIII) or (IX). These Compounds can be prepared by reacting Compound C with a phenethylamine Compound E or a phenpropylamine Compound of formula F using 4-nitrophenyl chloroformate as described above.

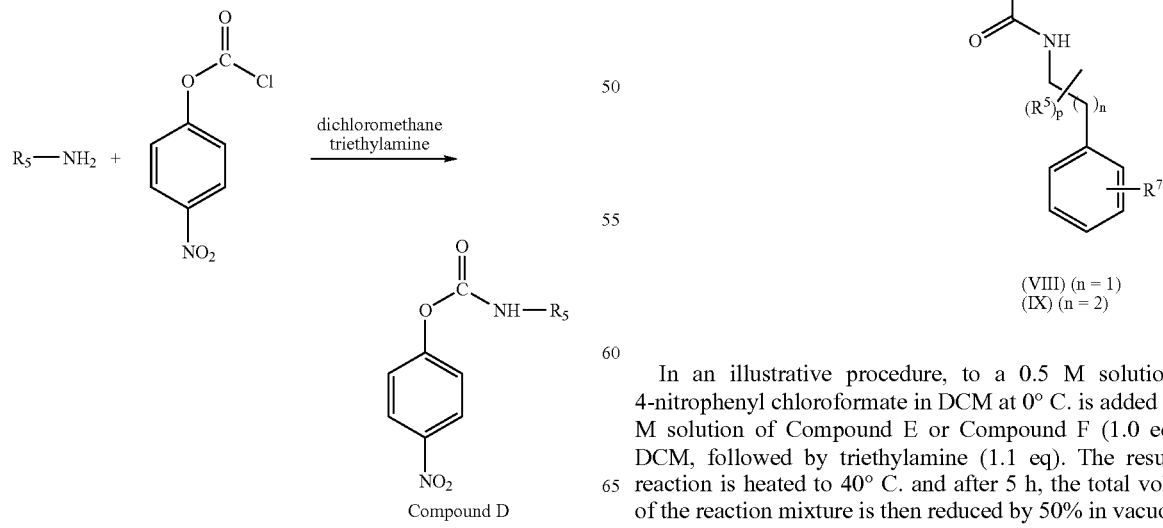

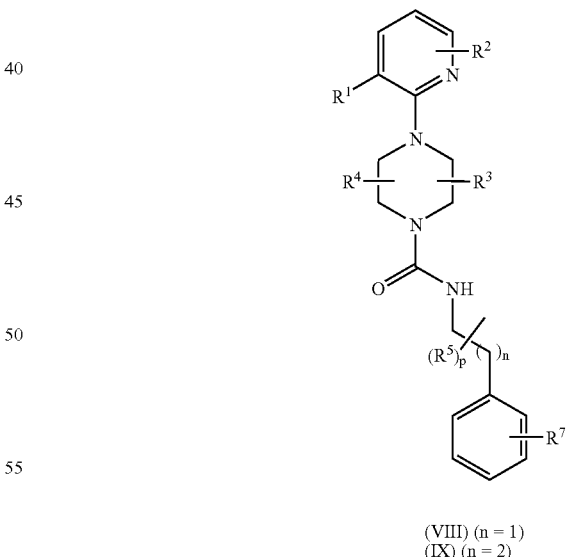

(VIII) (n = 1)
(IX) (n = 2)

In an illustrative procedure, to a 0.5 M solution of 4-nitrophenyl chloroformate in DCM at 0° C. is added a 0.5 M solution of Compound E or Compound F (1.0 eq) in DCM, followed by triethylamine (1.1 eq). The resulting reaction is heated to 40° C. and after 5 h, the total volume of the reaction mixture is then reduced by 50% in vacuo and Compound C is added. The reaction mixture is stirred for 1 h at 40° C., then concentrated in vacuo to provide a crude residue that is purified using flash column chromatography (gradient elution from 100% hexanes to 20% hexanes/EtOAc using a 5% gradient) to provide the corresponding compound of formula (VIII) or (IX).

The urea or thiourea nitrogen atom of $R_5$ of the Piperazine Compounds can be alkylated using sodium hydride in an anhydrous aprotic solvent followed by reaction with an alkyl halide, such as methyl iodide.

Certain Piperazine Compounds can have one or more asymmetric centers and therefore exist in different enantiomeric and diastereomeric forms. A Piperazine Compound can be in the form of an optical isomer or a diastereomer. Accordingly, the invention encompasses Piperazine Compounds and their uses as described herein in the form of their optical isomers, diasteriomers, and mixtures thereof, including a racemic mixture.

In addition, one or more hydrogen, carbon or other atoms of a Piperazine Compound can be replaced by an isotope of the hydrogen, carbon or other atoms. Such compounds, which are encompassed by the present invention, are useful as research and diagnostic tools in metabolism pharmacokinetic studies and in binding assays.

In the Piperazine Compounds the $R^3$ group can be on any carbon of the piperazine ring. In one embodiment, $R^3$ is a group other than hydrogen and the $R^3$ group is attached to a carbon atom adjacent to the nitrogen atom attached to the pyridyl group. In another embodiment, $R^3$ is a group other than hydrogen and the $R^3$ group is attached to a carbon atom adjacent to the nitrogen atom attached to the —C(=O)—NHR$_5$; —C(=S)—NHR$_5$; —C(=O)—NH(CH$_2$)$_2$Ar group, optionally substituted with one or two $R^5$ groups; or —C(=O)—NH(CH$_2$)$_3$Ar group optionally substituted with one or two $R^5$ groups.

In another embodiment, the Piperazine Compound has an $R^3$ group that is other than hydrogen and the carbon atom to which the $R^3$ group is attached has the (R) configuration. In another embodiment, the Piperazine Compound has an $R^3$ group that is other than hydrogen and the carbon atom to which the $R^3$ group is attached has the (S) configuration.

In another embodiment, the Piperazine Compound has an $R^3$ group that is other than hydrogen, the $R^3$ group is attached to a carbon atom adjacent to a nitrogen atom attached to the pyridyl group, and the carbon atom to which the $R^3$ group is attached has the (R) configuration. In another embodiment, the Piperazine Compound has an $R^3$ group other than hydrogen, the $R^3$ group is attached to a carbon atom adjacent to a nitrogen attached to the pyridyl group, the carbon atom to which the $R^3$ group is attached has the (R) configuration, and $R^3$ is —(C$_1$-C$_4$)alkyl unsubstituted or substituted with one or more halo groups. In another embodiment, the Piperazine Compound has an $R^3$ group other than hydrogen, the $R^3$ group is attached to a carbon atom adjacent to a nitrogen attached to the pyridyl, the carbon atom to which the $R^3$ group is attached has the (R) configuration, and $R^3$ is —CH$_3$. In another embodiment, the Piperazine Compound has an $R^3$ group other than hydrogen, the $R^3$ group is attached to a carbon atom adjacent to a nitrogen attached to the pyridyl group, the carbon atom to which the $R^3$ group is attached has the (R) configuration, and $R^3$ is —CF$_3$. In another embodiment, the Piperazine Compound has an $R^3$ group other than hydrogen, the $R^3$ group is attached to a carbon atom adjacent to a nitrogen attached to the pyridyl group, the carbon atom to which the $R^3$ group is attached has the (R) configuration, and $R^3$ is —CH$_2$CH$_3$.

In another embodiment, the Piperazine Compound has an $R^3$ group that is other than hydrogen, the $R^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two $R^5$ groups; or —C(=O)—NH(CH$_2$)$_3$Ar group, optionally substituted with one or two $R^5$ groups; and the carbon atom to which the $R^3$ group is attached has the (R) configuration. In another embodiment, the Piperazine Compound has an $R^3$ group other than hydrogen, the $R^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two $R^5$ groups; or —C(=O)—NH(CH$_2$)$_3$Ar group, optionally substituted with one or two $R^5$ groups; the carbon atom to which the $R^3$ group is attached has the (R) configuration, and $R^3$ is —(C$_1$-C$_4$)alkyl unsubstituted or substituted with one or more halo groups. In another embodiment, the Piperazine Compound has an $R^3$ group other than hydrogen, the $R^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two $R^5$ groups; or —C(=O)—NH(CH$_2$)$_3$Ar group, optionally substituted with one or two $R^5$ groups; the carbon atom to which the $R^3$ group is attached has the (R) configuration, and $R^3$ is —CH$_3$. In another embodiment, the Piperazine Compound has an $R^3$ group other than hydrogen, the $R^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two $R^5$ groups; or —C(=O)—NH(CH$_2$)$_3$Ar group, optionally substituted with one or two $R^5$ groups; the carbon atom to which the $R^3$ group is attached has the (R) configuration, and $R^3$ is —CF$_3$. In another embodiment, the Piperazine Compound has an $R^3$ group other than hydrogen, the $R^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two $R^5$ groups; or —C(=O)—NH(CH)$_3$Ar group, optionally substituted with one or two $R^5$ groups; the carbon atom to which the $R^3$ group is attached has the (R) configuration, and $R^3$ is —CH$_2$CH$_3$.

In another embodiment, the Piperazine Compound has an $R^3$ group that is other than hydrogen, the $R^3$ group is attached to a carbon atom adjacent to a nitrogen atom attached to the pyridyl group, and the carbon atom to which the $R^3$ group is attached has the (S) configuration. In another embodiment, the Piperazine Compound has an $R^3$ group other than hydrogen, the $R^3$ group is attached to a carbon atom adjacent to a nitrogen attached to the pyridyl group, the carbon atom to which the $R^3$ group is attached has the (S) configuration, and $R^3$ is —(C$_1$-C$_4$)alkyl unsubstituted or substituted with one or more halo groups. In another embodiment, the Piperazine Compound has an $R^3$ group other than hydrogen, the $R^3$ group is attached to a carbon atom adjacent to a nitrogen attached to the pyridyl, the carbon atom to which the $R^3$ group is attached has the (S) configuration, and $R^3$ is —CH$_3$. In another embodiment, the Piperazine Compound has an $R^3$ group other than hydrogen, the $R^3$ group is attached to a carbon atom adjacent to a nitrogen attached to the pyridyl group, the carbon atom to which the $R^3$ group is attached has the (S) configuration, and $R^3$ is —CF$_3$. In another embodiment, the Piperazine Compound has an $R^3$ group other than hydrogen, the $R^3$ group is attached to a carbon atom adjacent to a nitrogen attached to the pyridyl group, the carbon atom to which the $R^3$ group is attached has the (S) configuration, and $R^3$ is —CH$_2$CH$_3$.

In another embodiment, the Piperazine Compound has an R$^3$ group that is other than hydrogen, the R$^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two R$^5$ groups; or —C(=O)—NH(CH$_2$)$_3$Ar group, optionally substituted with one or two R$^5$ groups; and the carbon atom to which the R$^3$ group is attached has the (S) configuration. In another embodiment, the Piperazine Compound has an R$^3$ group other than hydrogen, the R$^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two R$^5$ groups; or —C(=O)—NH(CH$_2$)$_3$Ar group, optionally substituted with one or two R$^5$ groups; the carbon atom to which the R$^3$ group is attached has the (S) configuration, and R$^3$ is —(C$_1$-C$_4$)alkyl unsubstituted or substituted with one or more halo groups. In another embodiment, the Piperazine Compound has an R$^3$ group other than hydrogen, the R$^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two R$^5$ groups; or —C(=O)—NH(CH$_2$)$_3$Ar group, optionally substituted with one or two R$^5$ groups; the carbon atom to which the R$^3$ group is attached has the (S) configuration, and R$^3$ is —CH$_3$. In another embodiment, the Piperazine Compound has an R$^3$ group other than hydrogen, the R$^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two R$^5$ groups; or —C(=O)—NH(CH$_2$)$_3$Ar group, optionally substituted with one or two R$^5$ groups; the carbon atom to which the R$^3$ group is attached has the (S) configuration, and R$^3$ is —CF$_3$. In another embodiment, the Piperazine Compound has an R$^3$ group other than hydrogen, the R$^3$ group is attached to a carbon atom adjacent to a nitrogen atom attached to the —C(=O)—NHR$_5$; —C(=S)—NHR$_5$; —C(=O)—NH(CH$_2$)$_2$Ar group, optionally substituted with one or two R$^5$ groups; or —C(=O)—NH(CH$_2$)$_3$Ar group, optionally substituted with one or two R$^5$ groups; the carbon atom to which the R$^3$ group is attached has the (S) configuration, and R$^3$ is —CH$_2$CH$_3$.

4.3 Therapeutic Uses of the Piperazine Compounds

In accordance with the invention, the Piperazine Compounds are administered to an animal in need of treatment or prevention of pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression.

In one embodiment, an effective amount of a Piperazine Compound can be used to treat or prevent any condition treatable or preventable by inhibiting VR1. Examples of conditions that are treatable or preventable by inhibiting VR1 include, but are not limited to, pain, UI, an ulcer, IBD, and IBS.

In another embodiment, an effective amount of a Piperazine Compound can be used to treat or prevent any condition treatable or preventable by inhibiting mGluR5. Examples of conditions that are treatable or preventable by inhibiting mGluR5 include, but are not limited to, pain, an addictive disorder, Parkinson's disease, parkinsonism, anxiety, a pruritic condition, and psychosis.

In another embodiment, an effective amount of a Piperazine Compound can be used to treat or prevent any condition treatable or preventable by inhibiting mGluR1. Examples of conditions that are treatable or preventable by inhibiting mGluR1 include, but are not limited to, pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, and depression.

The Piperazine Compounds can be used to treat or prevent acute or chronic pain. Examples of pain treatable or preventable using the Piperazine Compounds include, but are not limited to, cancer pain, central pain, labor pain, myocardial infarction pain, pancreatic pain, colic pain, post-operative pain, headache pain, muscle pain, pain associated with intensive care, arthritic pain, and pain associated with a periodontal disease, including gingivitis and periodontitis.

The Piperazine Compounds can be used to treat or prevent UI. Examples of UI treatable or preventable using the Piperazine Compounds include, but are not limited to, urge incontinence, stress incontinence, overflow incontinence, neurogenic incontinence, and total incontinence.

The Piperazine Compounds can be used to treat or prevent an ulcer. Examples of ulcers treatable or preventable using the Piperazine Compounds include, but are not limited to, a duodenal ulcer, a gastric ulcer, a marginal ulcer, an esophageal ulcer, or a stress ulcer.

The Piperazine Compounds can be used to treat or prevent IBD, including Crohn's disease and ulcerative colitis.

The Piperazine Compounds can be used to treat or prevent IBS. Examples of IBS treatable or preventable using the Piperazine Compounds include, but are not limited to, spastic-colon-type IBS and constipation-predominant IBS.

The Piperazine Compounds can be used to treat or prevent an addictive disorder, including but not limited to, an eating disorder, an impulse-control disorder, an alcohol-related disorder, a nicotine-related disorder, an amphetamine-related disorder, a cannabis-related disorder, a cocaine-related disorder, an hallucinogen-related disorder, an inhalant-related disorders, and an opioid-related disorder, all of which are further sub-classified as listed below.

Eating disorders include, but are not limited to, Bulimia Nervosa, Nonpurging Type; Bulimia Nervosa, Purging Type; Anorexia; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder with delusions, Alcohol Abuse, Alcohol Intoxication, Alcohol Withdrawal, Alcohol Intoxication Delirium, Alcohol Withdrawal Delirium, Alcohol-Induced Persisting Dementia, Alcohol-Induced Persisting Amnestic Disorder, Alcohol Dependence, Alcohol-Induced Psychotic Disorder with hallucinations, Alcohol-Induced Mood Disorder, Alcohol-Induced Anxiety Disorder, Alcohol-Induced Sexual Dysfunction, Alcohol-Induced Sleep Disorder, Alcohol-Related Disorder not otherwise specified (NOS), Alcohol Intoxication, and Alcohol Withdrawal.

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

*Cannabis*-related disorders include, but are not limited to, *Cannabis* Dependence, *Cannabis* Abuse, *Cannabis* Intoxication, *Cannabis* Intoxication Delirium, *Cannabis*-Induced Psychotic Disorder with delusions, *Cannabis*-Induced Psychotic Disorder with hallucinations, *Cannabis*-Induced Anxiety Disorder, *Cannabis* Related Disorder not otherwise specified (NOS), and *Cannabis* Intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine Related Disorder not otherwise specified (NOS), Cocaine Intoxication, and Cocaine Withdrawal.

Hallucinogen-related disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence, Inhalant Abuse, Inhalant Intoxication, Inhalant Intoxication Delirium, Inhalant-Induced Psychotic Disorder with delusions, Inhalant-Induced Psychotic Disorder with hallucinations, Inhalant-Induced Anxiety Disorder, Inhalant Related Disorder not otherwise specified (NOS), and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder with delusions, Opioid-Induced Psychotic Disorder with hallucinations, Opioid-Induced Anxiety Disorder, Opioid Related Disorder not otherwise specified (NOS), Opioid Intoxication, and Opioid Withdrawal.

The Piperazine Compounds can be used to treat or prevent Parkinson's disease and parkinsonism and the symptoms associated with Parkinson's disease and parkinsonism, including but not limited to, bradykinesia, muscular rigidity, resting tremor, and impairment of postural balance.

The Piperazine Compounds can be used to treat or prevent generalized anxiety or severe anxiety and the symptoms associated with anxiety, including but not limited to, restlessness; tension; tachycardia; dyspnea; depression, including chronic "neurotic" depression; panic disorder; agoraphobia and other specific phobias; eating disorders; and personality disorders.

The Piperazine Compounds can be used to treat or prevent epilepsy, including but not limited to, partial epilepsy, generalized epilepsy, and the symptoms associated with epilepsy, including but not limited to, simple partial seizures, jacksonian seizures, complex partial (psychomotor) seizures, convulsive seizures (grand mal or tonic-clonic seizures), petit mal (absence) seizures, and status epilepticus.

The Piperazine Compounds can be used to treat or prevent strokes, including but not limited to, ischemic strokes and hemorrhagic strokes.

The Piperazine Compounds can be used to treat or prevent a seizure, including but not limited to, infantile spasms, febrile seizures, and epileptic seizures.

The Piperazine Compounds can be used to treat or prevent a pruritic condition, including but not limited to, pruritus caused by dry skin, scabies, dermatitis, herpetiformis, atopic dermatitis, pruritus vulvae et ani, miliaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, or fiberglass dermatitis.

The Piperazine Compounds can be used to treat or prevent psychosis, including but not limited to, schizophrenia, including paranoid schizophrenia, hebephrenic or disorganized schizophrenia, catatonic schizophrenia, undifferentiated schizophrenia, negative or deficit subtype schizophrenia, and non-deficit schizophrenia; a delusional disorder, including erotomanic subtype delusional disorder, grandiose subtype delusional disorder, jealous subtype delusional disorder, persecutory subtype delusional disorder, and somatic subtype delusional disorder; and brief psychosis.

The Piperazine Compounds can be used to treat or prevent a cognitive disorder, including but not limited to, delirium and dementia such as multi-infarct dementia, dementia pugilistica, dimentia caused by AIDS, and dementia caused by Alzheimer's disease.

The Piperazine Compounds can be used to treat or prevent a memory deficiency, including but not limited to, dissociative amnesia and dissociative fugue.

The Piperazine Compounds can be used to treat or prevent restricted brain function, including but not limited to, that caused by surgery or an organ transplant, restricted blood supply to the brain, a spinal cord injury, a head injury, hypoxia, cardiac arrest, or hypoglycemia.

The Piperazine Compounds can be used to treat or prevent Huntington's chorea.

The Piperazine Compounds can be used to treat or prevent ALS.

The Piperazine Compounds can be used to treat or prevent retinopathy, including but not limited to, arteriosclerotic retinopathy, diabetic arteriosclerotic retinopathy, hypertensive retinopathy, non-proliferative retinopathy, and proliferative retinopathy.

The Piperazine Compounds can be used to treat or prevent a muscle spasm.

The Piperazine Compounds can be used to treat or prevent a migraine.

The Piperazine Compounds can be used to treat or prevent vomiting, including but not limited to, nausea vomiting, dry vomiting (retching), and regurgitation.

The Piperazine Compounds can be used to treat or prevent dyskinesia, including but not limited to, tardive dyskinesia and biliary dyskinesia.

The Piperazine Compounds can be used to treat or prevent depression, including but not limited to, major depression and bipolar disorder.

Applicants believe that the Piperazine Compounds are antagonists for VR1.

The invention also relates to methods for inhibiting VR1 function in a cell comprising contacting a cell capable of expressing VR1 with an effective amount of a Piperazine Compound. This method can be used in vitro, for example, as an assay to select cells that express VR1 and, accordingly, are useful as part of an assay to select compounds useful for treating or preventing pain, UI, an ulcer, IBD, or IBS. The method is also useful for inhibiting VR1 function in a cell in vivo, in an animal, a human in one embodiment, by contacting a cell, in an animal, with an effective amount of a Piperazine Compound. In one embodiment, the method is useful for treating or preventing pain in an animal. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing VR1 include, but are not limited to, neuronal, brain, kidney, urothelium, and bladder tissue. Methods for assaying cells that express VR1 are well known in the art.

Applicants believe that the Piperazine Compounds are antagonists for mGluR5.

The invention also relates to methods for inhibiting mGluR5 function in a cell comprising contacting a cell capable of expressing mGluR5 with an amount of a Piperazine Compound effective to inhibit mGluR5 function in the cell. This method can be used in vitro, for example, as an assay to select cells that express mGluR5 and, accordingly, are useful as part of an assay to select compounds useful for treating or preventing pain, an addictive disorder, Parkinson's disease, parkinsonism, anxiety, a pruritic condition, or psychosis. The method is also useful for inhibiting mGluR5 function in a cell in vivo, in an animal, a human in one embodiment, by contacting a cell, in an animal, with an amount of a piperazine Compound effective to inhibit mGluR5 function in the cell. In one embodiment, the method is useful for treating or preventing pain in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing a pruritic condition in an animal in need thereof. In another embodiment, the method is useful for treating or preventing psychosis in an animal in need thereof.

Examples of cells capable of expressing mGluR5 are neuronal and glial cells of the central nervous system, particularly the brain, especially in the nucleus accumbens. Methods for assaying cells that express mGluR5 are well known in the art.

Applicants believe that the Piperazine Compounds are antagonists for mGluR1.

The invention also relates to methods for inhibiting mGluR1 function in a cell comprising contacting a cell capable of expressing mGluR1 with an amount of a Piperazine Compound effective to inhibit mGluR1 function in the cell. This method can be used in vitro, for example, as an assay to select cells that express mGluR1 and, accordingly, are useful as part of an assay to select compounds useful for treating or preventing pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression. The method is also useful for inhibiting mGluR1 function in a cell in vivo, in an animal, a human in one embodiment, by contacting a cell, in an animal, with an amount of a Piperazine Compound effective to inhibit mGluR1 function in the cell. In one embodiment, the method is useful for treating or preventing pain in an animal in need thereof. In another embodiment, the method is useful for treating or preventing UI in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing epilepsy in an animal in need thereof. In another embodiment, the method is useful for treating or preventing stroke in an animal in need thereof. In another embodiment, the method is useful for treating or preventing a seizure in an animal in need thereof. In another embodiment, the method is useful for treating or preventing a pruritic condition in an animal in need thereof. In another embodiment, the method is useful for treating or preventing psychosis in an animal in need thereof. In another embodiment, the method is useful for treating or preventing a cognitive disorder in an animal in need thereof. In another embodiment, the method is useful for treating or preventing a memory deficit in an animal in need thereof. In another embodiment, the method is useful for treating or preventing restricted brain function in an animal in need thereof. In another embodiment, the method is useful for treating or preventing Huntington's chorea in an animal in need thereof. In another embodiment, the method is useful for treating or preventing ALS in an animal in need thereof. In another embodiment, the method is useful for treating or preventing dementia in an animal in need thereof. In another embodiment, the method is useful for treating or preventing retinopathy in an animal in need thereof. In another embodiment, the method is useful for treating or preventing a muscle spasm in an animal in need thereof. In another embodiment, the method is useful for treating or preventing a migraine in an animal in need thereof. In another embodiment, the method is useful for treating or preventing vomiting in an animal in need thereof. In another embodiment, the method is useful for treating or preventing dyskinesia in an animal in need thereof. In another embodiment, the method is useful for treating or preventing depression in an animal in need thereof.

Examples of cells capable of expressing mGluR1 include, but are not limited to, cerebellar Purkinje neuron cells, Purkinje cell bodies (punctate), cells of spine(s) of the cerebellum; neurons and neurophil cells of olfactory-bulb glomeruli; cells of the superficial layer of the cerebral cortex; hippocampus cells; thalamus cells; superior colliculus cells; and spinal trigeminal nucleus cells. Methods for assaying cells that express mGluR1 are well known in the art.

4.3.1 Therapeutic/Prophylactic Administration and Compositions of the Invention Due to their activity, the Piperazine Compounds are advantageously useful in veterinary and human medicine. As described above, the Piperazine Compounds are useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal in need thereof.

When administered to an animal, the Piperazine Compounds are administered as a component of a composition that comprises a pharmaceutically acceptable carrier or excipient. The present compositions, which comprise a Piperazine Compound, can be administered orally. The Piperazine Compounds of the invention can also be administered by any other convenient route, for example, by infusion or bolus injection, by absorption through epithelial or mucocutaneous linings (e.g., oral, rectal, and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer the Piperazine Compound.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the Piperazine Compounds into the bloodstream.

In specific embodiments, it can be desirable to administer the Piperazine Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Piperazine Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Piperazine Compounds can be formulated as a suppository, with traditional binders and excipients such as triglycerides.

In another embodiment, the Piperazine Compounds can be delivered in a vesicle, in particular a liposome (see Langer, *Science* 249:1527-1533 (1990) and Treat et al., *Liposomes in the Therapy of Infectious Disease and Cancer* 317-327 and 353-365 (1989)).

In yet another embodiment, the Piperazine Compounds can be delivered in a controlled-release system or sustained-release system (see, e.g., Goodson, in Medical Applications of Controlled Release, supra, vol. 2, pp. 115-138 (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (*see Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228: 190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of the Piperazine Compounds, e.g., the spinal column, brain, or gastrointestinal tract, thus requiring only a fraction of the systemic dose.

The present compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water is a particularly useful excipient when the Piperazine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the Piperazine Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Piperazine Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the Piperazine Compounds are to be administered by infusion, they can be dispensed, for example, with an infusion bottle containing sterile pharmaceutical grade water or saline. Where the Piperazine Compounds are administered by injection, an ampule of sterile water for injection or saline can be provided so that the ingredients can be mixed prior to administration.

The Piperazine Compounds can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained counterparts. In one embodiment, a controlled- or sustained-release composition comprises a minimal amount of a Piperazine Compound to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Piperazine Compound, and can thus reduce the occurrence of adverse side effects.

Controlled- or sustained-release compositions can initially release an amount of a Piperazine Compound that promptly produces the desired therapeutic or prophylactic effect, and gradually and continually release other amounts of the Piperazine Compound to maintain this level of therapeutic or prophylactic effect over an extended period of time. To maintain a constant level of the Piperazine Compound in the body, the Piperazine Compound can be released from the dosage form at a rate that will replace the amount of Piperazine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Piperazine Compound that is effective in the treatment or prevention of pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression and can be determined by standard clinical techniques. In addition, in vitro or in vivo assays can optionally be employed to help identify optimal dosage ranges. The precise dose to be employed will also depend on the route of administration, and the seriousness of the condition being treated and should be decided according to the judgment of the practitioner and each patient's circumstances in view of, e.g., published clinical studies. Suitable effective dosage amounts, however, range from about 10 micrograms to about 2500 milligrams about every 4 h, although they are typically about 100 mg or less. In one embodiment, the effective dosage amount ranges from about 0.01 milligrams to about 100 milligrams of a Piperazine Compound about every 4 h, in another embodiment, about 0.020 milligrams to about 50 milligrams about every 4 h, and in another embodiment, about 0.025 milligrams to about 20 milligrams about every 4 h. The effective dosage amounts described herein refer to total amounts administered; that is, if more than one Piperazine Compound is administered, the effective dosage amounts correspond to the total amount administered.

Where a cell capable of expressing VR1, mGluR5, or mGluR1 is contacted with a Piperazine Compound in vitro, the amount effective for inhibiting the receptor function in a cell will typically range from about 0.01 μg/L to about 5 mg/L, in one embodiment, from about 0.01 μg/L to about 2.5 mg/L, in another embodiment, from about 0.01 μg/L to about 0.5 mg/L, and in another embodiment, from about 0.01 μg/L to about 0.25 mg/L of a solution or suspension of a pharmaceutically acceptable carrier or excipient. In one embodiment, the volume of solution or suspension is from about 1 μL to about 1 mL. In another embodiment, the volume of solution or suspension is about 200 μL.

Where a cell capable of expressing VR1, mGluR5, or mGluR1 is contacted with a Piperazine Compound in vivo, the amount effective for inhibiting the receptor function in a cell will typically range from about 0.01 mg to about 100 mg/kg of body weight per day, in one embodiment, from about 0.1 mg to about 50 mg/kg body weight per day, and in another embodiment, from about 1 mg to about 20 mg/kg of body weight per day.

The Piperazine Compounds can be assayed in vitro or in vivo for the desired therapeutic or prophylactic activity prior to use in humans. Animal model systems can be used to demonstrate safety and efficacy.

The present methods for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal in need thereof can further comprise administering to the animal being administered a Piperazine Compound another therapeutic agent. In one embodiment, the other therapeutic agent is administered in an effective amount.

The present methods for inhibiting VR1 function in a cell capable of expressing VR1 can further comprise contacting the cell with an effective amount of another therapeutic agent.

The present methods for inhibiting mGluR5 function in a cell capable of expressing mGluR5 can further comprise contacting the cell with an effective amount of another therapeutic agent.

The present methods for inhibiting mGluR1 function in a cell capable of expressing mGluR1 can further comprise contacting the cell with an effective amount of another therapeutic agent.

The other therapeutic agent includes, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a Ca2+-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, or an agent for treating depression, and mixtures thereof.

Effective amounts of the other therapeutic agents are well known to those skilled in the art. However, it is well within the skilled artisan's purview to determine the other therapeutic agent's optimal effective-amount range. In one embodiment of the invention, where another therapeutic agent is administered to an animal, the effective amount of the Piperazine Compound is less than its effective amount would be where the other therapeutic agent is not administered. In this case, without being bound by theory, it is believed that the Piperazine Compounds and the other therapeutic agent act synergistically to treat or prevent pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see *Paul A. Insel, Analgesic-Antipyretic and Anti-inflammatory Agents and Drugs Employed in the Treatment of Gout, in Goodman & Gilman's The Pharmacological Basis of Therapeutics* 617-57 (Perry B. Molinhoff and Raymond W. Ruddon eds., $9^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, dihydroergotamine, dolasetron, ergocornine, ergocorninine, ergocryptine, ergot, ergotamine, flumedroxone acetate, fonazine, lisuride, lomerizine, methysergide oxetorone, pizotyline, and mixtures thereof.

The other therapeutic agent can also be an agent useful for reducing any potential side effects of a Piperazine Compounds. For example, the other therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, piparnazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytyptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, pheneizine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alfa-2a, interferon alfa-2b, interferon alfa-n1, interferon alfa-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofirin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy, mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine;

verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; and methotrexate.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful anti-anxiety agents include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsaprione, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure include, but are not limited to, carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumerate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-$HT_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotilinr, nefazadone, nortriptyline, protriptyline, trazodone, trimipramine, and venlaflaxine; selective serotonin reuptake inhibitors such as fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A Piperazine Compound and the other therapeutic agent can act additively or, in one embodiment, synergistically. In one embodiment, a Piperazine Compound is administered concurrently with another therapeutic agent. In one embodiment, a composition comprising an effective amount of a Piperazine Compound and an effective amount of another therapeutic agent can be administered. Alternatively, a composition comprising an effective amount of a Piperazine Compound and a different composition comprising an effective amount of another therapeutic agent can be concurrently administered. In another embodiment, an effective amount of a Piperazine Compound is administered prior or subsequent to administration of an effective amount of another therapeutic agent.

4.3.2 Kits

The invention encompasses kits that can simplify the administration of a Piperazine Compound to an animal.

A typical kit of the invention comprises a unit dosage form of a Piperazine Compound. In one embodiment, the unit dosage form is a container, which can be sterile, containing an effective amount of a Piperazine Compound and a pharmaceutically acceptable carrier or excipient. The kit can further comprise a label or printed instructions instructing the use of the Piperazine Compound to treat pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression. The kit can also further comprise a unit dosage form of another therapeutic agent, for example, a container containing an effective amount of the other therapeutic agent. In one embodiment, the kit comprises a container containing an effective amount of a Piperazine Compound and an effective amount of another therapeutic agent. Examples of other therapeutic agents include, but are not limited to, those listed above.

Kits of the invention can further comprise a device that is useful for administering the unit dosage forms. Examples of such a device includes, but are not limited to, a syringe, a drip bag, a patch, an inhaler, and an enema bag.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

Examples 1-7 relate to the synthesis of illustrative Piperazine Compounds.

5.1 Example 1

Synthesis of Compounds 1c-1k

Scheme A

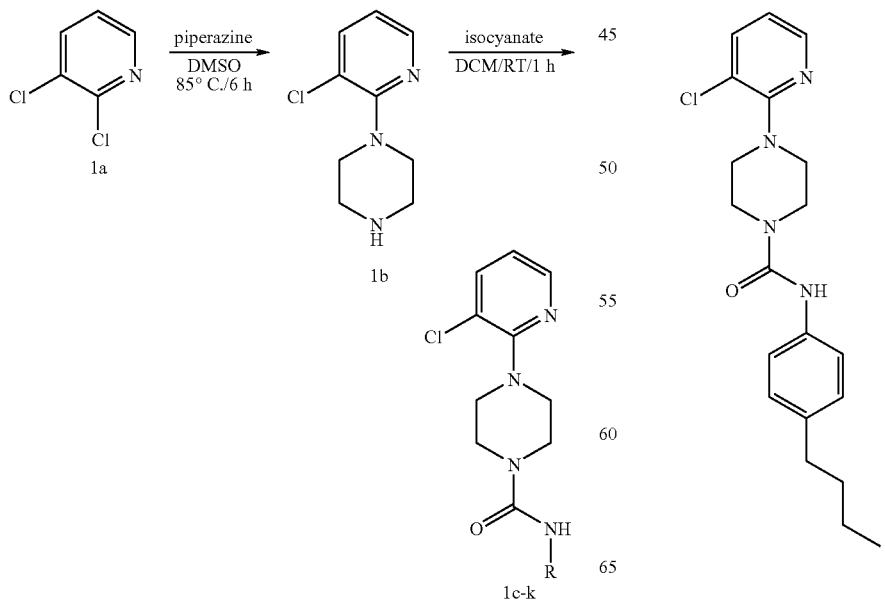

-continued

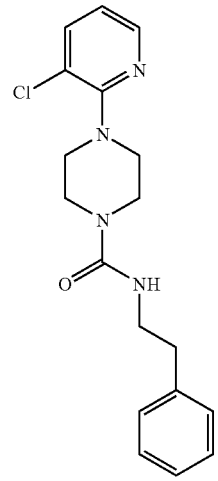

1c

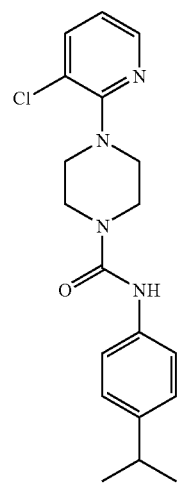

1d

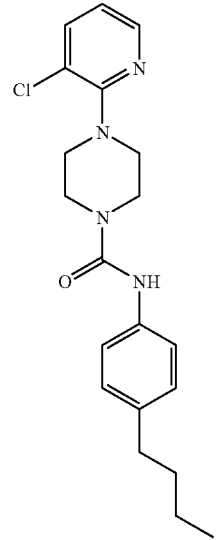

1e

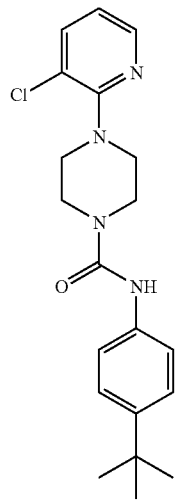 1f
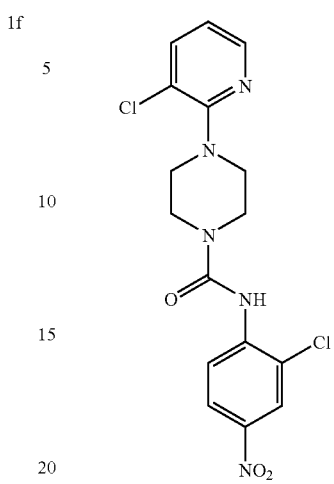 1i
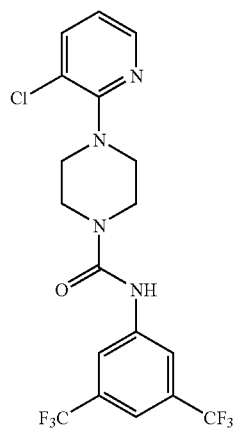 1g
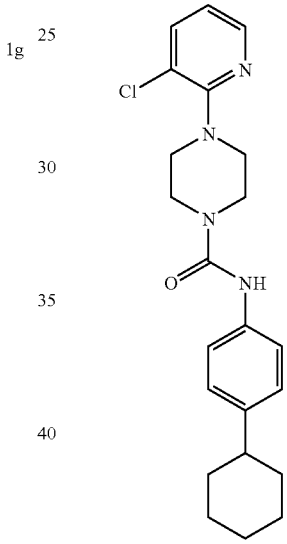 1j
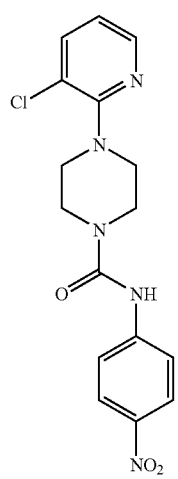 1h
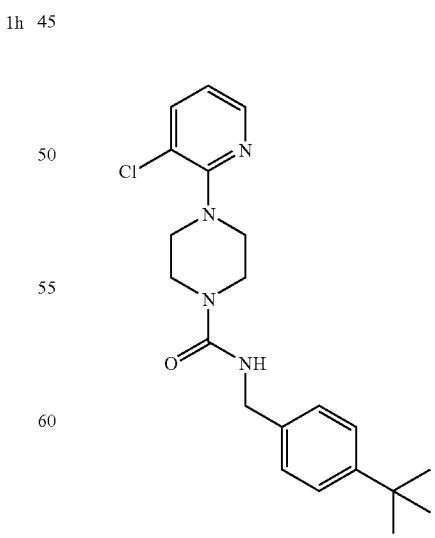 1k 2,3-Dichloropyridine 1a (0.22 g, 1.45 mmol) and 1.1 eq. of piperazine (0.14 g, 1.59 mmol) were dissolved in 3 mL of dimethyl sulfoxide (DMSO) and the resulting mixture was heated at 85° C. for 6 h. The reaction mixture was then cooled to room temperature and extracted with a saturated aqueous sodium bicarbonate solution. The organic layer was dried, concentrated, and purified using column chromatography to provide compound 1b as a yellow liquid.

Compounds 1c-k were made from compound 1b according to the following procedures:

1c: To compound 1b (440 mg, 2.22 mmol) dissolved in 3 ml of DMF was added 1.0 eq. (0.17 ml, 0.32 g, 2.22 mmol) of the phenethyl isocyanate. The resulting reaction mixture was placed on a shaker at room temperature. The reaction was monitored by liquid chromatography—mass spectrmetry) LC/MS. After 30 min, the reaction product was isolated and purified using column chromatography (ethyl acetate/hexane) to provide 0.11 g of compound 1c.

1d: To compound 1b (110.0 mg, 0.56 mmol) dissolved in 3 ml of methylene chloride was added 1.1 eq. (0.10 ml, 0.10 g, 0.61 mmol) of 4-i-propylphenyl isocyanate. The resulting reaction mixture was placed on a shaker at room temperature. The reaction was monitored by LC/MS. After 30 min, the reaction product was isolated and purified using column chromatography (ethyl acetate/hexane) to provide 0.19 g (92%) of compound 1d as white solid.

1e: To compound 1b (440 mg, 2.22 mmol) dissolved in 3 ml of DMF was added 1.0 eq. (0.11 ml, 0.39 g, 2.22 mmol) of 4-n-butylphenyl isocyanate. The resulting reaction mixture was placed on a shaker at room temperature. The reaction was monitored by LC/MS. After 30 min, the reaction product was isolated and purified using column chromatography (ethyl acetate/hexane) to provide 21.9 mg of compound 1e.

1f: To compound 1b (127.6 mg, 0.65 mmol) dissolved in 3 ml of methylene chloride was added 1.1 eq. (0.12 ml, 0.12 g, 0.72 mmol) of 4-t-butylphenyl isocyanate. The resulting reaction mixture was placed on a shaker at room temperature. The reaction was monitored by LC/MS. After 30 min, the reaction product was isolated and purified using column chromatography (ethyl acetate/hexane) to provide 0.23 g (93%) of compound 1f as white solid.

1g: To compound 1b (201 mg, 1.02 mmol) dissolved in 3 ml of methylene chloride was added 1.0 eq. (260 mg, 1.02 mmol) of 3,5-di-trifluoromethylphenyl isocyanate. The resulting reaction mixture was placed on a shaker at room temperature. The reaction was monitored by LC/MS. After 30 min, the reaction product was isolated and purified using column chromatography (ethyl acetate/hexane) to provide 236.4 mg of compound 1g.

1h: To compound 1b (201 mg, 1.02 mmol) dissolved in 3 ml of methylene chloride was added 1.0 eq. (167 mg, 1.02 mmol) of 4-nitrophenyl isocyanate. The resulting reaction mixture was placed on a shaker at room temperature. The reaction was monitored by LC/MS. After 30 min, the reaction product was isolated and purified using column chromatography (ethyl acetate/hexane) to provide 18.9 mg of compound 1h.

1i: To compound 1b (201 mg, 1.02 mmol) dissolved in 3 ml of methylene chloride was added 1.0 eq. (203 mg, 1.02 mmol) of 2-chloro-4-nitrophenyl isocyanate. The resulting reaction mixture was placed on a shaker at room temperature. The reaction was monitored by LC/MS. After 30 min, the reaction product was isolated and purified using column chromatography (ethyl acetate/hexane) to provide 155.7 mg of compound 1i.

1j: To compound 1b (112 mg, 0.57 mmol) dissolved in 3 ml of methylene chloride was added 1.5 eq. (170 mg, 0.85 mmol) of 4-cyclohexylphenylisocyanate. The resulting reaction mixture was placed on a shaker at room temperature. The reaction was monitored by LC/MS. After 30 min, the reaction product was isolated and purified using column chromatography (EtOAc/Hexane) to provide 202.2 mg of compound 1j.

1k: 2,3-dichloropyridine 1a (22 mg, 0.14 mmol) dissolved in 2 ml of DMSO was added 1.1 eq. (14 mg, 0.16 mmol) of piperazine. The resulting reaction mixture was placed on a shaker at 85° C. for 4 h, cooled to room temperature, 1.5 eq. (40 mg, 0.21 mmol) of 4-tert-butylbenzyl isocyanate added, and the mixture placed on a shaker at room temperature for 1 h. The crude product was isolated and purified using column chromatography by column chromatography (EtOAc/Hexane) to provide 8.5 mg of compound 1k.

The identity of compounds 1c-1k was confirmed by $^1$H NMR.

1c: $^1$H NMR (400 MHZ, CDCl$_3$): δ 8.18 (dd, 1 H, J=4.7, 1.6), 7.60 (dd, 1 H, J=7.8, 1.6), 7.36-7.18 (m, 5 H), 6.87 (dd, 1 H, J=7.8, 4.7), 4.48 (bs, 1 H), 3.55-3.50 (m, 2 H), 3.48-3.45 (m, 4 H), 3.34-3.33 (m, 4 H), 2.85 (t, 2 H, J=7.1).

1d: $^1$H NMR (400 MHZ, CDCl$_3$): δ 8.20 (bd, 1 H, J=4.6), 7.62 (d, 1 H, J=7.7), 7.29 (d, 2 H J=8.4), 7.15 (d, 2 H J=8.4), 6.87 (dd, 1 H J=7.7, 4.8), 6.58 (bs, 1 H), 3.67-3.64 (m, 4 H), 3.41-3.39 (m, 4 H), 2.91-2.84 (m, 1 H), 1.23 (d, 6 H, J=6.9).

1e: $^1$H NMR (400 MHZ, CDCl$_3$): δ 8.19 (dd, 1 H, J=4.7, 1.5), 7.61 (dd, 1 H, J=7.7, 1.5), 7.25 (d, 2 H, J=8.4), 7.10 (d, 2 H, J=8.4), 6.89 (dd, 1 H, J=7.7, 4.7), 6.34 (s, 1 H), 3.67-3.64 (m, 2 H), 3.42-3.40 (m, 4 H), 2.58 (t, 2 H, J=7.6), 1.56 (m, 2 H), 1.32 (m, 2 H), 0.91 (t, 3 H, J=7.3).

1f: $^1$H NMR (400 MHZ, CDCl$_3$): δ 8.25 (dd, 1 H, J=4.8, 1.6), 7.67 (dd, 1 H, J=7.7, 1.6), 7.39-7.32 (m, 4 H), 6.95 (dd, 1 H, J=7.7, 4.7), 6.41 (bs, 1 H), 3.73-3.70 (m, 4 H), 3.49-3.46 (m, 4 H), 1.36 (s, 9 H).

1g: $^1$H NMR (400 MHZ, CDCl$_3$): δ 8.26 (dd, 1 H, J=4.7, 1.6), 7.97 (s, 2 H), 7.70 (dd, 1 H, J=7.8, J=1.6), 7.59 (s, 1 H), 6.97 (dd, 1H, J=7.8, 4.8), 6.76 (s, 1 H), 3.77-3.74 (m, 4 H), 3.51-3.48 (m, 4 H).

1h: $^1$H NMR (400 MHZ, CDCl$_3$): δ 8.27-8.24 (m, 3 H), 7.70 (dd, 1 H, J=7.8, J=1.6), 7.62 (dd, 2 H, J=7.2, 2.0), 6.97 (dd, 1 H, J=7.8, 4.7), 6.80 (bs, 1 H), 3.78-3.75 (m, 4 H), 3.52-3.49 (m, 4 H).

1i: $^1$H NMR (400 MHZ, CDCl$_3$): δ 8.58 (d, 1 H, J=9.3), 8.36 (d, 1 H, J=2.5), 8.27 (dd, 1 H, J=4.8, 1.7), 7.70 (dd, 1 H, J=7.8, 1.6), 7.48 (bs, 1 H), 6.98 (dd, 1 H, J=7.8, 4.8), 3.82-3.79 (m, 4 H), 3.54-3.52 (m, 4 H).

1j: $^1$H NMR (400 MHZ, CDCl$_3$): δ 8.26 (dd, 1 H, J=4.7, 1.6), 7.68 (dd, 1 H, J=7.8, 1.6), 7.34 (bd, 2 H J=8.4), 7.21 (bd, 2 H J=8.4), 6.94 (dd, 1 H, J=7.7, 4.7), 6.37 (bs, 1 H), 3.73-3.70 (m, 4 H), 3.49-3.47 (m, 4 H), 2.51 (m, 1 H), 1.89 (m, 4 H), 1.8 (m, 1 H), 1.48-1.41 (m, 4 H).

1k: $^1$H NMR (400 MHZ, CDCl$_3$): δ 8.24 (dd, 1 H, J=4.8, 1.7), 7.66 (dd, 1 H, J=7.8, 1.7), 7.45-7.34 (m, 4 H), 6.93 (dd, 1 H, J=7.8, 4.8), 4.78 (t, 1 H, J=5.0), 4.48 (d, 2 H, J=5.3), 3.62-3.59 (m, 4 H), 3.43-3.40 (m, 4 H), 1.37 (s, 9 H).

5.2 Example 2

Synthesis of Compounds 2a and 2b

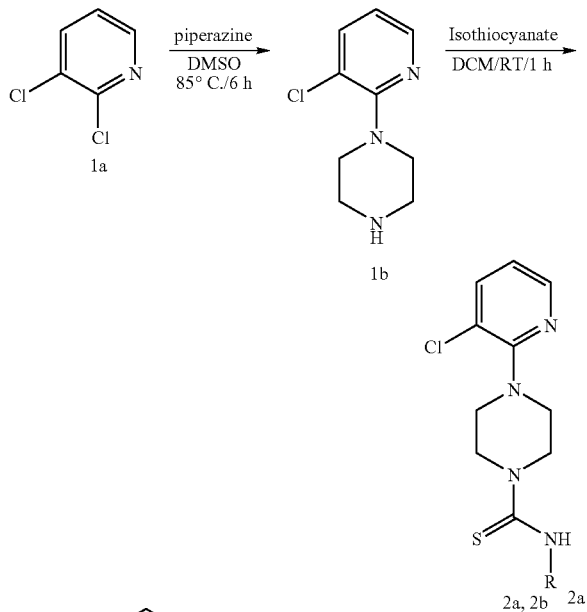

Compounds 2a and 2b were prepared from compound 1b (prepared as in Example 1) according to the following procedures:

2a: Compound 1b (440 mg, 2.22 mmol) was dissolved in 3 mL of dimethylformamide, 1 eq. (0.42 g, 2.22 mmol) of 4-tert-butylphenyl isothiocyanate was added to the solution, and the resulting reaction mixture placed on a shaker at room temperature. The reaction was monitored using LC/MS. After 30 min. the reaction product was isolated and purified using column chromatography (ethyl acetate/hexane) to provide 75.6 mg of 2a as a white solid.

2b: Compound 1b (440 mg, 2.22 mmol) was dissolved in 3 mL of dimethylformamide, 1 eq. (0.39 g, 2.22 mmol) of 4-isopropylphenylisothiocyanate was added to the solution, and the resulting reaction mixture placed on a shaker at room temperature. The reaction was monitored using LC/MS. After 30 min. the reaction product was isolated and purified using column chromatography (ethyl acetate/hexane) to provide 28.6 mg of 2a as a white solid.

The identity of compounds 2a and 2b was confirmed by $^1$H NMR.

2a: $^1$H NMR (400 MHZ, CDCl$_3$): δ 8.18 (dd, 1 H, J=4.7, 1.6), 7.60 (dd, 1 H, J=7.8, 1.6), 7.35 (d, 2 H, J=8.5), 7.20 (s, 1 H), 7.10 (d, 2 H, J=8.5), 6.88 (dd, 1 H, J=7.8, 4.7), 4.00-3.98 (m, 4 H), 3.47-3.44 (m, 4 H), 1.31 (s, 9 H).

2b: $^1$H NMR (400 MHZ, CDCl$_3$): δ 8.18 (dd, 1 H, J=4.7, 1.6), 7.60 (dd, 1 H, J=7.8, 1.6), 7.20 (d, 2 H, J=8.4), 7.08 (d, 2 H, J=8.4), 6.88 (dd, 1 H, J=7.8, 4.7), 4.00-3.98 (m, 4 H), 3.47-3.44 (m, 4 H), 2.93-2.86 (m, 1 H), 1.24 (d, 6 H, J=6.9).

5.3 Example 3

Synthesis of Compounds 3a-3b

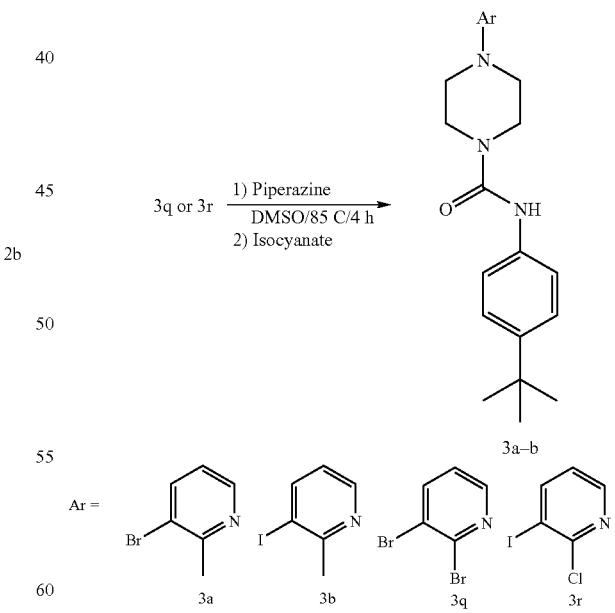

Compounds 3a and 3b were prepared by the following procedures:

3a: To compound 3q (0.25 g, 1.07 mmol) dissolved in 3 ml of DMSO was added 1.1 eq. (0.1 g, 1.17 mmol) of piperazine and the resulting reaction mixture placed on a shaker at 85° C. for 4 h. After 4 h, the reaction mixture was cooled to room temperature, 1.1 eq. (0.21 g, 1.17 mmol) of 4-t-butyl-phenyl isocyanate added, and the mixture placed on a shaker at room temperature for 1 h. The reaction product was then isolated and purified using column chromatography (ethyl acetate/hexane) to provide 91.2 mg of 3a as a white solid.

3b: To compound 3r (24 mg, 0.097 mmol) dissolved in 3 ml of DMSO was added 1.2 eq. (11 mg, 0.12 mmol) of piperazine and the resulting reaction mixture placed on a shaker at 85° C. for 4 h. After 4 h, the reaction mixture was cooled to room temperature, 1.0 eq. (17 mg, 0.097 mmol) of 4-t-butyl-phenyl isocyanate added, and the mixture placed on a shaker at room temperature for 1 h. The reaction product was then isolated and purified using column chromatography (ethyl acetate/hexane) to provide 20.3 mg of compound 3b.

The identity of compounds 3a and 3b was confirmed by $^1$H NMR.

3a: $^1$H NMR (400 MHZ, CDCl$_3$): δ 8.27 (dd, 1 H, J=4.7, 1.6), 7.84 (dd, 1 H, J=7.8, 1.6), 7.35-7.29 (m, 4 H), 6.85 (dd, 1 H, J=7.8, 4.7), 6.35 (bs, 1 H), 3.70-3.67 (m, 4 H), 3.42-3.40 (m, 4 H), 1.32 (s, 9 H).

3b: $^1$H NMR (400 MHZ, CDCl$_3$): δ 8.34 (dd, 1 H, J=4.7, 1.7), 8.15 (dd, 1 H, J=7.7, 1.7), 7.39-7.33 (m, 4 H), 6.76 (dd, 1 H, J=7.7, 4.7), 6.40 (s, 1 H), 3.75-3.72 (m, 4 H), 3.40-3.37 (m, 4 H), 1.36 (s, 9 H).

5.4 Example 4

Synthesis of Compounds 4a-4b

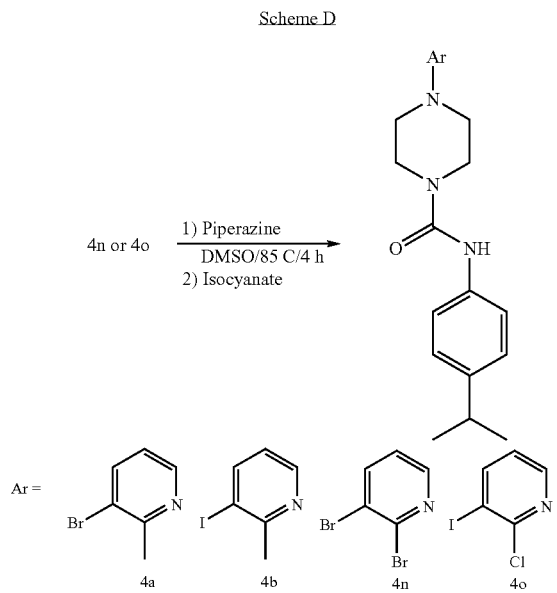

Compounds 4a and 4b were prepared by the following procedures:

4a: To compound 4n (0.24 g, 1.01 mmol) dissolved in 3 ml of DMSO was added 1.1 eq. (0.096 g, 1.11 mmol) of piperazine and the resulting reaction mixture placed on a shaker at 85° C. for 4 h. After 4 h, the reaction mixture was cooled to room temperature, 1.1 eq. (0.18 ml, 0.18 g, 1.11 mmol) of 4-i-propyl-phenyl isocyanate added, and the mixture placed on a shaker at room temperature for 1 h. The reaction product was then isolated and purified using column chromatography (ethyl acetate/hexane) to provide 56.2 mg of compound 4a as a white solid.

4b: To compound 4o (24 mg, 0.097 mmol) dissolved in 3 ml of DMSO was added 1.2 eq. (11 mg, 0.12 mmol) of piperazine and the resulting reaction mixture placed on a shaker at 85° C. for 4 h. After 4 h, the reaction mixture was cooled to room temperature, 1.0 eq. (16 mg, 0.097 mmol) of 4-i-propyl-phenyl isocyanate added, and the mixture placed on a shaker at room temperature for 1 h. The reaction product was then isolated and purified using column chromatography (ethyl acetate/hexane) to provide 19.6 mg of compound 3b.

The identity of compounds 4a and 4b was confirmed by $^1$H NMR.

4a: $^1$H NMR (400 MHZ, CDCl$_3$): δ 8.34 (dd, 1 H, J=4.7, 1.6), 8.15 (dd, 1 H, J=7.7, 1.6), 7.34 (d, 2 H J=8.5), 7.21 (d, 2 H J=8.5), 6.76 (dd, 1 H J=7.7, 4.7), 6.41 (s, 1 H), 3.75-3.72 (m, 4 H), 3.39-3.36 (m, 4 H), 2.94-2.91 (m, 1 H), 1.28 (d, 6 H, J=6.9).

4b: $^1$H NMR (400 MHZ, CDCl$_3$): δ 8.31 (d, 1 H, J=4.8), 7.27 (bd, 2 H, J-=8.5), 7.13 (d, 2 H. J=8.5), 6.51 (t, 1 H, J=4.7), 3.86-3.83 (m, 4 H), 3.56-3.53 (m, 4 H), 2.85-2.82 (m, 1 H), 1.20 (d, 6 H, J=6.9).

5.5 Example 5

Synthesis of Compound 5a

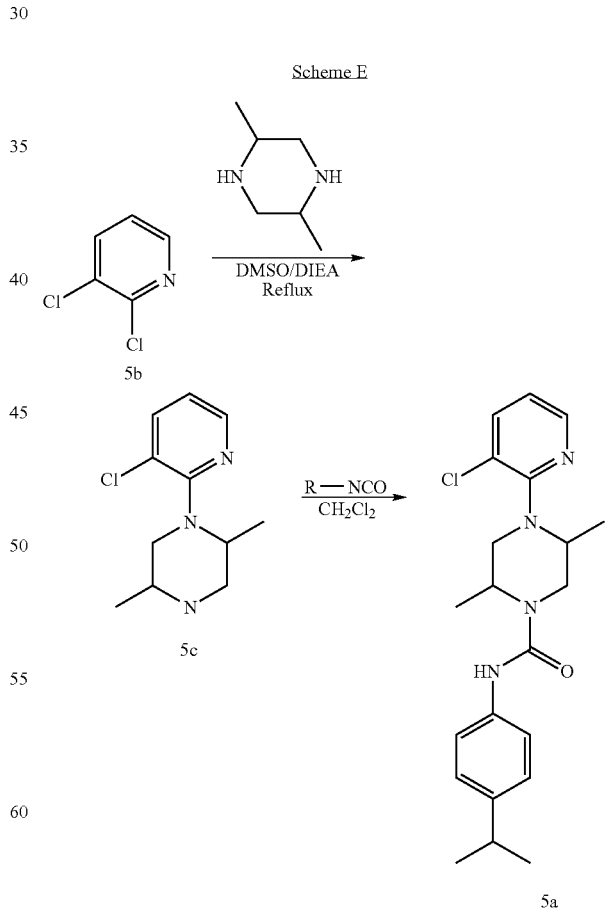

To 50 mL of a DMSO solution of compound 5b (1 g) was added 2,5-dimethylpiperazine (3 eq) followed by the addition of di-isopropylethyl amine (DIEA) (0.87 g). The reaction mixture was stirred at 120° C. for 15 hours. Water and ethyl acetate were added to the reaction mixture, and the organic and aqueous phases were separated. The aqueous phase was extracted twice with ethyl acetate. The organic extracts were combined, washed with water, washed with brine, dried with sodium sulfate, and concentrated to provide compound 5c (0.44 g). Compound 5c (0.44 g) was reacted with 4-i-propyl-phenyl isocyanate (1.2 eq) in DCM (2 mL) to provide compound 5a (0.028 g). Compound 5a was purified using silica-gel chromatography (30:70 ethyl acetate:hexane). The identity of compound 5a was confirmed using $^1$H NMR.

5a: $^1$H NMR (400 MHZ, CD$_3$OD): δ 1.24 (d, 3H), 1.29 (d, 6H), 2.23 (d, 3H), 2.85 (m, 1H), 3.40 (d, 1H), 3.71 (q, 3H), 4.45 (bs, 2H), 6.45 (s, 1H), 6.75 (m, 1H), 7.12 (m, 2H), 7.25 (m, 2H), 7.51 (dd, 1H), 8.12 (m, 1H).

5.6 Example 6

Synthesis of Compounds 6a-6e

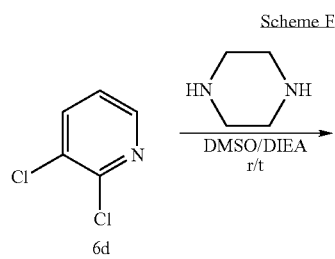

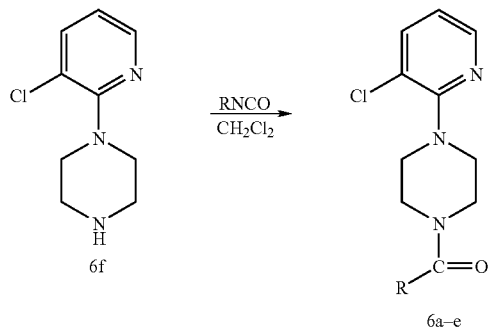

To compound 6d (2 g) in 25 mL of dimethylsulfoxide (DMSO) was added piperazine (3.46 g) followed by the addition of DIEA (1.76 g). The reaction mixture was stirred at 120° C. for 15 hours. Water and ethyl acetate were added to the reaction mixture, and the organic and aqueous phases were separated. The aqueous phase was extracted twice with ethyl acetate. The organic extracts were combined, washed with water, washed with brine, dried with sodium sulfate, and concentrated to provide compound 6f (1.3 g). Compound 6f (0.2 g) was reacted with the appropriate isocyanate, RNCO, (0.047 g of 4-bromophenyl isocyante for compound 6a, 0.53 g of 4-iodoophenyl isocyante for compound 6b, 0.43 g of 4-acetylphenyl isocyante for compound 6c, 0.50 g of 4-benzyloxypheny lisocyante for compound 6d, and 0.16 g of 4-n-propylphenyl isocyante for compound 6e) in 5 mL of DCM to provide compounds 6a-e. The identity of compounds 6a-e was confirmed using $^1$H NMR.

6a: $^1$H NMR (400 MHZ, DMSO): δ 3.25 (bs, 4H), 3.75 (bs, 4H), 7.01 (m, 1H), 7.45 (d, 2H), 7.52 (d, 2H), 7.92 (dd, 1H), 8.22 (dd, 1H), 8.82 (s, 1H).

6b: $^1$H NMR (400 MHZ, DMSO): δ 3.25 (bs, 4H), 3.75 (bs, 4H), 7.01 (m, 1H), 7.45 (d, 2H), 7.52 (d, 2H), 7.92 (dd, 1H), 8.22 (dd, 1H), 8.82 (s, 1H).

6c: $^1$H NMR (400 MHZ, DMSO): δ 2.25 (s, 3H), 3.35 (bs, 4H), 3.75 (bs, 4H), 7.01 (m, 1H), 7.55 (d, 2H), 7.82 (d, 2H), 8.27 (dd, 1H), 9.05 (dd, 1H), 9.47 (s, 1H).

6d: $^1$H NMR (400 MHZ, DMSO): 3.35 (bs, 4H), 3.75 (bs, 4H), 5.01 (s, 2H), 6.90 (m, 2H), 7.02 (m, 1H), 7.45-7.55 (bm, 7H), 7.77 (dd, 1H), 8.25 (dd, 1H), 8.40 (s, 1H).

6e: $^1$H NMR (400 MHZ, DMSO): 0.91 (m, 3H), 1.52 (m, 2H), 2.50 (q, 2H), 3.25 (t, 4H), 3.62 (t, 4H), 6.45 (s, 1H), 6.82 (dd, 1H), 7.15 (t, 2H), 7.25 (t, 2H), 7.78 (dd, 1H), 8.25 dd, 1H).

5.7 Example 7

Synthesis of Compounds 7a-7i

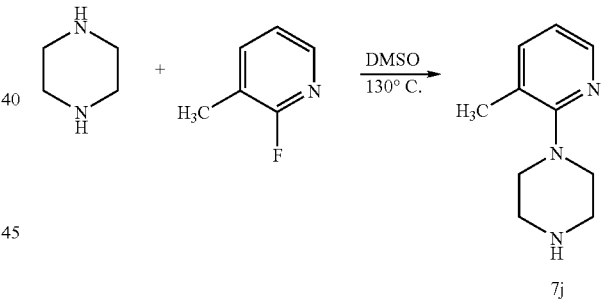

To 5 g (43.65 mmol) of 2-fluoro-3-methylpyridine in 20 mL of DMSO was added 20 g (~5.3 eq.) of piperazine, and the resulting mixture was heated to reflux (~130° C.) overnight under a drying tube. The reaction mixture was cooled, diluted with 50 mL of H$_2$O, and extracted with ethyl acetate (3×40 mL). The organic phase was washed with H$_2$O, aqueous saturated NaCl, and dried over MgSO$_4$. The organic solvent was then removed under reduced pressure, and the resulting residue was dissolved in minimum amount of CH$_2$Cl$_2$ and purified using silica-gel chromatography (elution: varied ratios of ethyl acetate/hexane to ethyl acetate/ MeOH) to provide 2.2 g (yield: 28.4%) of 7j as a pale yellow oil. The identity of compounds 7j was confirmed by $^1$H NMR. chromatography.

7j: $^1$H NMR (400 MHz, CDCl$_3$) δ 1.70 (broad s, 1), 2.29 (s, 3), 3.03 (t, 4), 3.11 (t, 4), 6.85 (dd, 1), 7.40 (d, 1), 8.18 (d, 1).

Other Piperazine Compounds can be prepared using other appropriately substituted 2-fluoropyridines according to Scheme H:

Scheme H

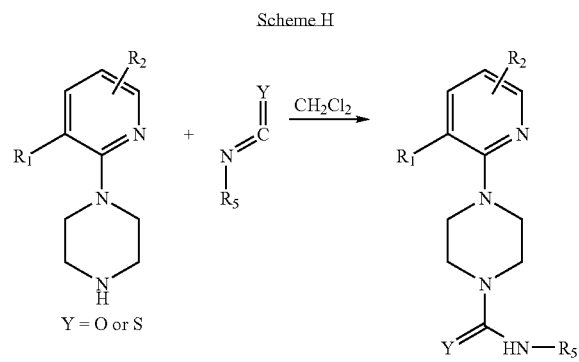

Y = O or S

To a solution of 0.239 g (1.3472 mmol) of 3-methyl-2-piperazinylpyridine (7j) in 10 mL of $CH_2Cl_2$ was added 0.236 g (1 eq.) of 4-tert-butylphenyl isocyanate. The mixture was stirred under $N_2$ overnight. The solvent was then removed under reduced pressure and the resulting residue was recrystallized from ethyl acetate-hexane to provide 0.34 g (yield: 71.6%) of 7a as white crystals (see Scheme I wherein $R_1$=3-$CH_3$, $R_2$=H, Y=O, and $R_5$=4-tert-butylphenyl).

Compounds 7b-f were made using a procedure analogous to that used to make compound 7a, but using the appropriate isocyanate. The structure of compounds 7a-f is provided in Table I below.

TABLE I

Compounds 7a–f.

| $R_1$ | $R_2$ | $R_5$ | Y | Product |
|---|---|---|---|---|
| 3-Me | H | 4-tert-butylphenyl | O | 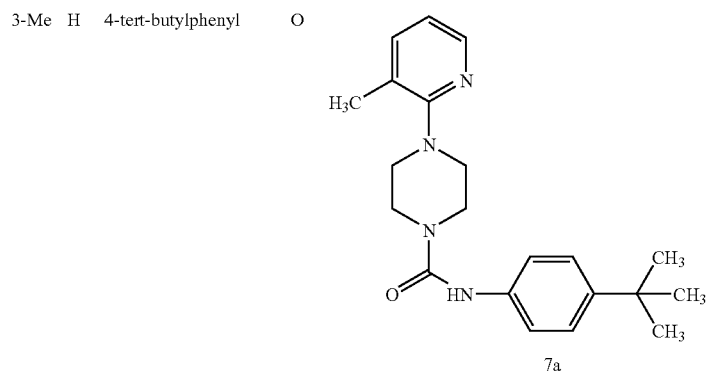<br>7a |
| 3-Me | H | 4-isopropylphenyl | O | 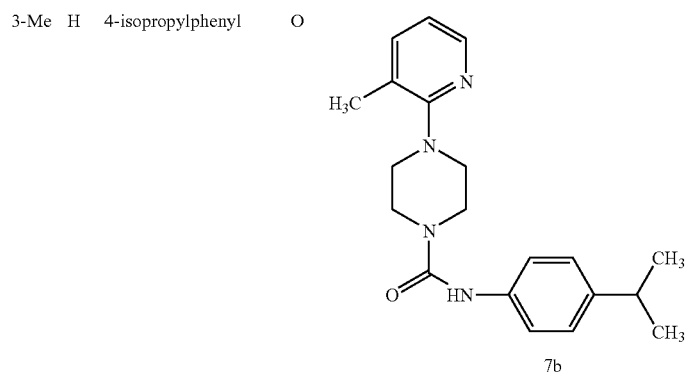<br>7b |

TABLE I-continued
Compounds 7a–f.
| R₁ | R₂ | R₅ | Y | Product |
|---|---|---|---|---|
| 3-Me | H | 4-butylphenyl | O | 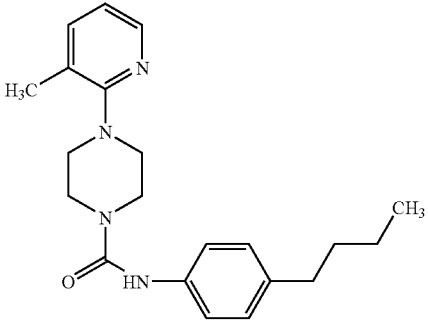 7c |
| 3-Cl | H | 4-tert-butylcyclohexyl | O | 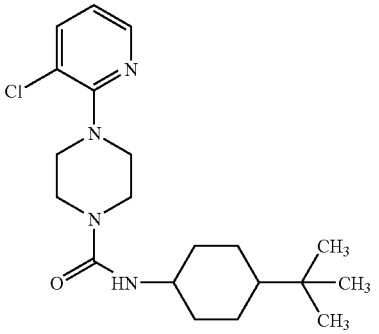 7d |
| 3-Cl | H | cyclooctyl | S | 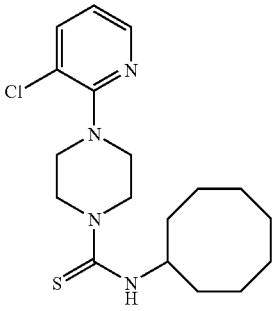 7e |
| 3-Cl | H | (4-ethyl carboxylate)phenyl | O | 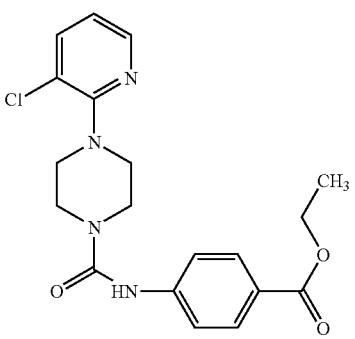 7f |

The identity of compounds 7a-f was confirmed by $^1$H NMR.

7a: $^1$H NMR (400 MHz, CDCl3) δ 1.26 (s, 9), 2.30 (s, 3), 3.20 (t, 4), 3.64 (t, 4), 6.41 (broad s, 1), 6.89 (t, 1), 7.30 (m, 4), 7.42 (d, 1), 8.16 (d, 1).

7b: $^1$H NMR (400 MHz, CDCl3) δ 1.21 (d, 6), 2.29 (s, 3), 2.83 (m, 1), 3.17 (t, 4), 3.62 (t, 4), 6.62 (broad s, 1), 6.88 (dd, 1), 7.14 (d, 2), 7.27 (d, 2), 7.42 (dd, 1), 8.12 (dd, 1).

7c: $^1$H NMR (400 MHz, CDCl3) δ 0.90 (t, 3), 1.31 (m, 2), 1.53 (m, 2), 2.28 (s, 3), 2.53 (t, 3), 3.15 (t, 4), 3.60 (t, 4), 6.76 (s, 1), 6.88 (dd, 1), 7.07 (d, 2), 7.27 (d, 2), 7.42 (d, 1), 8.15 (d, 1).

7d: $^1$H NMR (400 MHz, CDCl3) δ 0.85 (s, 9), 0.96 (m, 1), 1.12 (m, 4), 1.79 (t, 2), 2.06 (t, 2), 3.28 (t, 4), 3.50 (t, 4), 3.60 (m, 1), 4.34 (d, 1), 7.02 (dd, 1), 7.87 (d, 1), 8.43 (d, 1).

7e: $^1$H NMR (400 MHz, CDCl3) δ 1.70 (m, 12), 2.06 (m, 2), 3.54 (t, 4), 4.04 (t, 4), 4.73 (m, 1), 5.65 (d, 1), 6.97 (dd, 1), 7.71 (d, 1), 8.26 (d, 1).

7f: $^1$H NMR (400 MHz, CDCl3) δ 1.38 (t, 3), 3.41 (t, 4), 3.68 (t, 4), 4.32 (quartet, 2), 6.89 (m, 1), 6.96 (broad s, 1), 7.48 (dd, 2), 7.63 (d, 1), 7.97 (d, 2), 8.19 (d, 1).

5.8 Example 8

Binding of the Piperazine Compounds to the Human VR1 Receptor

VR1 antagonism has been associated with the prevention of pain (See, e.g., R. Wrigglesworth and C. Walpole, "*Capsaicin-like Agonists*," Drugs of the Future, 23(5), pp. 531-538 (1998); S. Bevan P. McIntyre, "*Vanilloid Receptors: Pivotal Molecules in Nocciception*," Current Opinions in CPNS Investigational Drugs, vol. 2, no. 2, pp. 178-185 (2000) and A. Szallash and P. Blumberg, "*Vanilloid (Capsaicin) Receptors and Mechanisma*," Pharmacology Reviews, vol. 51, no. 2, pp. 159-211 (1999)).

Methods for assaying compounds capable of inhibiting VR1 are well known to those skilled in the art, for example, those methods disclosed in U.S. Pat. No. 6,239,267 to Duckworth et al.; U.S. Pat. No. 6,406,908 to McIntyre et al.; or U.S. Pat. No. 6,335,180 to Julius et al.

Typically, the Piperazine Compounds have an IC$_{50}$ value for inhibition of capsaicin-induced activation that is less than 25 μM, preferably less than 1,000 nM, and more preferably less than 500 nM, or an IC$_{50}$ value for inhibition of pH-induced inactivation that is less than 10 μM, preferably less than 1,000 nM, and more preferably less than 500 nM.

The following Piperazine Compound inhibits capsaicin-induced activation and pH-induced activation of VR1 as shown below:

| Compound | Inhibition of Capsaicin-Induced Activation IC$_{50}$ (nM) Mean IC$_{50}$ ± SEM$^a$ (n)$^b$ | Inhibition of pH-Induced Activation IC$_{50}$ (nM) Mean IC$_{50}$ ± SEM$^a$ (n)$^b$ |
|---|---|---|
|  | 1.3 ± 1.2 (3) | 5.4 ± 2.5 (3) |

$^a$SEM = standard deviation
$^b$n = number of experiments

5.9. Example 9

Binding of Piperazine Compounds to mGluR5

The following astrocyte assay can be used to demonstrate that Piperazine Compounds bind to and modulate the activity of mGluR5.

Cell cultures: Primary glial cultures are prepared from cortices of Sprague-Dawley 18 days old embryos. The cortices are dissected and then dissociated by trituration. The resulting cell homogenate is plated onto poly-D-lysine precoated T175 flasks (BIOCOAT, commercially available from Becton Dickinson and Company Inc. of Franklin Lakes, N.J.) in Dulbelcco's Modified Eagle's Medium ("DMEM," pH 7.4), buffered with 25 mM HEPES, and supplemented with 15% fetal calf serum ("FCS," commercially available from Hyclone Laboratories Inc. of Omaha, Nebr.), and incubated at 37° C. and 5% CO$_2$. After 24 hours, FCS supplementation is reduced to 10%. On day six, oligodendrocytes and microglia are removed by strongly tapping the sides of the flasks. One day following this purification step, secondary astrocyte cultures are established by subplating onto 96 poly-D-lysine precoated T175 flasks BIOCOAT) at a density of 65,000 cells/well in DMEM and 10% FCS. After 24 hours, the strocytes are washed with serum free medium and then cultured in DMEM, without glutamate, supplemented with 0.5% FCS, 20 mM HEPES, 10 ng/mL epidermal growth factor ("EGF"), 1 mM sodium pyruvate, and 1× penicillin/streptomycin at pH 7.5 for 3 to 5 days at 37° C. and 5% CO$_2$. The procedure allows the expression of the mGluR5 receptor by astrocytes, as demonstrated by S. Miller et al., *J. Neuroscience* 15(9):6103-6109 (1995).

Assay Protocol: After 3-5 days incubation with EGF, the astrocytes are washed with 127 mM NaCl, 5 mM KCl, 2 mM MgCl$_2$, 700 mM NaH$_2$PO$_4$, 2 mM CaCl$_2$, 5 mM NaHCO$_3$, 8 mM HEPES, 10 mM Glucose at pH 7.4 ("Assay Buffer")

and loaded with the dye Fluo-4 (commercially available from Molecular Probes Inc. of Eugene, Oreg.) using 0.1 mL of Assay Buffer containing Fluo-4 (3 mM final). After 90 minutes of dye loading, the cells are then washed twice with 0.2 mL Assay Buffer and resuspended in 0.1 mL of Assay Buffer. The plates containing the astrocytes are then transferred to a Fluorometric Imaging Plate reader (commercially available from Molecular Devices Corporation of Sunnyvale, Calif.) for the assessment of calcium mobilization flux in the presence of glutamate and in the presence or absence of antagonist. After monitoring fluorescence for 15 seconds to establish a base line, DMSO solutions containing various concentrations of a Piperazine Compound diluted in Assay Buffer (0.05 mL of 4× dilutions for competition curves) are added to the cell plate and fluorescence is monitored for 2 minutes. 0.05 mL of a 4× glutamate solution (agonist) is then added to each well to provide a final glutamate concentration in each well of 10 mM. Plate fluorescence is then monitored for an additional 60 seconds after agonist addition. The final DMSO concentration in the assay is 1.0%. In each experiment, fluorescence is monitored as a function of time and the data analyzed using Microsoft Excel and GraphPad Prism. Dose-response curves are fit using a non-linear regression to determine $IC_{50}$ value. In each experiment, each data point is determined two times. The results demonstrate Piperazine Compounds that bind to and modulate the activity of mGluR5.

The following CHO assay can be used to demonstrate that Piperazine Compounds bind to and modulate the activity of mGluR5.

40,000 CHO-rat mGluR5 cells/well were plated into 96 well plate (Costar 3409, Black, clear bottom, 96 well, tissue culture treated) for an overnight incubation in Dulbelcco's Modified Eagle's Medium (DMEM, pH 7.4) and supplemented with glutamine, 10% FBS, 1% Pen/Strep, and 500 ug/ml Geneticin. CHO-rat mGluR5 cells were washed and treated with Optimem medium and incubated for 1-4 hours prior to loading cells. Cell plates were then washed with loading buffer (127 mM NaCl, 5 mM KCl, 2 mM $MgC_2$, 700 μM Na $H_2PO_4$, 2 mM $CaCl_2$, 5 mM Na $HCO_3$, 8 mM Hepes, and 10 mM Glucose, pH 7.4) and then incubated with 3 μM Fluo 4 (commercially available from Molecular probes Inc. of Eugene, Oreg.) in 0.1 mL of loading buffer. After 90 minutes of dye loading, the cells were then washed twice with 0.2 mL loading buffer and resuspended in 0.1 mL loading buffer. The plates containing the CHO-rat mGluR5 cells were then transferred to Fluorometric Imaging Plate Reader (FLIPR) (commercially available from Molecular Devices Corporation of Sunnyvale, Calif.) for the assessment of calcium mobilization flux in the presence of glutamate and in the presence or absence of test compounds. After monitoring fluorescence for 15 seconds to establish a base line, DMSO solutions containing various concentrations of the test compound diluted in loading buffer (0.05 nL of 4× dilutions for the competition curves) were added to the cell plate and fluorescence was monitored for 2 minutes. 0.05 mL of 4× glutamate solution (agonist) was then added to each well to provide a final glutamate concentration in each well of 10 uM. Plate fluorescence is then monitored for an additional 60 seconds after agonist addition. The final DMSO concentration in the assay was 1.0%. In each experiment, fluorescence is monitored as a function of time and the data analyzed using Microsoft Excel and GraphPad Prism. Dose-response curves were fit using a non-linear regression to determine IC50 value. In each experiment each data point was determined two times.

Using the above CHO assay, the following compound inhibits mGluR5 at a concentration of 10 μM:

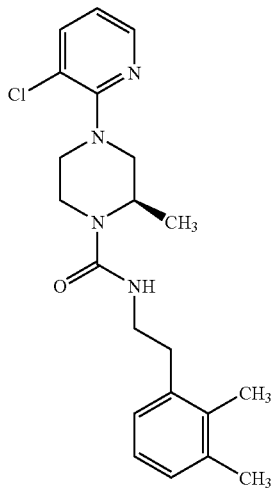

5.10. Example 10

In Vivo Assays for Prevention or Treatment of Pain

Test Animals: Each experiment uses rats weighing between 200-260 g at the start of the experiment. The rats are group-housed and have free access to food and water at all times, except prior to oral administration of a Piperazine Compound when food is removed for 16 hours before dosing. A control group acts as a comparison to rats treated with a Piperazine Compound. The control group is administered the carrier for the Piperazine Compound. The volume of carrier administered to the control group is the same as the volume of carrier and Piperazine Compound administered to the test group.

Acute Pain: To assess the actions of the Piperazine Compounds for the treatment or prevention of acute pain the rat tail flick test can be used. Rats are placed inside a cotton pouch and the tail exposed to a focused beam of radiant heat at a point 3 cm from the tip using a tail flick unit (Model 7360, commercially available from Ugo Basile of Italy). Tail flick latencies are defined as the interval between the onset of the thermal stimulus and the flick of the tail. Animals not responding within 15 seconds are removed from the tail flick unit and assigned a withdrawal latency of 15 seconds. Tail flick latencies are measured immediately before (pre-treatment) and 1, 3, and 6 hours following administration of a Piperazine Compound. Data are expressed as tail flick latency(s) and the percentage of the maximal possible effect (% MPE), i.e., 15 seconds, is calculated as follows:

$$\% \, MPE = \frac{[(\text{post administration latency}) - (\text{pre-administration latency})]}{(15 \, s \, \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941). The results demonstrate Piperazine Compounds that are useful for treating or preventing acute pain.

Acute pain can also be assessed by measuring the animal's response to noxious mechanical stimuli by determining the paw withdrawal threshold (PWT), as described below.

Inflammatory Pain: To assess the actions of the Piperazine Compounds for the treatment or prevention of inflammatory pain the Freund's complete adjuvant (FCA) model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacology* 342:666-670 (1990)). The left hind paw of each animal is administered a 50 μL intraplantar injection of 100% FCA. 24 hour post injection, the animal is assessed for response to noxious mechanical stimuli by determining the PWT, as described below. Rats are then administered a single injection of 1, 3, 10 or 30 mg/Kg of either a Piperazine Compound, 30 mg/Kg indomethacin or carrier. Responses to noxious mechanical stimuli are then determined 2, 4, 6, and 24 hours post administration. Percentage reversal of hyperalgesia for each animal is defined as:

$$\% \text{ Reversal} = \frac{[(\text{post administration } PWT) - (\text{pre-administration } PWT)]}{(\text{Baseline pre-administration } PWT)} \times 100$$

The results demonstrate Piperazine Compounds that are useful for treating or preventing inflammatory pain.

Neuropathic Pain: To assess the actions of the Piperazine Compounds for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under enflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the conunon sciatic nerve. A 7-0 silk suture is inserted into the nerve with a 3/8 curved, reversed-cutting mini-needle and tightly ligated so that the dorsal 1/3 to 1/2 of the nerve thickness is held within the ligature. The wound is closed with a single muscle suture (7-0 silk) and a Michelle clip. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, immediately prior to and 1, 3, and 6 hours after drug administration for both the left rear paw and right rear paw of the animal. Percentage reversal of neuropathic hyperalgesia is defined as:

% reversal=100−[(right pre-administration PWT−left post-administration PWT)/(right pre-administration PWT−left pre-administration PWT)]×100.

In the Chung model, the spinal nerve ligation model of neuropathic pain is used to produce mechanical hyperalgesia, themal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then be returned to their home cages until behavioral testing begins. The animals are assessed for response to noxious mechanical stimuli by determining PWT, as described below, immediately prior to and 1, 3, and 5 hours after being administered a Piperazine Compound for both the left rear paw and right rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992). The results show demonstrate Piperazine Compounds that are useful for treating or preventing neuropathic pain.

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacology Biochemistry and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

5.11. Example 11

In Vivo Assays for Prevention or Treatment of Anxiety

The elevated plus maze test or the shock-probe burying test can be used to assess the anxiolytic activity of Piperazine Compounds in rats or mice.

The Elevated Plus Maze Test: The elevated plus maze consists of a platform with 4 arms, two open and two closed (50×10×50 cm enclosed with an open roof). Rats (or mice) are placed in the center of the platform, at the crossroad of the 4 arms, facing one of the closed arms. Time spent in the open arms vs the closed arms and number of open arm entries during the testing period are recorded. This test is conducted prior to drug administration and again after drug administration. Test results are expressed as the mean time spent in open arms and the mean number of entries into open arms. Known anxiolytic drugs increase both the time spent in open arms and number of open arm entries. The elevated plus maze test is described in D. Treit, "Animal Models for the Study of Anti-anxiety Agents: A Review," *Neuroscience & Biobehavioral Reviews* 9(2):203-222 (1985).

The Shock-Probe Burying Test: For the shock-probe burying test the testing apparatus consists of a plexiglass box measuring 40×30×40 cm, evenly covered with approximately 5 cm of bedding material (odor absorbent kitty litter) with a small hole in one end through which a shock probe (6.5 cm long and 0.5 cm in diameter) is inserted. The plexiglass shock probe is helically wrapped with two copper wires through which an electric current is administered. The current is set at 2 mA. Rats are habituated to the testing apparatus for 30 min on 4 consecutive days without the shock probe in the box. On test day, rats are placed in one corner of the test chamber following drug administration. The probe is not electrified until the rat touches it with its snout or fore paws, at which point the rat receives a brief 2 mA shock. The 15 min testing period begins once the rat receives its first shock and the probe remains electrified for the remainder of the testing period. The shock elicits burying behavior by the rat. Following the first shock, the duration of time the rat spends spraying bedding material toward or over the probe with its snout or fore paws (burying behavior) is measured as well as the number of contact-induced shocks the rat receives from the probe. Known anxiolytic drugs reduce the amount of burying behavior. In addition, an index of the rat's reactivity to each shock is scored on a 4 point scale. The total time spent immobile during the 15 min testing period is used as an index of general activity. The shock-probe burying test is described in D. Treit, 1985, supra. The results demonstrate Piperazine Compounds that are useful for treating or preventing anxiety.

5.12. Example 12

In Vivo Assays for Prevention or Treatment of an Addictive Disorder

The condition place preference test or drug self-administration test can be used to assess the ability of Piperazine Compounds to attenuate the rewarding properties of known drugs of abuse.

The Condition Place Preference Test: The apparatus for the conditioned place preference test consists of two large compartments (45×45×30 cm) made of wood with a plexiglass front wall. These two large compartments are distinctly different. Doors at the back of each large compartment lead to a smaller box (36×18×20 cm) box made of wood, painted grey, with a ceiling of wire mesh. The two large compartments differ in terms of shading (white vs black), level of illumination (the plexiglass door of the white compartment is covered with aluminum foil except for a window of 7×7 cm), texture (the white compartment has a 3 cm thick floor board (40×40 cm) with nine equally spaced 5 cm diameter holes and the black has a wire mesh floor), and olfactory cues (saline in the white compartment and 1 mL of 10% acetic acid in the black compartment). On habituation and testing days, the doors to the small box remain open, giving the rat free access to both large compartments.

The first session that a rat is placed in the apparatus is a habituation session and entrances to the smaller grey compartment remain open giving the rat free access to both large compartments. During habituation, rats generally show no preference for either compartment. Following habituation, rats are given 6 conditioning sessions. Rats are divided into 4 groups: carrier pre-treatment+carrier (control group), 2-Pyrimidinylpiperazine Compound pre-treatment+carrier, carrier pre-treatment+morphine, 2-Pyrimidinylpiperazine Compound pre-treatment+morphine. During each conditioning session the rat is injected with one of the drug combinations and confined to one compartment for 30 min. On the following day, the rat receives a carrier+carrier treatment and is confined to the other large compartment. Each rat receives three conditioning sessions consisting of 3 drug combination-compartment and 3 carrier-compartment pairings. The order of injections and the drug/compartment pairings are counterbalanced within groups. On the test day, rats are injected prior to testing (30 min to 1 hour) with either morphine or carrier and the rat is placed in the apparatus, the doors to the grey compartment remain open and the rat is allowed to explore the entire apparatus for 20 min. The time spent in each compartment is recorded. Known drugs of abuse increase the time spent in the drug-paired compartment during the testing session. If the Piperazine Compound blocks the acquisition of morphine conditioned place preference (reward), there will be no difference in time spent in each side in rats pre-treated with a Piperazine Compound and the group will not be different from the group of rats that was given carrier+carrier in both compartments. Data will be analyzed as time spent in each compartment (drug combination-paired vs carrier-paired). Generally, the experiment is repeated with a minimum of 3 doses of a Piperazine Compound.

The Drug Self-Administration Test: The apparatus for the drug self-administration test is a standard commercially available operant conditioning chamber. Before drug trials begin rats are trained to press a lever for a food reward. After stable lever pressing behavior is acquired, rats are tested for acquisition of lever pressing for drug reward. Rats are implanted with chronically indwelling jugular catheters for i.v. administration of compounds and are allowed to recover for 7 days before training begins. Experimental sessions are conducted daily for 5 days in 3 hour sessions. Rats are trained to self-administer a known drug of abuse, such as morphine. Rats are then presented with two levers, an "active" lever and an "inactive" lever. Pressing of the active lever results in drug infusion on a fixed ratio 1 (FR1) schedule (i.e., one lever press gives an infusion) followed by a 20 second time out period (signaled by illumination of a light above the levers). Pressing of the inactive lever results in infusion of excipient. Training continues until the total number of morphine infusions stabilizes to within ±10% per session. Trained rats are then used to evaluate the effect of Piperazine Compounds pre-treatment on drug self-administration. On test day, rats are pre-treated with a Piperazine Compound or excipient and then are allowed to self-administer drug as usual. If the Piperazine Compound blocks the rewarding effects of morphine, rats pre-treated with the Piperazine Compound will show a lower rate of responding compared to their previous rate of responding and compared to excipient pre-treated rats. Data is analyzed as the change in number of drug infusions per testing session (number of infusions during test session−number of infusions during training session). The results show that Piperazine Compounds are useful for treating or preventing an addictive disorder.

5.13. Example 13

Functional Assay for Characterizing mGluR 1 Antagonistic Properties

Functional assays for the characterization of mGluR1 antagonistic properties are well known in the art. For example, the following procedure can be used.

cDNA encoding rat mGluR1a receptor is obtained from, e.g., Prof. S. Nakanishi (Kyoto, Japan). It is transiently transfected into HEK-EBNA cells using a procedure described by Schlaeger et al., *New Dev. New Appl. Anim. Cell Techn.*, Proc. ESACT Meet., 15$^{th}$à (1998), 105-112 and 117-120. [Ca$^{2+}$] measurements are performed on mGluR1a transfected HEK-EBNA cells after incubation of the cells with Fluo-3 AM (0.5 µM final concentration) for 1 hour at 37° C. followed by 4 washes with assay buffer (DMEM supplemented with Hank's salt and 20 mM HEPES). [Ca$^{2+}$] measurements are done using a flurometric imaging plate reader, e.g., FLIPR from Molecular Devices Corporation, La Jolla, Calif. 10 µM glutamate as agonist is used to evaluate the potency of the antagonists.

Increasing concentrations of antagonists are applied to the cells 5 minutes prior to application of the agonist. The inhibition (antagonists) curves are fitted with appropriate software, for example, the four-parameter logistic equation giving IC$_{50}$ and Hill coefficient using the iterative nonlinear curve fitting software Origin from Microcal Software Inc., Northampton, Mass.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A method for treating pain in an animal, comprising administering to an animal in need thereof an effective amount of the compound or a pharmaceutically acceptable salt of the compound of formula:

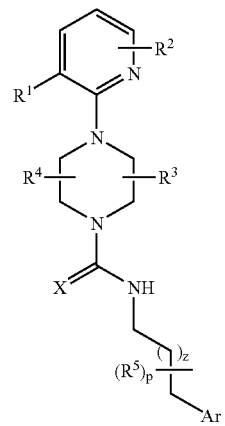

wherein:
X is O or S;
z is 0 or 1;
when z is 0, R$^1$ is —CH$_3$ or -halo;
when z is 1, R$^1$ is —H, -halo, —(C$_1$-C$_6$)alkyl, —NO$_2$, —CN, —OH, —OCH$_3$, —C(halo)$_3$, —CH(halo)$_2$, or —CH$_2$(halo);
R$^2$ is:
  (a) —(C$_2$-C$_6$)alkyl, —(C$_2$-C$_3$)alkenyl, —(CH$_2$)$_n$C(O)R$^6$, —(CH$_2$)$_n$OR$^6$, —(CH$_2$)$_n$SR$^6$, which is unsubstituted or substituted with one or more of —CN, —OH, -halo, —NO$_2$, —CH=NR$^6$, or —NR$^6$OH;
  (b) —CH$_3$, —CH$_2$F, or —CHF$_2$, which is unsubstituted or substituted with one or more of —CN, —OH, —Cl, —Br, —I, —NO$_2$, —CH=NR$^6$, or —NR$^6$OH; or
  (c) —H, -halo, —NO$_2$, —CN, or —NH$_2$;
R$^3$ is:
  (a) —(C$_1$-C$_6$)alkyl, —(C$_2$-C$_6$)alkenyl, —(C$_2$-C$_6$)alkynyl, —(CH$_2$)$_n$OR$^6$, which is unsubstituted or substituted with one or more of —CN, —OH, -halo, —NO$_2$, —CH=NR$^6$, or —NR$^6$OH; or
  (b) —H, -halo, —NO$_2$, —CN, or —NH$_2$;
R$^4$ is —H;
Ar is —(C$_6$)aryl, —(C$_{10}$)aryl, —(C$_{14}$)aryl, —(C$_3$-C$_8$)cycloalkyl or —(C$_5$-C$_8$)cycloalkenyl, which is unsubstituted or substituted with one or more R$^7$ groups;
each R$^5$ is independently —(C$_1$-C$_6$)alkyl, —(C$_2$-C$_6$)alkenyl, —(C$_2$-C$_6$)alkynyl, —(CH$_2$)$_n$(C$_3$-C$_8$)cycloalkyl, —(CH$_2$)$_n$(C$_5$-C$_8$)cycloalkenyl, —(CH$_2$)$_n$(C$_6$)aryl, —(CH$_2$)$_n$SR$^6$, —(CH$_2$)$_n$CH(halo)$_2$, —(CH$_2$)$_n$C(halo)$_3$, -halo, or —(CH$_2$)$_n$OR$^6$;
each R$^6$ is independently —(C$_1$-C$_6$)alkyl, —(C$_2$-C$_6$)alkenyl, —(C$_2$-C$_6$)alkynyl, or -aryl;
each R$^7$ is independently —(C$_1$-C$_6$)alkyl, —(C$_2$-C$_6$)alkenyl, —(C$_2$-C$_6$)alkynyl, —(CH$_2$)$_n$(C$_3$-C$_8$)cycloalkyl, —(CH$_2$)$_n$(C$_5$-C$_8$)cycloalkenyl, —(CH$_2$)$_n$(C$_6$)aryl, —(CH$_2$)$_n$SR$^6$, —(CH$_2$)$_n$CH(halo)$_2$, —(CH$_2$)$_n$C(halo)$_3$, -halo, or —(CH$_2$)$_n$OR$^6$;
n is an integer ranging from 0 to 2; and
p is an integer ranging from 0 to 2.

2. The method of claim 1, further comprising administering an effective amount of an opioid analgesic.

3. The method of claim 1, further comprising administering an effective amount of a non-opioid analgesic.

4. The method of claim 1, further comprising administering an effective amount of an anti-emetic agent.

5. A method for treating pain in an animal, comprising administering to an animal in need thereof an effective amount of the compound or a pharmaceutically acceptable salt of the compound of formula:

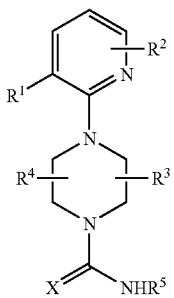

wherein:
X is O or S;
$R^1$ is —$CH_3$ or -halo;
$R^2$ is:
(a) —($C_2$-$C_6$)alkyl, —($C_2$-$C_3$)alkenyl, —$CH_3$, —$CH_2F$, or —$CHF_2$, which is substituted with one or more of —$NO_2$, —CH=$NR^6$, or —$NR^6OH$; or
(b) —($CH_2)_m$C(O)$R^6$, —($CH_2)_m$O$R^6$, or —($CH_2)_m$S$R^6$, which is unsubstituted or substituted with one or more of —CN, —OH, -halo, —$NO_2$, —CH=$NR^6$, or —$NR^6OH$;

$R^3$ is:
(a) —($C_1$-$C_6$)alkyl, —($C_2$-$C_6$)alkenyl, —($C_2$-$C_6$)alkynyl, —($CH_2)_n$O$R^6$, which is unsubstituted or substituted with one or more of —CN, —OH, -halo, —$NO_2$, —CH=$NR^6$, or —$NR^6OH$; or
(b) —H, -halo, —$NO_2$, —CN, or —$NH_2$;

$R^4$ is —H;
$R^5$ is:
(a) —($C_2$-$C_6$)alkenyl, or —($C_2$-$C_6$)alkynyl; or
(b) —($C_3$-$C_8$)cycloalkyl, —($C_5$-$C_8$)cycloalkenyl, —($C_6$)aryl, —($C_{10}$)aryl, —($C_{14}$)aryl, —($C_3$-$C_7$)heterocycle, —($C_1$-$C_6$)alkyl($C_6$)aryl, —($C_1$-$C_6$)alkyl($C_{10}$)aryl, —($C_1$-$C_6$)alkyl($C_{14}$)aryl, —($C_1$-$C_6$)alkyl($C_3$-$C_7$)heterocycle, —($C_2$-$C_6$)alkenyl($C_6$)aryl, —($C_2$-$C_6$)alkenyl($C_{10}$)aryl, —($C_2$-$C_6$)alkenyl($C_{14}$)aryl, —($C_2$-$C_6$)alkenyl($C_3$-$C_7$)heterocycle, —($C_2$-$C_6$)alkynyl($C_3$-$C_8$)cycloalkyl, —($C_2$-$C_6$)alkynyl($C_5$-$C_8$)cycloalkenyl, —($C_2$-$C_6$)alkynyl($C_6$)aryl, —($C_2$-$C_6$)alkynyl($C_{10}$)aryl, —($C_2$-$C_6$)alkynyl($C_{14}$)aryl, or —($C_2$-$C_6$)alkynyl($C_3$-$C_7$)heterocycle, which is unsubstituted or substituted with one or more $R^7$ groups;

each $R^6$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_6$)aryl, —($C_3$-$C_5$)heterocycle, —C(halo)$_3$, or —CH(halo)$_2$;

each $R^7$ is independently —($C_1$-$C_6$)alkyl, —($C_2$-$C_6$)alkenyl, —($C_2$-$C_6$)alkynyl, —($CH_2)_n$($C_3$-$C_8$)cycloalkyl, —($CH_2)_n$($C_5$-$C_8$)cycloalkenyl, —($CH_2)_n$($C_6$)aryl, —($CH_2)_n$S$R^6$, —($CH_2)_n$CH(halo)$_2$, —($CH_2)_n$C(halo)$_3$, -halo, or —($CH_2)_n$O$R^6$;

m is 1 or 2; and
n is an integer ranging from 0 to 2.

6. The method of claim 5, further comprising administering an effective amount of an opioid analgesic.

7. The method of claim 5, further comprising administering an effective amount of a non-opioid analgesic.

8. The method of claim 5, further comprising administering an effective amount of an anti-emetic agent.

9. A method for treating pain in an animal, comprising administering to an animal in need thereof an effective amount of the compound or a pharmaceutically acceptable salt of the compound of formula:

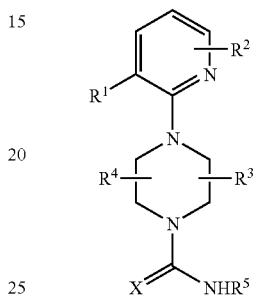

wherein:
X is O or S;
$R^1$ is —$CH_3$ or -halo;
$R^2$ is:
(a) —($C_2$-$C_6$)alkyl, —($C_2$-$C_3$)alkenyl, —($CH_2)_n$C(O)$R^6$, —($CH_2)_n$O$R^6$, —($CH_2)_n$S$R^6$, which is unsubstituted or substituted with one or more of —CN, —OH, -halo, —$NO_2$, —CH=$NR^6$, or —$NR^6OH$;
(b) —$CH_3$, —$CH_2F$, or —$CHF_2$, which is unsubstituted or substituted with one or more of —CN, —OH, —Cl, —Br, —I, —$NO_2$, —CH=$NR^6$, or —$NR^6OH$; or
(c) —H, -halo, —$NO_2$, —CN, or —$NH_2$;

$R^3$ is:
(a) —($C_1$-$C_6$)alkyl, —($C_2$-$C_6$)alkenyl, or —($C_2$-$C_6$)alkynyl, which is substituted with one or more of —CH=$NR^6$ or —$NR^6OH$; or
(b) —($CH_2)_m$O$R^6$, which is unsubstituted or substituted with one or more of —CN, —OH, -halo, —$NO_2$, —CH=$NR^6$, or —NR OH;

$R^4$ is —H;
$R^5$ is:
(a) —($C_2$-$C_6$)alkenyl, or —($C_2$-$C_6$)alkynyl; or
(b) —($C_3$-$C_8$)cycloalkyl, —($C_5$-$C_8$)cycloalkenyl, —($C_6$)aryl, —($C_{10}$)aryl, —($C_{14}$)aryl, —($C_3$-$C_7$)heterocycle, —($C_1$-$C_6$)alkyl($C_6$)aryl, —($C_1$-$C_6$)alkyl($C_{10}$)aryl, —($C_1$-$C_6$)alkyl($C_{14}$)aryl, —($C_1$-$C_6$)alkyl($C_3$-$C_7$)heterocycle, —($C_2$-$C_6$)alkenyl($C_6$)aryl, —($C_2$-$C_6$)alkenyl($C_{10}$)aryl, —($C_2$-$C_6$)alkenyl($C_{14}$)aryl, —($C_2$-$C_6$)alkenyl($C_3$-$C_7$)heterocycle, —($C_2$-$C_6$)alkynyl($C_3$-$C_8$)cycloalkyl, —($C_2$-$C_6$)alkynyl($C_5$-$C_8$)cycloalkenyl, —($C_2$-$C_6$)alkynyl($C_6$)aryl, —($C_2$-$C_6$)alkynyl($C_{10}$)aryl, —($C_2$-$C_6$)alkynyl($C_{14}$)aryl, or —($C_2$-$C_6$)alkynyl($C_3$-$C_7$)heterocycle, which is unsubstituted or substituted with one or more $R^7$ groups;

each $R^6$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, —($C_6$)aryl, —($C_3$-$C_5$)heterocycle, —C(halo)$_3$, or —CH(halo)$_2$;

each $R^7$ is independently —$(C_1$-$C_6)$alkyl, —$(C_2$-$C_6)$alkenyl, —$(C_2$-$C_6)$alkynyl, —$(CH_2)_n(C_3$-$C_8)$cycloalkyl, —$(CH_2)_n(C_5$-$C_8)$cycloalkenyl, —$(CH_2)_n(C_6)$aryl, —$(CH_2)_nSR^6$, —$(CH_2)_nCH(halo)_2$, —$(CH_2)_nC(halo)_3$, -halo, or —$(CH_2)_nOR^6$;

m is 1 or 2; and n is an integer ranging from 0 to 2.

10. The method of claim 9, further comprising administering an effective amount of an opioid analgesic.

11. The method of claim 9, further comprising administering an effective amount of a non-opioid analgesic.

12. The method of claim 9, further comprising administering an effective amount of an anti-emetic agent.

13. The method of claim 10, further comprising administering an effective amount of an anti-emetic agent.

14. The method of claim 11, further comprising administering an effective amount of an anti-emetic agent.

15. The method of claim 2, further comprising administering an effective amount of an anti-emetic agent.

16. The method of claim 3, further comprising administering an effective amount of an anti-emetic agent.

17. The method of claim 6, further comprising administering an effective amount of an anti-emetic agent.

18. The method of claim 7, further comprising administering an effective amount of an anti-emetic agent.

\* \* \* \* \*